US007183382B2

(12) United States Patent
Oppmann et al.

(10) Patent No.: US 7,183,382 B2
(45) Date of Patent: Feb. 27, 2007

(54) MAMMALIAN GENES; RELATED REAGENTS AND METHODS

(75) Inventors: Birgit Oppmann, Berlin (DE); Rene De Waal Malefyt, Sunnyvale, CA (US); Donna M. Rennick, Los Altos, CA (US); Robert A. Kastelein, Redwood City, CA (US); Maria T. Wiekowski, Wayne, NJ (US); Sergio A. Lira, Chatham, NJ (US); Satwant K. Narula, West Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 373 days.

(21) Appl. No.: 10/375,706

(22) Filed: Feb. 27, 2003

(65) Prior Publication Data

US 2003/0162261 A1 Aug. 28, 2003

(51) Int. Cl.
*C12P 21/00* (2006.01)
*C12N 5/10* (2006.01)
*C07K 19/00* (2006.01)
*C07H 21/04* (2006.01)

(52) U.S. Cl. ............ 530/351; 530/827; 536/23.4; 536/23.5; 435/320.1; 435/325; 435/69.7; 435/70.1

(58) Field of Classification Search ............ 530/351; 435/325, 320.1, 69.7; 536/23.4
See application file for complete search history.

(56) References Cited

U.S. PATENT DOCUMENTS

| 5,547,852 A | 8/1996 | Seiler et al. |
| 5,571,515 A | 11/1996 | Scott et al. |
| 5,650,492 A | 7/1997 | Gately et al. |
| 5,744,132 A | 4/1998 | Warne et al. |
| 5,853,721 A | 12/1998 | Gately et al. |
| 5,891,680 A | 4/1999 | Lieschke et al. |

FOREIGN PATENT DOCUMENTS

WO WO 99/05280 2/1999

OTHER PUBLICATIONS

The American Heritage College Dictionary, Third Edition. [1993] definition of "surmise." Houghton Mifflin Company, Boston. p. 1366.*
A.M. Ackrill, *Genbank*, Accession No. X97019, Apr. 11, 1996. "M.monax mRNA for Il-12 p40 subunit."
G.F. Belke-Louis and M. Buettner, et al., *Genbank*, Accession No. U49100, Mar. 13, 1996. "Canis familiaris interleukin-12 p40 subunit mRNA, complete cds."
J.C. Beyer, et al., *Genbank*, Accession No. AF007576, Jul. 14, 1997. Capra hircus interleukin 12 p40 subunit (IL-12) mRNA, complete cds.

D. Fehr, et al., *Genbank*, Accession No. U83184, Jul. 16, 1999. "Felis catus interleukin-12 p40 subunit (IL-12) mRNA, complete cds."
M. Fischer, et al., *Nature Biotechnology*, 15: 142-145, 1997. "A bioactive designer cytokine for human hematopoietic progenitor cell expansion".
M.K. Gately, et al., *Annual Review of Immunology*, 16:495-521, 1998. "The interleukin-12 /interleukin-12-receptor syste m: role in normal and pathologic immune responses".
R.E. Goodman and G.B. Toews, *GenBank*, Accession No. U16674, Nov. 7, 1994, "Rattus norvegicus interleukin-12p40 mRNA, partial cds."
Angela Gronenborn and G.M. Clore, *Protein Engineering*, 4(3):263-269, 1991. "Modeling the three-dimensional structure of the monocyte chemo-attractant protein MCAF/MCP-1 on the basis of the solution structure of interleukin-8".
J. Grotzinger, et al., *Proteins*, 27:96-109, 1997. "The family of the IL-6-type cytokines: specificity and promiscuity of the receptor complexes".
U. Gubler, et al., *Genbank*, Accession No. M65272, Apr. 27, 1993. "Human cytotoxic lymphocyte maturation factor 40 kDa subunit mRNA, complete cds."
J. Khalife, et al. *GenBank*, Accession No. AF133197, Apr. 8, 1999. "Rattus norvegicus interleukin-12 p40 precursor, mRNA, complete cds."
T. Kitamura, et al., *Proceedings of the National Academy of Sciences, USA*, 92:9146-9150, 1995. "Efficient screening of retroviral cDNA expression libraries".
E. Lockhart, et al., *Genbank*, Accession No. U57752, Oct. 28, 1999. "Cervus elaphus interleukin-12 p40 subunit mRNA, complete cds."
L. Nicolson, et al., *Genbank*, Accession No. Y11129, Nov. 17, 1999. "Equus caballus mRNA for interleukin 12 p40 subunit."
M. Onishi, et al., *Experimental Hematology*, 24:324-329, 1996. "Applications of retrovirus-mediated expression cloning".
M. Onishi, et al., *Blood*, 88: 1399-1406, 1996. "Identification of an oncogenic form of the thrombopoietin receptor MPL using retrovirus-mediated gene transfer".
Malte Peters, et al., *The Journal of Immunology*, 161:3575-3581, 1998. "In Vivo and In Vitro Activities of the gp130-Stimulating Designer Cytokine Hyper-IL-6".
Douglas Presky, et al., *Proceedings of the National Academy of Sciences, USA*, 93:14002-14007, Nov. 1996 "A functional interleukin 12 receptor complex is composed of two Beta-type cytoline receptor subunits".
Tim Rakemann, et al., *The Journal of Biological Chemistry*, 274:1257-1266, 1999. "The Designer Cytokine Hyper-Interleukin-6 Is a Potent Activator of STAT3-dependent Gene Transcription *in Vivo* and *in Vitro*".

(Continued)

*Primary Examiner*—Christina Chan
*Assistant Examiner*—F. Pierre VanderVegt
(74) *Attorney, Agent, or Firm*—Edwin P. Ching; Ping F. Hwung; Tina W. McKeon

(57) ABSTRACT

Purified genes encoding cytokine from a mammal, reagents related thereto including purified proteins, specific antibodies, and nucleic acids encoding this molecule are provided. Methods of using said reagents and diagnostic kits are also provided.

22 Claims, No Drawings

OTHER PUBLICATIONS

Roger Sayle and E.J. Milner-White, *Trends in Biochemical Sciences*, 20:374-376, 1995. "RASMOL: biomolecular graphics for all".

V.E. Schijns, et al., *Genbank*, Accession No. Y07762, May 13, 1997. "F.catus mRNA for interleukin-12 p40 chain."

D.S. Schoenhaut, et al., *GenBank*, Accession No. M86671, May 8, 1993. Definition: "Mus musculus interleukin 12 p40 subunit, complete cds."

S.J. Swinburne, et al., *Genbank*, Accession No. AF004024, Nov. 14, 1999. "Ovis aries interleukin-12 p40 subunit precursor, mRNA, complete cds."

T. Taga and T. Kishimoto, *Annual Review of Immunology*, 15: 797-819, 1997. "Interleukin-12: a cytokine at the surface of inflammation and immunity".

G. Trinchieri, *Advances in Immunology*, 70:83-243, 1998. "Interleukin-12: a cytokine at the interface of inflammation and immunity".

G. Trinchieri, *Int. Rev. Immunol.*, 16:365-396, 1998. "Proinflammatory and Immunoregulatory Functions of Interleukin-12".

T. Tsukamoto, et al., *Biochemicist and Biophysicist Research Community*, 265: 7-12, 1999. "Isolation of oncogenes from rat mammafy tumors by a highly efficient retrovirus expression cloning system".

F. Villinger, et al., *Genbank*, Accession No. U19834, Feb. 3, 1996. "Cercocebus torquatus interleukin-12 alpha p40 subunit (IL-12a) mRNA, complete cds."

F. Villinger, et al., *Genbank*, Accession No. U19841, Feb. 3, 1996. "Macaca mulatta interleukin-12 alpha (IL-12a) mRNA, complete cds."

Chang-You Wu, et al. *European Journal of Immunology*, 26:345-350, 1996. "Biological function and distribution of human interleukin-12 receptor chain Beta".

D.S. Zarlenga, et al., *Genbank*, Accession No. U11815, Feb. 27, 1996. "Bos taurus interleukin 12 40 kDa subunit mRNA, complete cds."

* cited by examiner

MAMMALIAN GENES; RELATED REAGENTS AND METHODS

This application claims the benefit of U.S. Provisional Patent Application No. 60/164,616, filed Nov. 10, 1999, and Provisional Patent Application No. 60/153,281, filed Sep. 9, 1999, each of which is incorporated herein by reference.

FIELD OF THE INVENTION

The present invention pertains to compositions and methods related to proteins which function in controlling biology and physiology of mammalian cells, e.g., cells of a mammalian immune system. In particular, it provides purified genes, proteins, antibodies, related reagents, and methods useful, e.g., to regulate activation, development, differentiation, and function of various cell types, including hematopoietic cells.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". See, e.g., Paul, (1998) *Fundamental Immunology* (4th ed.) Raven Press, N.Y. Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders. Some of these factors are hematopoietic growth factors, e.g., granulocyte colony stimulating factor (G-CSF). See, e.g., Thomson, (ed. 1998) *The Cytokine Handbook* (3d ed.) Academic Press, San Diego; Mire-Sluis and Thorpe, (ed. 1998) *Cytokines* Academic Press, San Diego; Metcalf and Nicola, (1995) *The Hematopoietic Colony Stimulating Factors* Cambridge University Press; and Aggarwal and Gutterman, (1991) *Human Cytokines* Blackwell Pub. Cytokine expression by cells of the immune system plays an important role in the regulation of the immune response. Most cytokines are pleiotropic and have multiple biological activities, including antigen-presentation; activation; proliferation and differentiation of CD4+ T cell subsets; antibody response by B cells; and manifestations of hypersensitivity. In addition cytokines may be used in the diagnosis and therapy of a wide range of degenerative or abnormal conditions which directly or indirectly involve the immune system and/or hematopoietic cells.

Lymphokines apparently mediate cellular activities in a variety of ways. They have been shown to support the proliferation, growth, and/or differentiation of pluripotential hematopoietic stem cells into vast numbers of progenitors comprising diverse cellular lineages making up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

From the foregoing, it is evident that the discovery and development of new lymphokines, e.g., related to G-CSF and/or IL-6, could contribute to new therapies for a wide range of degenerative or abnormal conditions which directly or indirectly involve the immune system and/or hematopoietic cells. In particular, the discovery and development of lymphokines which enhance or potentiate the beneficial activities of known lymphokines would be highly advantageous. Originally the novel gene IL-B30 was identified as a potential cytokine based on its predicted structure and was classified as a long-chain cytokine like IL-6 and G-CSF (International Patent Application PCT/US98/15423 (WO 99/05280). IL-6 and related cytokines like Oncostatin M, leukemia inhibitory factor (LIF), ciliary neurotrophic factor (CNTF) and cardiothrophin-1 have biological activities on hematopoiesis, thrombopoiesis, induction of an acute phase response, osteoclast formation, neuron differentiation and survival, and cardiac hypertrophy. Transgenic expression of IL-B30 in mice induced a similar phenotype as that observed after overexpression of IL-6 in mice, comprising runting, systemic inflammation, infertility and death. IL-B30 appears to be a novel cytokine involved in inflammation.

SUMMARY OF THE INVENTION

The present invention is based, in part, upon the discovery of the physiological role of IL-B30, also referred to herein as the IL-B30 protein, and its role in the immune response. In particular, the role of IL-B30 has been elucidated in pathways involved in inflammation, infectious disease, hematopoietic development, and viral infection. The invention is specifically directed to compositions comprising combinations of IL-12 p40 subunit with interleukin-B30 (IL-B30) and their biological activities. It includes nucleic acids coding for both polypeptides or fusion proteins, and methods for their production and use. The nucleic acids of the invention are characterized, in part, by their homology to complementary DNA (cDNA) sequences disclosed herein, and/or by functional assays. Also provided are polypeptides, antibodies, and methods of using them, including using nucleic acid expression methods. Methods for modulating or intervening in the control of a growth factor dependent physiology or an immune response are provided.

The present invention is based, in part, upon the discovery that the p40 subunit of IL-12 also associates with the IL-B30 cytokine, described previously, e.g., in U.S. Ser. Nos. 08/900,905 and 09/122,443, in a natural form. Thus, the coexpression of the two polypeptides together results in functional receptor binding and signaling.

The present invention provides compositions comprising: a) both a substantially pure polypeptide comprising a plurality of distinct segments of at least 7 contiguous amino acid from IL-12 p40 and a substantially pure polypeptide comprising a plurality of distinct segments of at least 7 contiguous amino acids from IL-B30; b) both a substantially pure polypeptide comprising at least 11 contiguous amino acids from IL-12 p40 and a substantially pure polypeptide comprising at least 11 contiguous amino acids from IL-B30; c) a substantially pure polypeptide comprising both a plurality of distinct segments of at least 7 contiguous amino acids of IL-12 p40 and a plurality of distinct segments of at least 7 contiguous amino acids of IL-B30; or d) a substantially pure polypeptide comprising both a segment of at least 11 contiguous amino acids of IL-12 p40 and a segment of at least 11 contiguous amino acids of IL-B30. Various embodiments include such compositions: a) wherein the described plurality of distinct segments of at least 7 contiguous amino acids comprise one segment of at least 9 contiguous amino acids; b) wherein the described plurality of distinct segments of at least 7 contiguous amino acids are both at least 9 contiguous amino acids; c) wherein the described segment of at least 11 contiguous amino acids of IL-12 p40 is at least 15 contiguous amino acids; d) wherein the described segment of at least 11 contiguous amino acids of IL-B30 is at least 15 contiguous amino acids; e) further comprising a carrier selected from an aqueous compound, including water, saline, and/or buffer; f) formulated for oral, rectal, nasal, topical, or parenteral administration; or g) which is sterile composition. Other embodiments include those: a) wherein at least one of the described polypeptides is: i) detectably labeled; ii) recombinantly produced; iii) unglycosylated; iv) denatured; v) attached to a solid substrate; or vi) conjugated to another chemical moiety; b) comprising both a substantially pure IL-12 p40 polypeptide and a substantially pure IL-B30 polypeptide; c) comprising a substantially pure polypeptide comprising IL-12 p40 fused to IL-B30; or d) combined with IL-18, IL-12, radiation or chemotherapy, an immune adjuvant, or an anti-viral. Kit embodiments include those comprising such a described composition and: a) a compartment comprising the described polypeptide; or b) instructions for use or disposal of reagents in the described kit.

Nucleic acid compositions of the invention include, e.g., an isolated or recombinant nucleic acid encoding: a) both a substantially pure polypeptide comprising a plurality of distinct segments of at least 7 contiguous amino acid from IL-12 p40 and a substantially pure polypeptide comprising a plurality of distinct segments of at least 7 contiguous amino acids from IL-B30; b) both a substantially pure polypeptide comprising at least 11 contiguous amino acids from IL-12 p40 and a substantially pure polypeptide comprising at least 11 contiguous amino acids from IL-B30; c) a substantially pure polypeptide comprising both a plurality of distinct segments of at least 7 contiguous amino acids of IL-12 p40 and a plurality of distinct segments of at least 7 contiguous amino acids of IL-B30; or d) a substantially pure polypeptide comprising both a segment of at least 11 contiguous amino acids of IL-12 p40 and a segment of at least 11 contiguous amino acids of IL-B30. Various embodiments include such a nucleic acid: a) wherein the described plurality of distinct segments of at least 7 contiguous amino acids comprise one segment of at least 9 contiguous amino acids; b) wherein the described plurality of distinct segments of at least 7 contiguous amino acids are both at least 9 contiguous amino acids; c) wherein the described segment of at least 11 contiguous amino acids of IL-12 p40 is at least 15 contiguous amino acids; d) wherein the described segment of at least 11 contiguous amino acids of IL-B30 is at least 15 contiguous amino acids; e) wherein the described IL-12 p40 is from a primate; f) wherein the described IL-B30 is from a primate; g) which is an expression vector; h) which further comprises an origin of replication; i) which comprises a detectable label; j) which comprises synthetic nucleotide sequence; k) which is less than 6 kb, preferably less than 3 kb; or l) which is from primate. Also provided is a cell comprising the described recombinant nucleic acid, including wherein the described cell is: a prokaryotic, eukaryotic, bacterial, yeast, insect, mammalian, mouse, primate, or human cell. Kit embodiments include those comprising a described nucleic acid and: a) a compartment comprising the described nucleic acid; b) a compartment further comprising a primate IL-12 p40 polypeptide; c) a compartment further comprising a primate IL-B30 polypeptide; or d) instructions for use or disposal of reagents in the described kit.

Alternatively, the invention provides a nucleic acid which hybridizes: a) under wash conditions of 30 minutes at 50° C. and less than 1M salt to the natural mature coding portion of primate IL-12 p40; and b) under wash conditions of 30 minutes at 50° C. and less than 1M salt to the natural mature coding portion of primate IL-B30. Various embodiments include such a described nucleic acid wherein: a) the described wash conditions for IL-12 p40 are at 60° C. and less than 400 mM salt; b) the described wash conditions for IL-B30 are at 60° C. and less than 400 mM salt; c) the described nucleic acid exhibits identity over a stretch of at least 50 nucleotides to sequence encoding primate IL-12 p40; and/or d) the described nucleic acid exhibits identity over a stretch of at least 50 nucleotides to sequence encoding primate IL-B30. Preferred embodiments include such a nucleic acid wherein: a) the described wash conditions for IL-12 p40 are at 65° C. and less than 150 mM salt; b) the described wash conditions for IL-B30 are at 65° C. and less than 150 mM salt; c) the described nucleic acid exhibits identity over a stretch of at least 90 nucleotides to sequence encoding primate IL-12 p40; and/or d) the described nucleic acid exhibits identity over a stretch of at least 90 nucleotides to sequence encoding primate IL-B30.

Antagonists of the IL-12 p40/IL-B30 compositions are provided, combined with, e.g., a TNFα antagonist, an IL-12 antagonist, IL-10, or steroids.

The invention also provides a binding compound, e.g., comprising an antigen binding site from an antibody, which antibody specifically binds to an IL-12 p40/IL-B30 composition, as described, a) comprising a substantially pure polypeptide comprising both a substantially pure IL-12 p40 polypeptide and a substantially pure IL-B30 polypeptide; or b) comprising a substantially pure polypeptide comprising IL-12 p40 fused to IL-B30; but not to either IL-12 p40 or IL-B30 polypeptide. Other binding compounds include those wherein: a) the described binding compound is in a container; b) the described binding compound is an Fv, Fab, or Fab2 fragment; c) the described binding compound is conjugated to another chemical moiety; or d) the described antibody: i) is raised against an IL-12 p40/IL-B30 composition; ii) is immunoselected; iii) is a polyclonal antibody; iv) exhibits a Kd to antigen of at least 30 mM; v) is attached to a solid substrate, including a bead or plastic membrane; vi) is in a sterile composition; or vii) is detectably labeled, including a radioactive or fluorescent label. Certain preferred forms include compositions comprising: a) a sterile binding compound, as described; or b) the described binding compound and a carrier, wherein the described carrier is: i) an aqueous compound, including water, saline, and/or buffer; and/or ii) formulated for oral, rectal, nasal, topical, or parenteral administration. Additionally, kit embodiments are provided comprising the described binding compound and: a) a compartment comprising the described binding compound; or b) instructions for use or disposal of reagents in the described kit.

Moreover, the invention provides methods for producing an antigen:antibody complex, comprising contacting, under appropriate conditions, a primate IL-12 p40/IL-B30 composition with a described binding compound, thereby allowing the described complex to form. Various methods include those wherein: a) the described complex is purified from other cytokines; b) the described complex is purified from other antibody; c) the described contacting is with a sample comprising a cytokine; d) the described contacting allows quantitative detection of the described antigen; e) the described contacting is with a sample comprising the described antibody; or f) the described contacting allows quantitative detection of the described antibody.

The invention also provides methods of modulating physiology or development of a cell or tissue comprising contacting the described cell with an IL-12 p40/IL-B30 composition, or antagonist thereof. One preferred method is modulating physiology or development of a cell comprising contacting the described cell with an IL-12 p40/IL-B30 composition, and the described contacting results in an increase in production of IFNγ. Typically, the described cell is in a host organism, and the described organism exhibits an enhanced Th1 response, e.g., one selected from an: anti-tumor effect; adjuvant effect; anti-viral effect; or antagonized allergic effect. Often, the contacting is in combination with: IL-18; IL-12; radiation therapy or chemotherapy; an immune adjuvant; or an anti-viral therapeutic.

In another embodiment, the described antagonist is an antibody against IL-12 receptor subunit β1. Thus, the invention also embraces a method, as described, wherein the described contacting is with an antagonist, and the described contacting results in a relative decrease in production of IFNγ. Thus, the invention provides methods of modulating physiology or development of a cell in a host organism, comprising administering the described antagonist to the described organism, wherein the described contacting results in amelioration of: an autoimmune condition or a chronic inflammatory condition.

The identification of the association of the two subunits provides methods of increasing the secretion of: a) a primate IL-B30, such method comprising expressing the described polypeptide with IL-12 p40; or b) a primate IL-12 p40, such method comprising expressing the described IL-12 p40 with IL-B30. Preferably, either: a) the described increasing is at least 3-fold; or b) the described expressing is of a recombinant nucleic acid encoding IL-B30 and IL-12 p40.

Methods for screening for a receptor which binds the described IL-12 p40/IL-B30 composition are provided, e.g., comprising contacting the described complex to a cell expressing the described receptor under conditions allowing the described complex to bind to the described receptor, thereby forming a detectable interaction. Preferably, the described interaction results in a physiological response in the described cell.

The present invention also provides methods of modulating the trafficking or activation of a leukocyte in an animal, the methods comprising contacting monocyte/macrophage lineage cells in the animal with a therapeutic amount of an agonist of a mammalian IL-B30 protein; or an antagonist of a mammalian IL-B30 protein. Preferred embodiments include where: the mammalian IL-B30 protein is a primate protein; and/or the antagonist is an antibody which binds to the mammalian IL-B30. Certain embodiments include where the monocyte/macrophage lineage cells include a microglial cell or a dendritic cell, or where the animal exhibits signs or symptoms of an inflammatory, leukoproliferative, neurodegenerative, or post-traumatic condition. Preferred embodiments include where the sign or symptom is in lung tissue; liver tissue; neural tissue; lymphoid tissue; myeloid tissue; pancreas; gastrointestinal tissue; thyroid tissue; muscle tissue; or skin or collagenous tissue.

Other methods include where the modulating is inhibiting function of the leukocyte cell; and/or where the administering is the agonist. Preferably, the agonist is the mammalian IL-B30.

Certain embodiments include where the animal is experiencing signs or symptoms of autoimmunity; an inflammatory condition; tissue specific autoimmunity; degenerative autoimmunity; rheumatoid arthritis; osteoarthritis; atherosclerosis; multiple sclerosis; vasculitis; delayed hypersensitivities; skin grafting; a transplant; spinal injury; stroke; neurodegeneration; an infectious disease; ischemia; cancer; tumors; multiple myeloma; Castleman's disease; postmenopausal osteoporosis or IL-6-associated diseases. The administering may be in combination with: an anti-inflammatory cytokine agonist or antagonist; an analgesic; an anti-inflammatory agent; or a steroid.

Various other methods are provided where the modulating is enhancing function of the leukocyte cell, and/or the administering is the antagonist. Preferably, the antagonist is: an antibody which binds to the mammalian IL-B30; or a mutein of the mammalian IL-B30 which competes with the mammalian IL-B30 in binding to an IL-B30 receptor, but does not substantially signal. In various embodiments, the method is applied where the animal experiences signs or symptoms of wound healing or clot formation. The administering will often be in combination with: an angiogenic factor; a growth factor, including FGF or PDGF; an antibiotic; or a clotting factor.

Lastly, the present invention provides a method of inducing the proliferation of memory T-cells by administering IL-B30 or an agonist thereof.

DETAILED DESCRIPTION OF THE PREFERRED EMBODIMENTS

All references cited herein are incorporated herein by reference to the same extent as if each individual publication or patent application was specifically and individually indicated to be incorporated by reference.

OUTLINE
I. General
II. Purified IL-12 p40/IL-B30 complex
   A. physical properties
   B. biological properties
III. Physical Variants
   A. sequence variants, fragments
   B. post-translational variants
      1. glycosylation
      2. others
IV. Functional Variants
   A. analogs, fragments
      1. agonists
      2. antagonists B. mimetics
  1. protein
  2. chemicals
C. species variants
V. Antibodies
  A. polyclonal
  B. monoclonal
  C. fragments, binding compositions
VI. Nucleic Acids
  A. natural isolates; methods
  B. synthetic genes
  C. methods to isolate
VII. Making p40/IL-B30 complex, mimetics
  A. recombinant methods
  B. synthetic methods
  C. natural purification
VIII. Uses
  A. diagnostic
  B. therapeutic
IX. Kits
  A. nucleic acid reagents
  B. protein reagents
  C. antibody reagents
X. Isolating receptors for p40/IL-B30 complexes I. General The present invention provides description and teaching of pairing of mammalian proteins to make a soluble cytokine, e.g., a secreted molecule which can mediate a signal between immune or other cells. See, e.g., Paul, (1998) *Fundamental Immunology* (4th ed.) Raven Press, N.Y. Certain soluble factors are made up of heterodimer polypeptides, e.g., IL-6 and IL-12. The dimer forms, which are likely the physiological forms, and fragments, or antagonists will be useful, e.g., in physiological modulation of cells expressing a receptor. It is likely that the functional cytokine comprising p40/IL-B30 complex has either stimulatory or inhibitory effects on hematopoietic cells, including, e.g., lymphoid cells, such as T-cells, B-cells, natural killer (NK) cells, macrophages, dendritic cells, hematopoietic progenitors, etc. The proteins will also be useful as antigens, e.g., immunogens, for raising antibodies to various epitopes on the protein, both linear and conformational epitopes.

The LL-12 p4.0 subunit has been described. See, e.g., Seiler et al., U.S. Pat. No. 5,547,852; Scott and Trinchieri, U.S. Pat. No. 5,571,515; Gately et al., U.S. Pat. No. 5,650,492 (disclosing SEQ ID NO:6); Liesehke and Mulligan, U.S. Pat. No. 5,891,680; Warne et al., U.S. Pat. No. 5,744,132; and accession numbers gbM86671 (SEQ ID NO:7; encoding SEQ ID NO:8; from *Mus musculus*), gbAF133197 (SEQ ID NO:9; encoding SEQ ID NO:10; from *Rattus norvegicus*), gbU16674 (SEQ ID NO:11; encoding SEQ ID NO:12; from *Rattus norvegicus*), gbU83184 (SEQ ID NO:13; encoding SEQ ID NO:14; from *Felis catus*), embY07762 (SEQ ID NO:15; encoding SEQ ID NO:16; from *Felis catus*), embY11129.1 (SEQ ID NO:17; encoding SEQ ID NO:18; from *Equus caballus*), gbM65272 (SEQ ID NO:19; encoding SEQ ID NO:20; from human), gbAF007576 (SEQ ID NO:21; encoding SEQ ID NO:22; from *Capra hircus*), gbU19841 SE ID NO:23; encoding SEQ ID NO:24; from *Macaca mulatta*),gbU11815 (SEQ ID NO:25; encoding SEQ ID NO:26; from *Bos taurus*), gbU57752 (SEQ ID NO:27; encoding SEQ ID NO:28; from *Cervus elaphus*), gbAF004024 (SEQ ID NO:29; encoding SEQ ID NO:30; from *Ovis aries*), gbU49100 (SEQ ID NO:31; encoding SEQ ID NO:32; from *Canis familiaris*), gbU19834 (SEQ ID NO:33; encoding SEQ ID NO:34; from *Cercocebus torguatus*), and embX97019 (SEQ ID NO:35; encoding SEQ ID NO:36; from *M. monax*). A sequence encoding IL-B30 was identified from a human genomic sequence. The molecule was designated huIL-B30. A rodent sequence, e.g., from mouse, was also described. See, e.g., U.S. Ser. Nos. 08/900,905 and 09/122,443. The present invention embraces compositions comprising combinations of these two polypeptides, e.g., p40 and IL-B30, and nucleic acid constructs encoding both sequences. Antibodies which recognize the combinations are also provided, and methods of producing the two messages or polypeptides, e.g., coordinately.

The human IL-B30 gene encodes a small soluble cytokine-like protein, of about 198 amino acids. The psort predicted signal sequence probably is about 17 residues, and would run from the Met to about Ala. See Table 1 and SEQ. ID. NO: 1 and 2. IL-B30 exhibits structural motifs characteristic of a member of the long chain cytokines. Compare, e.g., IL-B30, G-CSF, and IL-6, sequences available from GenBank. See also U.S. Ser. Nos. 08/900,905 and 09/122,443.

TABLE 1

Nucleic acid (SEQ ID NO: 1) ending IL-B30 from a primate, e.g., human. Translated amino acid sequence is SEQ ID NO:2.

```
ATG CGT GGG AGC AGA GCT GTA ATG CTG CTG TTG CTG CTG CCC TGG ACA    48
Met Leu Gly Ser Arg Ala Val Met Leu Leu Leu Leu Leu Pro Trp Thr
-21 -20                 -15                 -10

GCT CAG GGC AGA GCT GTG CCT GGG GGC AGC AGC CCT GCC TGG ACT CAG    96
Ala Gln Gly Arg Ala Val Pro Gly Gly Ser Ser Pro Ala Trp Thr Gln
 -5                   1               5                  10

TGC CAG CAG CTT TCA CAG AAG CTC TGC ACA CTG GCC TGG AGT GCA CAT   144
Cys Gln Gln Leu Ser Gln Lys Leu Cys Thr Leu Ala Trp Ser Ala His
             15                  20                  25

CCA CTA GTG GGA CAC ATG GAT CTA AGA GAA GAG GGA GAT GAA GAG ACT   192
Pro Leu Val Gly His Met Asp Leu Arg Glu Glu Gly Asp Glu Glu Thr
         30                  35                  40

ACA AAT GAT GTT CCC CAT ATC CAG TGT GGA GAT GGC TGT GAC CCC CAA   240
Thr Asn Asp Val Pro His Ile Gln Cys Gly Asp Gly Cys Asp Pro Gln
     45                  50                  55
```

TABLE 1-continued Nucleic acid (SEQ ID NO: 1) ending IL-B30 from a primate, e.g., human.
Translated amino acid sequence is SEQ ID NO:2.

```
GGA CTC AGG GAC AAC AGT CAG TTC TGC TTG CAA AGG ATC CAC CAG GGT     288
Gly Leu Arg Asp Asn Ser Gln Phe Cys Leu Gln Arg Ile His Gln Gly
 60              65                  70                  75

CTG ATT TTT TAT GAG AAG CTG CTA GGA TCG GAT ATT TTC ACA GGG GAG     336
Leu Ile Phe Tyr Glu Lys Leu Leu Gly Ser Asp Ile Phe Thr Gly Glu
                 80                  85                  90

CCT TCT CTG CTC CCT GAT AGC CCT GTG GCG CAG CTT CAT GCC TCC CTA     384
Pro Ser Leu Leu Pro Asp Ser Pro Val Ala Gln Leu His Ala Ser Leu
             95                 100                 105

CTG GGC CTC AGC CAA CTC CTG CAG CCT GAG GGT CAC CAC TGG GAG ACT     432
Leu Gly Leu Ser Gln Leu Leu Gln Pro Glu Gly His His Trp Glu Thr
         110                 115                 120

CAG CAG ATT CCA AGC CTC AGT CCC AGC CAG CCA TGG CAG CGT CTC CTT     480
Gln Gln Ile Pro Ser Leu Ser Pro Ser Gln Pro Trp Gln Arg Leu Leu
     125                 130                 135

CTC CGC TTC AAA ATC CTT CGC AGC CTC CAG GCC TTT GTG GCT GTA GCC     528
Leu Arg Phe Lys Ile Leu Arg Ser Leu Gln Ala Phe Val Ala Val Ala
140                 145                 150                 155

GCC CGG GTC TTT GCC CAT GGA GCA GCA ACC CTG AGT CCC TAA             570
Ala Arg Val Phe Ala His Gly Ala Ala Thr Leu Ser Pro
                 160                 165
```

MLGSRAVMLLLLLPWTAQGRAVPGGSSPAWTQCQQLSQKLCTLAWSAHPLVGHMDLREEGDEE

TTNDVPHIQCGDGCDPQGLRDNSQFCLQRIHQGLIFYEKLLGSDIFTGEPSLLPDSPVAQLHA

SLLGLSQLLQPEGHHWETQQIPSLSPSQPWQRLLLRFKILRSLQAFVAVAARVFAHGAATLSP coding sequence:

ATGCTGGGGA GCAGAGCTGT AATGCTGCTG TTGCTGCTGC CCTGGACAGC

TCAGGGCAGA GCTGTGCCTG GGGGCAGCAG CCCTGCCTGG ACTCAGTGCC

AGCAGCTTTC ACAGAAGCTC TGCACACTGG CCTGGAGTGC ACATCCACTA

GTGGACACA TGGATCTAAG AGAAGAGGGA GATGAAGAGA CTACAAATGA

TGTTCCCCAT ATCCAGTGTG GAGATGGCTG TGACCCCCAA GGACTCAGGG

ACAACAGTCA GTTCTGCTTG CAAAGGATCC ACCAGGGTCT GATTTTTTAT

GAGAAGCTGC TAGGATCGGA TATTTTCACA GGGGAGCCTT CTCTGCTCCC

TGATAGCGCT GTGGCGCAGC TTCATGCCTC CCTACTGGGC CTCAGCCAAC

TCCTGCAGCC TGAGGGTCAC CACTGGGAGA CTCAGCAGAT TCCAAGCCTC

AGTCCCAGCC AGCCATGGCA GCGTCTCCTT CTCCGCTTCA AAATCCTTCG

CAGCCTCCAG GCCTTTGTGG CTGTAGCCGC CCGGGTCTTT GCCCATGGAG

CAGCAACCCT GAGTCCCTAA

Rodent, e.g., mouse, IL-B30 (SEQ ID NO: 3 and 4):

```
CGCTTAGAAG TCGGACTACA GAGTTAGACT CAGAACCAAA GGAGGTGGAT AGGGGGTCCA     60

CAGGCCTGGT GCAGATCACA GAGCCAGCCA GATCTGAGAA GCAGGGAACA AG ATG        115
                                                          Met
                                                          -21

CTG GAT TGC AGA GCA GTA ATA ATG CTA TGG CTG TTG CCC TGG GTC ACT     163
Leu Asp Cys Arg Ala Val Ile Met Leu Trp Leu Leu Pro Trp Val Thr
-20                 -15                 -10                  -5

CAG GGC CTG GCT GTG CCT AGG AGT AGC AGT CCT GAC TGG GCT CAG TGC     211
Gln Gly Leu Ala Val Pro Arg Ser Ser Ser Pro Asp Trp Ala Gln Cys
```

TABLE 1-continued

Nucleic acid (SEQ ID NO: 1) ending IL-B30 from a primate, e.g., human.
Translated amino acid sequence is SEQ ID NO:2.

```
                 1                 5                    10
CAG CAG CTC TCT CGG AAT CTC TGC ATG CTA GCC TGG AAC GCA CAT GCA    259
Gln Gln Leu Ser Arg Asn Leu Cys Met Leu Ala Trp Asn Ala His Ala
            15                  20                  25

CCA GCG GGA CAT ATG AAT CTA CTA AGA GAA GAA GAG GAT GAA GAG ACT    307
Pro Ala Gly His Met Asn Leu Leu Arg Glu Glu Glu Asp Glu Glu Thr
        30                  35                  40

AAA AAT AAT GTG CCC CGT ATC CAG TGT GAA GAT GGT TGT GAC CCA CAA    355
Lys Asn Asn Val Pro Arg Ile Gln Cys Glu Asp Gly Cys Asp Pro Gln
45                  50                  55                  60

GGA CTC AAG GAC AAC AGC CAG TTC TGC TTG CAA AGG ATC CGC CAA GGT    403
Gly Leu Lys Asp Asn Ser Gln Phe Cys Leu Gln Arg Ile Arg Gln Gly
                65                  70                  75

CTG GCT TTT TAT AAG CAC CTG CTT GAC TCT GAC ATC TTC AAA GGG GAG    451
Leu Ala Phe Tyr Lys His Leu Leu Asp Ser Asp Ile Phe Lys Gly Glu
            80                  85                  90

CCT GCT GTA CTC CCT GAT AGG CCC ATG GAG GAA CTT CAC ACC TCC CTA    499
Pro Ala Leu Leu Pro Asp Ser Pro Met Glu Gln Leu His Thr Ser Leu
        95                  100                 105

CTA GGA CTG AGC CAA CTC CTC CAG GGA GAG GAT CAC CCC CGG GAG AGC    547
Leu Gly Leu Ser Gln Leu Leu Gln Pro Glu Asp His Pro Arg Glu Ser
110                 115                 120

CAA GAG ATG CCC AGC CTG AGT TCT AGT GAG GAG TGG GAG GGG CCC GTT    595
Gln Glu Met Pro Ser Leu Ser Ser Ser Glu Glu Trp Glu Gly Pro Val
125                 130                 135                 140

CTG CGT TGG AAG ATC CTT CGA AGC CTC CAG GCC TTT TTG GCC ATA GCT    643
Leu Arg Ser Lys Ile Leu Arg Ser Leu Gln Ala Phe Leu Ala Ile Ala
                145                 150                 155

GCC CGG GTC TTT GCC CAC GGA GCA GCA ACT CTG ACT GAG CCC TTA GTG    691
Ala Arg Val Phe Ala His Gly Ala Ala Thr Leu Thr Glu Pro Leu Val
            160                 165                 170

CCA ACA CGT TAAGGATGCC CAGGTTCCCA TGGCTACCAT GATAAGACTA            740
Pro Thr Ala
        175

ATCTATCACG CCAGACATCT ACCAGTTAAT TAACCCATTA GGACTTGTGC TGTTCTTGTT  800

TCGTTTGTTT TGCGTGAAGG GCAAGGACAC CATTATTAAA GAGAAAAGAA ACAAACCCCA  860

GAGCAGGCAC CTGGCTAGAG AAAGGAGCTG GAGAAGAAGA ATAAAGTCTC GAGCCCTTGG  920

CCTTGGAAGC GGGCAAGCAG CTGCGTGGCC TGAGGGGAAG GGGGCGGTGG CATCGAGAAA  980

CTGTGAGAAA ACCCAGACGA TGAGAAAAAG TGAGCCCAGG CTTTGGCCAT TATCTGTAAG 1040

AAAAACAAGA AAAGGGGAAG ATTATACTTT CCTGGGTGGC TCAGGGAAAT GTGCAGATGC 1100

ACAGTACTCC AGACAGCAGC TCTGTACCTG CCTGCTCTGT CCCTCAGTTC TAACAGAATC 1160

TAGTCACTAA GAACTAACAG GACTACCAAT ACGAACTGAC AAA                   1203
```

MLDCRAVIMLWLLPWVTQGLAVPRSSSPDWAQCQQLSRNLCMLAWNAHAPAGHMNLLREEED

EETKNNVPRIQCEDGCDPQGLKDNSQFCLQRIRQGLAFYKHLLDSDIFKGEPALLPDSPMEQ

LHTSLLGLSQLLQPEDHPRETQQMPSLSSSQQWQRPLLRSKILRSLQAFLAIAARVFAHGAA

TLTEPLVPTA

The structural homology of IL-B30 to related cytokine proteins suggests related function of this molecule. However, recognition of the association of the IL-12 p40 polypeptide with the IL-B30 polypeptide allows for biological assay of active p40/IL-B30 dimers. IL-12 p40/IL-B30 compositions may be made up of either distinct polypeptides representing each of the individual polypeptides, or fusion constructs of IL-12 p40 with IL-B30. Observations indicate that the dimer is capable of inducing interferon-γ (IFNγ) production by various cell types, e.g., PBMC, suggesting biological functions for which the dimer will be used. Moreover, experiments indicate that the IL-12 receptor β1 subunit is a component of the receptor for the p40/IL-B30 dimer.

IFNγ activates macrophages, stimulating tumoricidal and microbicidal activities. It also modulates class I and II MHC molecule expression, including up-regulation of class II molecules on monocytes/macrophages and dendritic cells, and induces expression on epithelial, endothelial, and other cells, rendering them capable of antigen presentation. The cytokine is a Th1-like cytokine which promotes the development of Th1-like CD4+ T cells, but inhibits that of Th2-like T cells. It is a powerful and relatively specific inhibitor of IL-4-induced IgE and IgG4 synthesis by B lymphocytes, although at higher concentrations it non-specifically inhibits the production of all antibody isotypes. IFNγ augments cytotoxic immune responses against intracellular organisms and tumors mediated by NK cells and CTLs. Like IL-12, IFNγ has the propensity to promote cell-mediated cytotoxic response while inhibiting allergic inflammation and IgE synthesis. See, e.g., Karupiah, (ed. 1997) *Gamma Interferon in Antiviral Defense* Chapman & Hall; Jaffe, (ed. 1992) *Anti-Infective Applications of Interferon-Gamma* Marcel Dekker (ISBN: 0824786882); Sutterwala et al., (1999) *J. Leukoc. Biol.* 65:543–551; Billiau et al., (1998) *Ann. NY Acad. Sci.* 856:22–32; and Gessani et al., (1998) *Cytokine Growth Factor Rev.* 9:117–123.

IL-B30 agonists, or antagonists, may also act as functional or receptor antagonists, e.g., which block IL-6 or IL-12 binding to their respective receptors, or mediating the opposite actions. Thus, IL-B30, or its antagonists, may be useful in the treatment of abnormal medical conditions, including immune disorders, e.g., T cell immune deficiencies, chronic inflammation, or tissue rejection, or in cardiovascular or neurophysiological conditions. Agonists would be likely to be used in a therapeutic context of enhancing cell mediated immunity, e.g., in anti-tumor, adjuvant, and antiviral situations, or to antagonize allergic responses. Antagonists would likely be used in the context of blocking such enhanced immunity, e.g., in cellular contributions to autoimmune diseases or chronic inflammatory conditions.

The natural antigens are capable of mediating various biochemical responses which lead to biological or physiological responses in target cells. The preferred embodiments would be from human, but other primate, or other species counterparts exist in nature. Additional sequences for proteins in other mammalian species, e.g., primates, canines, felines, and rodents, should also be available.

In particular, the association of the IL-12 p40 subunit with IL-B30 has been confirmed. The IL-12 p40 and IL-B30 molecules should have evolved together. If the two functionally associate, they might act together in the fashion of IL-12. See, e.g., Trinchieri (1998) *Adv. Immunol.* 70:83–243; Gately et al., (1998) *Ann. Rev. Immunol.* 16:495–521; and Trinchieri (1998) *Int. Rev. Immunol.* 16:365–396.

As a complex, however, the complex would be expected to interact with two tall signaling receptors in the cytokine receptor family. This has been confirmed in the case of IL-12 receptor subunit β1. Other related receptors can be tested for binding to the soluble complex. A series of cells, e.g., BAF/3, that stably express various of these tall receptors capable of signal transduction have been constructed.

The supernatants of transfectants of both IL-12 p40 and IL-B30 (or a single combination construct) in the same cell, were used to test these various cells to see if there is a proliferative or other signaling response. As such, most of the physiological effects of the cytokine may be due to the complex of the proteins. As such, many of the descriptions below of biology resulting from the cytokine may actually be physiologically effected by the complex comprising the combination of the subunits.

The descriptions below may also be applied to the IL-12 p40/IL-B30 complex. A fusion of the IL-12 p40 subunit with the IL-B30 was constructed, as, e.g., the hyper IL-6. See, e.g., Fischer et al., (1997) *Nature Biotechnol.* 15:142–145; Rakemann et al., (1999) *J. Biol. Chem.* 274:1257–1266; and Peters et al., (1998) *J. Immunol.* 161:3575–3581; which are incorporated herein by reference. Moreover, matching of the cytokine complex with a receptor comprising the IL-12 receptor subunit β1 allows for identification of antibodies to that subunit as a receptor antagonist of the cytokine complex.

II. Purified p40/IL-B30 Complex

Human IL-B30 amino acid sequence, is shown as one embodiment within SEQ ID NO: 2. Other naturally occurring nucleic acids which encode the protein can be isolated by standard procedures using the provided sequence, e.g., PCR techniques, or by hybridization. These amino acid sequences, provided amino to carboxy, are important in providing sequence information for the cytokine subunit allowing for distinguishing the protein antigen from other proteins and exemplifying numerous variants. Moreover, the peptide sequences allow preparation of peptides to generate antibodies to recognize segments, and nucleotide sequences allow preparation of oligonucleotide probes, both of which are strategies for detection or isolation, e.g., cloning, of genes encoding such sequences.

As used herein, the term "human soluble IL-B30" shall encompass, when used in a protein context, a protein having amino acid sequence corresponding to a soluble polypeptide from SEQ ID NO: 2. Significant fragments thereof will often retain similar functions, e.g., antigenicity. Preferred embodiments comprise a plurality of distinct, e.g., nonoverlapping, segments of the specified length. Typically, the plurality will be at least two, more usually at least three, and preferably 5, 7, or even more. While the length minima may be recited, longer lengths, of various sizes, may be appropriate, e.g., one of length 7, and two of length 12. Similar features apply to the IL-12 p40 polypeptide, and to polynucleotides of either or both.

Binding components, e.g., antibodies, typically bind to an IL-12 p40/IL-B30 complex with high affinity, e.g., at least about 100 nM, usually better than about 30 nM, preferably better than about 10 nM, and more preferably at better than about 3 nM. Counterpart protein complexes will be found in mammalian species other than human, e.g., other primates, ungulates, or rodents. Non-mammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 175, 174, 173, etc., in all practical combinations for either the IL-B30 or the IL-12 p40 subunit. Particularly interesting peptides have ends corresponding to structural domain boundaries, e.g., helices A, B, C, and/or D of the IL-B30 or the Ig domains of the IL-12 p40. See below.

The term "binding composition" refers to molecules that bind with specificity to the IL-12 p40/IL-B30 complex, e.g., in an antibody-antigen interaction, but not to the individual components alone. The specificity may be more or less inclusive, e.g., specific to a particular embodiment, or to groups of related embodiments, e.g., primate, rodent, etc. Depletion or absorptions can provide desired selectivities, e.g., to deplete antibodies which bind to either polypeptide component alone. Also provided are compounds, e.g., proteins, which specifically associate with the IL-12 p40/IL-B30 complex, including in a natural physiologically relevant protein-protein interaction, either covalent or non-covalent. The molecule may be a polymer, or chemical reagent. A functional analog may be a protein with structural modifications, or it may be a molecule which has a molecular shape which interacts with the appropriate binding determinants. The compounds may serve as agonists or antagonists of a receptor binding interaction, see, e.g., Goodman et al., (eds.), *Goodman & Gilman's: The Pharmacological Bases of Therapeutics* (current ed.) Pergamon Press.

Substantially pure, e.g., in a protein context, typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added. A composition comprising a substantially pure IL-12 p40 and IL-B30 will not have large amounts of extraneous polypeptides which are not naturally associated with the complex of the two polypeptides.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptides should generally be in a substantially stable state, and usually not in a denatured state. The polypeptide may be associated with other polypeptides in a quaternary structure, e.g., to confer solubility, or associated with lipids or detergents. In particular, a complex made up of the association of the two polypeptides is preferred, as is a fusion composition.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein. In other instances, a harsh detergent may be used to effect significant denaturation.

An IL-B30 polypeptide that specifically binds to or that is specifically immunoreactive with an antibody, e.g., such as a polyclonal antibody, generated against a defined immunogen, e.g., such as an immunogen consisting of an amino acid sequence of SEQ ID NO: 2 or fragments thereof or a polypeptide generated from the nucleic acid of SEQ ID NO: 1 is typically determined in an immunoassay. Included within the metes and bounds of the present invention are those nucleic acid sequences described herein, including functional variants, that encode polypeptides that selectively bind to polyclonal antibodies generated against the prototypical IL-B30 polypeptide as structurally and functionally defined herein. The immunoassay typically uses a polyclonal antiserum which was raised, e.g., to a complex comprising a protein of SEQ ID NO: 2. This antiserum is selected, or depleted, to have low crossreactivity against appropriate other closely related family members, preferably from the same species, and any such crossreactivity is removed by immunoabsorption or depletion prior to use in the immunoassay. In particular, antibodies which bind to the IL-12 p40 or the IL-B30 polypeptides alone are targets for immunodepletion. Appropriate selective serum preparations can be isolated, and characterized.

In order to produce antisera for use in an immunoassay, the compls comprising the protein, e.g., of SEQ ID NO: 2, is isolated as described herein. For example, recombinant protein may be produced in a mammalian cell line. An appropriate host, e.g., an inbred strain of mice such as Balb/c, is immunized with the complex comprising a protein of SEQ ID NO: 2 using a standard adjuvant, such as Freund's adjuvant, and a standard mouse immunization protocol (see Harlow and Lane). Alternatively, a substantially full-length synthetic peptide construct derived from the sequences disclosed herein can be used as an immunogen. Polyclonal sera are collected and titered against the immunogen protein in an immunoassay, e.g., a solid phase immunoassay with the immunogen immobilized on a solid support, along with appropriate depletions or selections. Polyclonal antisera with a titer of $10^4$ or greater are selected and tested for their cross reactivity against other closely related family members, e.g., LIF, CT-1, CNTF, or other members of the IL-6 family, using a competitive binding immunoassay such as the one described in Harlow and Lane, supra, at pages 570–573. Preferably at least two individual IL-6/IL-12 family members are used in this determination in conjunction with the target. These long chain cytokine family members can be produced as recombinant proteins and isolated using standard molecular biology and protein chemistry techniques as described herein. Thus, antibody preparations can be identified or produced having desired selectivity or specificity for subsets of IL-12 p40/IL-B30 family members. Alternatively, antibodies may be prepared which bind to fusion polypeptide forms of the complex comprising the IL-12 p40 and IL-B30.

Immunoassays in the competitive binding format can be used for the crossreactivity determinations. For example, the fusion protein can be immobilized to a solid support. Proteins added to the assay compete with the binding of the selective antisera to the immobilized antigen. The ability of the above proteins to compete with the binding of the selective antisera to the immobilized protein is compared to the fusion protein. The percent crossreactivity for the above proteins is calculated, using standard calculations. Those antisera with less than 10% crossreactivity with each of the proteins listed above are selected and pooled. The cross-reacting selective antibodies are then removed from the pooled antisera by immunoabsorption with the above-listed proteins.

The immunoabsorbed and pooled antisera are then used in a competitive binding immunoassay as described above to compare a second protein to the immunogen fusion protein. In order to make this comparison, the two proteins are each assayed at a wide range of concentrations and the amount of each protein required to inhibit 50% of the binding of the selective antisera to the immobilized fusion protein is determined. If the amount of the second protein required is less than twice the amount of the fusion protein that is required, then the second protein is said to specifically bind to a selective antibody generated to the immunogen.

III. Physical Variants

This invention also encompasses complexes comprising proteins or peptides having substantial amino acid sequence identity with the amino acid sequences of the IL-12 p40/IL-B30 antigen. The variants include species, polymorphic, or allelic variants.

Amino acid sequence homology, or sequence identity, is determined by optimizing residue matches, if necessary, by introducing gaps as required. See also Needleham et al., (1970) *J. Mol. Biol.* 48:443–453; Sankoff et al., (1983) Chapter One in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. The conservation may apply to biological features, functional features, or structural features. Homologous amino acid sequences are typically intended to include natural polymorphic or allelic and interspecies variations of a protein sequence. Typical homologous proteins or peptides will have from 25–100% identity (if gaps can be introduced), to 50–100% identity (if conservative substitutions are included) with the amino acid sequence of the IL-B30. Identity measures will be at least about 35%, generally at least about 40%, often at least about 50%, typically at least about 60%, usually at least about 70%, preferably at least about 80%, and more preferably at least about 90%.

The isolated IL-12 p40 or IL-B30 DNA can be readily modified by nucleotide substitutions, nucleotide deletions, nucleotide insertions, and inversions of short nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant IL-B30" encompasses a polypeptide otherwise falling within the sequence identity definition of the IL-B30 as set forth above, but having an amino acid sequence which differs from that of IL-B30 as normally found in nature, whether by way of deletion, substitution, or insertion. This generally includes proteins having significant identity with a protein having sequence of SEQ ID NO: 2, and as sharing various biological activities, e.g., antigenic or immunogenic, with those sequences, and in preferred embodiments contain most of the natural full-length disclosed sequences. Full-length sequences will typically be preferred, though truncated versions will also be useful, likewise, genes or proteins found from natural sources are typically most desired. Similar concepts apply to different IL-B30 proteins, particularly those found in various warm-blooded animals, e.g., mammals and birds. These descriptions are generally meant to encompass various IL-B30 proteins, not limited to the particular primate embodiments specifically discussed.

IL-12 p40 or IL-B30 mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook et al., (1989); Ausubel et al., (1987 and Supplements); and Kunkel et al., (1987) *Methods in Enzymol.* 154:367–382. Preferred embodiments include, e.g., 1-fold, 2-fold, 3-fold, 5-fold, 7-fold, etc., preferably conservative substitutions at the nucleotide or amino acid levels. Preferably the substitutions will be away from the conserved cysteines, and often will be in the regions away from the helical structural domains. Such variants may be useful to produce specific antibodies, and often will share many or all biological properties. Recognition of the cytokine structure provides important insight into the structure and positions of residues which may be modified to effect desired changes in receptor interaction. Also, the interaction of the IL-12 p40 with the IL-B30 protein requires complementary structural features in the interacting surface. Structural analysis will further allow prediction of the surface residues critical in both complex formation and complex to receptor interaction.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments. See, e.g., Cunningham et al., (1989) *Science* 243:1330–1336; and O'Dowd et al., (1988) *J. Biol. Chem.* 263:15985–15992.

The phosphoramidite method described by Beaucage and Carruthers, (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

Structural analysis can be applied to this gene, in comparison to the IL-6 family of cytokines. The family includes, e.g., IL-6, IL-11, IL-12, G-CSF, LIF, OSM, CNTF, and Ob. Alignment of the human and mouse IL-B30 sequences with other members of the IL-6 family should allow definition of structural features. In particular, β-sheet and α-helix residues can be determined using, e.g., RASMOL program, see Bazan et al., (1996) *Nature* 379:591; Lodi et al., (1994) *Science* 263:1762–1766; Sayle and Milner-White, (1995) *TIBS* 20:374–376; and Gronenberg et al., (1991) *Protein Engineering* 4:263–269. See, also, Wilkins et al., (eds. 1997) *Proteome Research: New Frontiers in Functional Genomics* Springer-Verlag, N.Y. Preferred residues for substitutions include the surface exposed residues which would be predicted to interact with receptor. Other residues which should conserve function will be conservative substitutions, particularly at a position far from the surface exposed residues.

IV. Functional Variants

The blocking of physiological response to the IL-12 p40/IL-B30 complexes may result from the competitive inhibition of binding of the ligand to its receptor. Identification of one subunit of the receptor allows for further characterization, as described, and use of antibodies to that subunit to block binding and/or signaling with the complex.

In vitro assays of the present invention will often use isolated complex, protein, soluble fragments comprising receptor binding segments of these proteins, or fragments attached to solid phase substrates. These assays will also allow for the diagnostic determination of the effects of either binding segment mutations and modifications, or cytokine mutations and modifications, e.g., IL-12 p40/IL-B30 complex analogs.

This invention also contemplates the use of competitive drug screening assays, e.g., where neutralizing antibodies to the cytokine complex, or receptor binding fragments compete with a test compound.

"Derivatives" of IL-12 p40/IL-B30 antigens include amino acid sequence mutants from naturally occurring forms, glycosylation variants, and covalent or aggregate conjugates with other chemical moieties. Covalent derivatives can be prepared by linkage of functionalities to groups which are found in IL-12 p40/IL-B30 complex amino acid side chains or at the N- or C-termini, e.g., by standard means. See, e.g., Lundblad and Noyes, (1988) *Chemical Reagents for Protein Modification*, vols. 1–2, CRC Press, Inc., Boca Raton, Fla.; Hugli, (ed. 1989) *Techniques in Protein Chemistry*, Academic Press, San Diego, Calif.; and Wong, (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein, (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between the IL-12 p40 and IL-B30 are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski et al., (1988) *Science* 241:812–816. Fusion constructs with other therapeutic entities, e.g., which are to be coadministered, but proteolytically cleaved, are also provided.

Fusion peptides will typically be made by either recombinant nucleic acid methods or by synthetic polypeptide methods. Techniques for nucleic acid manipulation and expression are described generally, e.g., in Sambrook et al., (1989) *Molecular Cloning: A Laboratory Manual* (2d ed.), vols. 1–3, Cold Spring Harbor Laboratory; and Ausubel et al., (eds. 1993) *Current Protocols in Molecular Biology*, Greene and Wiley, NY. Techniques for synthesis of polypeptides are described, e.g., in Merrifield, (1963) *J. Amer. Chem. Soc.* 85:2149–2156; Merrifield, (1986) *Science* 232:341–347; Atherton et al., (1989) *Solid Phase Peptide Synthesis: A Practical Approach*, IRL Press, Oxford; and Grant, (1992) *Synthetic Peptides: A User's Guide*, W. H. Freeman, NY. Refolding methods may be applicable to synthetic proteins.

This invention also contemplates the use of derivatives of IL-12 p40 or IL-B30 proteins other than variations in amino acid sequence or glycosylation. Such derivatives may involve covalent or aggregative association with chemical moieties or protein carriers. Covalent or aggregative derivatives will be useful as immunogens, as reagents in immunoassays, or in purification methods such as for affinity purification of binding partners, e.g., other antigens. An IL-12 p40 or IL-B30 can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-IL-12 p40 or IL-B30 antibodies or an alternative binding composition. The IL-12 p40, IL-B30, or fusion proteins can also be labeled with a detectable group, e.g., for use in diagnostic assays. Purification of IL-12 p40/IL-B30 complex may be effected by an immobilized antibody to either polypeptide or sequence component or complementary binding partner, e.g., binding portion of a receptor.

A solubilized IL-12 p40/IL-B30 polypeptide or fragment of this invention can be used as an immunogen for the production of antisera or antibodies specific for binding. Purified antigen can be used to screen monoclonal antibodies or antigen-binding fragments, encompassing antigen binding fragments of natural antibodies, e.g., Fab, Fab', $F(ab)_2$, etc. Purified IL-12 p40/IL-B30 antigens can also be used as a reagent to detect antibodies generated in response to the presence of elevated levels of the cytokine complex, which may be diagnostic of an abnormal or specific physiological or disease condition. This invention contemplates antibodies raised against amino acid sequences encoded by nucleotide sequence shown in SEQ ID NO: 1, or fragments of proteins containing it. In particular, this invention contemplates antibodies having binding affinity to or being raised against specific domains, e.g., helices A, B, C, or D of the IL-B30, or the Ig domains of the IL-12 p40.

The present invention contemplates the isolation of additional closely related species variants. Southern and Northern blot analysis will establish that similar genetic entities exist in other mammals. It is likely that IL-B30s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species or polymorphic variants of them. In particular, the present invention provides useful probes for identifying additional homologous genetic entities in different species.

The isolated genes will allow transformation of cells lacking expression of an IL-B30, e.g., either species types or cells which lack corresponding proteins and exhibit negative background activity. This should allow analysis of the function of IL-B30 in comparison to untransformed control cells.

Dissection of critical structural elements which effect the various physiological functions mediated through these antigens is possible using standard techniques of modern molecular biology, particularly in comparing members of the related class. See, e.g., the homolog-scanning mutagenesis technique described in Cunningham et al., (1989) *Science* 243:1339–1336; and approaches used in O'Dowd et al., (1988) *J. Biol. Chem.* 263:15985–15992; and Lechleiter et al., (1990) *EMBO J.* 9:4381–4390.

Intracellular functions would probably involve receptor signaling. However, protein internalization may occur under certain circumstances, and interaction between intracellular components and cytokine may occur. Specific segments of interaction of IL-B30 with interacting components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of IL-B30 will be pursued. The controlling elements associated with the antigens should exhibit differential physiological, developmental, tissue specific, or other expression patterns. Upstream or downstream genetic regions, e.g., control elements, are of interest.

Structural studies of the IL-B30 antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various epitopes of the p40/IL-B30 proteins, including species, polymorphic, or allelic variants, and fragments thereof, both in their naturally occurring forms and in their recombinant forms. Additionally, antibodies can be raised to IL-B30s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective IL-B30s, or screened for agonistic or antagonistic activity, e.g., mediated through a receptor. Antibodies may be agonistic or antagonistic, e.g., by sterically blocking binding to a receptor. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying IL-B30 protein or its receptors. See, e.g., Chan, (ed. 1987) *Immunology: A Practical Guide*, Academic Press, Orlando, Fla.; Price and Newman, (eds. 1991) *Principles and Practice of Immunoassay*, Stockton Press, N.Y.; and Ngo, (ed. 1988) *Nonisotopic Immunoassay*, Plenum Press, N.Y. Cross absorptions or other tests will identify antibodies which exhibit various spectra of specificities, e.g., unique or shared species specificities.

Further, the antibodies, including antigen binding fragments, of this invention can be potent antagonists that bind to the antigen and inhibit functional binding, e.g., to a receptor which may elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner, (1962) *Specificity of Serological Reactions*, Dover Publications, New York; Williams et al., (1967) *Methods in Immunology and Immunochemistry*, vol. 1, Academic Press, New York; and Harlow and Lane, (1988) *Antibodies: A Laboratory Manual*, CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites et al., (eds.) *Basic and Clinical Immunology* (4th ed.), Lange Medical Publications, Los Altos, Calif., and references cited therein; Harlow and Lane, (1988) *Antibodies: A Laboratory Manual*, CSH Press; Goding, (1986) *Monoclonal Antibodies: Principles and Practice* (2d ed.), Academic Press, New York; and particularly in Kohler and Milstein, (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse et al., (1989) "Generation of a Large Combinatorial Library of the Immunoglobulin Repertoire in Phage Lambda," *Science* 246:1275–1281; and Ward et al., (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos.

3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore et al., U.S. Pat. No. 4,642,334; and Queen et al., (1989) *Proc. Natl. Acad. Sci. USA* 86:10029–10033.

The antibodies of this invention can also be used for affinity chromatography in isolating the protein. Columns can be prepared where the antibodies are linked to a solid support. See, e.g., Wilchek et al., (1984) *Meth. Enzymol.* 104:3–55. Conversely, protein can be used for depletion or cross absorptions to prepare selectively specific binding compositions.

Antibodies raised against each IL-B30 will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding both IL-12 p40 and IL-B30, e.g., from a natural source. Typically, it will be useful in isolating genes from a mammal, and similar procedures will be applied to isolate genes from other species, e.g., warm-blooded animals, such as birds and mammals. Cross hybridization will allow isolation of IL-12 p40 or IL-B30 from the same, e.g., polymorphic variants, or other species. A number of different approaches will be available to successfully isolate a suitable nucleic acid clone. Such genes allow construction of coexpression constructs or fusion constructs.

The purified protein or polypeptides are useful for generating antibodies by standard methods, as described above. Synthetic peptides or purified protein can be presented to an immune system to generate monoclonal or polyclonal antibodies. See, e.g., Coligan, (1991) *Current Protocols in Immunology* Wiley/Greene; and Harlow and Lane, (1989) *Antibodies: A Laboratory Manual*, Cold Spring Harbor Press.

For example, a specific binding composition could be used for screening of an expression library made from a cell line which expresses both IL-12 p40 and IL-B30. Screening of intracellular expression can be performed by various staining or immunofluorescence procedures. Binding compositions could be used to affinity purify or sort out cells expressing a surface fusion protein.

The peptide segments can also be used to select or identify appropriate oligonucleotides to screen a library. The genetic code can be used to select appropriate oligonucleotides useful as probes for screening. See, e.g., GenBank and SEQ ID NO: 1. In combination with polymerase chain reaction (PCR) techniques, synthetic oligonucleotides will be useful in selecting correct clones from a library. Complementary sequences will also be used as probes, primers, or antisense strands. Various fragments should be particularly useful, e.g., coupled with anchored vector or poly-A complementary PCR techniques or with complementary DNA of other peptides.

This invention contemplates use of isolated DNA or fragments to encode a biologically active complex of the corresponding IL-12 p40 and IL-B30 polypeptide, particularly lacking the portion coding the untranslated portions of the described sequences. In addition, this invention covers isolated or recombinant DNA which encodes a biologically active fusion protein or polypeptide and which is capable of hybridizing under appropriate conditions with the DNA sequences described herein. Said biologically active protein or polypeptide can be an intact antigen, or fragment, and have an amino acid sequence disclosed in, e.g., SEQ ID NO: 2, particularly a mature, secreted polypeptide. Further, this invention covers the use of isolated or recombinant DNA, or fragments thereof, which encode proteins which exhibit high identity to a secreted IL-12 p49/IL-B30 complex. The isolated DNA can have the respective regulatory sequences in the 5' and 3' flanks, e.g., promoters, enhancers, poly-A addition signals, and others. Alternatively, expression may be effected by operably linking a coding segment to a heterologous promoter, e.g., by inserting a promoter upstream from an endogenous gene. See, e.g., Treco et al., WO96/29411 or U.S. Ser. No. 08/406,030.

An "isolated" nucleic acid is a nucleic acid, e.g., an RNA, DNA, or a mixed polymer, which is substantially separated from other extraneous components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule, e.g., distinct from an isolated chromosome. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species or polymorphic variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides, e.g., 67, 73, 81, 89, 95, etc., including hundreds and/or thousands.

A DNA which codes for an IL-B30 protein will be particularly useful to identify genes, mRNA, and cDNA species which code for related or similar proteins, as well as DNAs which code for homologous proteins from different species. There will be homologs in other species, including primates, rodents, canines, felines, and birds. Various IL-B30 proteins should be homologous and are encompassed herein. However, even proteins that have a more distant evolutionary relationship to the antigen can readily be isolated under appropriate conditions using these sequences if they are sufficiently homologous. Primate IL-B30 proteins are of particular interest. Likewise with the IL-12 p40, which proteins are prime targets for the fusion constructs or combination compositions.

Recombinant clones derived from the genomic sequences, e.g., containing introns, will be useful for transgenic studies, including, e.g., transgenic cells and organisms, and for gene therapy. See, e.g., Goodnow, (1992) "Transgenic Animals" in Roitt (ed.) *Encyclopedia of Immunology*, Academic Press, San Diego, pp. 1502–1504; Travis, (1992) *Science* 256: 1392–1394; Kuhn et al., (1991) *Science* 254:707–710; Capecchi (1989) *Science* 244:1288; Robertson, (ed. 1987) *Teratocarcinomas and Embryonic Stem Cells: A Practical Approach*, IRL Press, Oxford; and Rosenberg, (1992) *J. Clinical Oncology* 10:180–199.

Substantial homology, e.g., identity, in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of IL-12 p40 and/or IL-B30, e.g., in SEQ ID NO: 1. Typically, selective hybridization will occur when there is at least about 55% identity over a stretch of at least about 30 nucleotides, preferably at least about 75% over a stretch of about 25 nucleotides, and most preferably at least about 90% over about 20 nucleotides. See, Kanehisa, (1984) *Nuc. Acids Res.* 12:203–213. The length of identity comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., more typically in excess of about 60 or 65° C., and preferably in excess of about 70° C. Stringent salt conditions will ordinarily be less than about 1000 mM, usually less than about 400 mM, typically less than about 250 mM, preferably less than about 150 mM, including about 100, 50, or even 20 mM. However, the combination of parameters is much more important than the measure of any single parameter. See, e.g., Wetmur and Davidson, (1968) *J. Mol. Biol.* 31:349–370. Hybridization under stringent conditions should give a background of at least 2-fold over background, preferably at least 3–5 or more.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman, (1981) *Adv. Appl. Math.* 2:482, by the homology alignment algorithm of Needleman and Wunsch, (1970) *J. Mol. Biol.* 48:443, by the search for similarity method of Pearson and Lipman, (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle, (1987) *J. Mol. Evol.* 35:351–360. The method used is similar to the method described by Higgins and Sharp, (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul et al., (1990) *J. Mol. Biol.* 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, (1989) *Proc. Natl. Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul, (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that they hybridize to each other under stringent conditions, as described below.

IL-B30 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making p40/IL-B30 Combinations; Mimetics

DNA which encodes the IL-12 p40 or IL-B30 or fragments thereof can be obtained by chemical synthesis, screening cDNA libraries, or screening genomic libraries prepared from a wide variety of cell lines or tissue samples. See, e.g., Okayama and Berg, (1982) *Mol. Cell. Biol.* 2:161–170; Gubler and Hoffman, (1983) *Gene* 25:263–269; and Glover, (ed. 1984) *DNA Cloning: A Practical Approach*, IRL Press, Oxford. Alternatively, the sequences provided herein provide useful PCR primers or allow synthetic or other preparation of suitable genes encoding an IL-12 p40 or IL-B30; including naturally occurring embodiments.

This DNA can be expressed in a wide variety of host cells for the synthesis of a full-length IL-12 p40 and IL-B30 or fragments which can, in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels et al., (1985 and Supplements) *Cloning Vectors: A Laboratory Manual*, Elsevier, N.Y.; and Rodriguez et al., (eds. 1988) *Vectors: A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See, e.g., Rodriguez et al., Chapter 10, pp. 205–236; Balbas and Bolivar, (1990) *Methods in Enzymology* 185:14–37; and Ausubel et al., (1993) *Current Protocols in Molecular Biology*, Greene and Wiley, NY. Coexpression of the two coding sequences is particularly of interest herein.

Representative examples of suitable expression vectors include pCDNA1; pCD, see Okayama et al., (1985) *Mol. Cell Biol.* 5:1136–1142; pMClneo Poly-A, see Thomas et al., (1987) *Cell* 51:503–512; and a baculovirus vector such as pAC 373 or pAC 610. See, e.g., Miller, (1988) *Ann. Rev. Microbiol.* 42:177–199.

It will often be desired to express an IL-12 p40 and/or IL-B30 polypeptide in a system which provides a specific or defined glycosylation pattern. See, e.g., Luckow and Summers, (1988) *Bio/Technology* 6:47–55; and Kaufman, (1990) *Meth. Enzymol.* 185:487–511.

The IL-12 p40 and/or IL-B30, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low, (1989) *Biochim. Biophys. Acta* 988:427–454; Tse et al., (1985) *Science* 230:1003–1008; and Brunner et al., (1991) *J. Cell Biol.* 114:1275–1283.

Now that the IL-12 p40 and IL-B30 have been characterized, fragments or derivatives thereof can be prepared by conventional processes for synthesizing peptides. These include processes such as are described in Stewart and Young, (1984) *Solid Phase Peptide Synthesis*, Pierce Chemical Co., Rockford, Ill.; Bodanszky and Bodanszky, (1984) *The Practice of Peptide Synthesis*, Springer-Verlag, New York; Bodanszky, (1984) *The Principles of Peptide Synthesis*, Springer-Verlag, New York; and Villafranca, (ed. 1991) *Techniques in Protein Chemistry II*, Academic Press, San Diego, Calif.

VIII. Uses

The present invention provides reagents which will find use in diagnostic applications as described elsewhere herein, e.g., in IL-12 p40/IL-B30 complex mediated conditions, or below in the description of kits for diagnosis. The gene may be useful in forensic sciences, e.g., to distinguish rodent from human, or as a marker to distinguish between different cells exhibiting differential expression or modification patterns. The provided compositions are useful reagents for, e.g., in vitro assays, scientific research, and the synthesis or manufacture of nucleic acids, polypeptides, or antibodies.

This invention also provides reagents with significant commercial and/or therapeutic potential. The IL-12 p40/IL- B30 complex (naturally occurring or recombinant), fragments thereof, and antibodies thereto, along with compounds identified as having binding affinity to the complex or individual components thereof, should be useful as reagents for teaching techniques of molecular biology, immunology, or physiology. Appropriate kits may be prepared with the reagents, e.g., in practical laboratory exercises in production or use of proteins, antibodies, cloning methods, histology, etc.

The reagents will also be useful in the treatment of conditions associated with abnormal physiology or development, including inflammatory conditions. They may be useful in vitro tests for presence or absence of interacting components, which may correlate with success of particular treatment strategies. In particular, modulation of physiology of various, e.g., hematopoietic or lymphoid, cells will be achieved by appropriate methods for treatment using the compositions provided herein. See, e.g., Thomson, (1994; ed.) *The Cytokine Handbook* (2d ed.) Academic Press, San Diego; Metcalf and Nicola, (1995) *The Hematopoietic Colony Stimulating Factors* Cambridge University Press; and Aggarwal and Gutterman, (1991) *Human Cytokines* Blackwell Pub.

Observations that the cytokine complex can induce IFNγ levels provides useful insight into therapeutic potential. In particular, IFNγ production results in enhanced cell mediated immunity. See, e.g., Paul, (1998) *Fundamental Immunology* (4th ed.) Raven Press, NY.; and Delves and Roitt (eds. 1998) *The Encyclopedia of Immunology* Academic Press (ISBN: 0122267656). Thus, enhancement of cellular responses will be useful in contexts to enhance anti-tumor activity, enhance vaccine responses (both humoral and cellular immunity), enhance anti-viral effects, and to antagonize allergic responses in certain windows of development. See, e.g, Rose and Mackay (eds. 1998) *The Autoimmune Diseases* (3d ed.) Acadmeic Press, San Diego; and Kay, (ed. 1997) *Allergy and Allergic Diseases* Blackwell Science, Malden Mass. Conversely, antagonists would be used to block or prevent such IFNγ enhancement, thereby reducing the strength or intensity of the cellular enhancement. Such may be useful in, e.g., autoimmune situations (such as multiple sclerosis or psoriasis) or chronic inflammatory conditions (such as rheumatoid arthritis or inflammatory bowel disease). See, e.g., Samter et al., (eds.) *Immunological Diseases* vols. 1 and 2, Little, Brown and Co. The initial results suggest that the role of the p40/IL-B30 is more critical in the maintenance of the chronic inflammatory condition. Thus, blockage may be effective after initial development of the condition.

With such therapeutic targets, the agonists or antagonists will be combined with existing therapeutics, e.g., with other modulators of inflammation. Thus, the agonists will often be combined, e.g., with IL-18, IL-12, radiation or chemotherapy treatments, vaccine adjuvants, and/or anti-viral therapeutics. Alternatively, the antagonists may be combined with TNFα antagonists, IL-12 antagonists, with IL-10, and/or steroids. Viral homologs of the cytokines might also be used.

For example, a disease or disorder associated with abnormal expression or abnormal signaling by an IL-12 p40/IL-B30 should be a likely target for an agonist or antagonist. The new cytokine should play a role in regulation or development of hematopoietic cells, e.g., lymphoid cells, which affect immunological responses, e.g., inflammation and/or autoimmune disorders. Alternatively, it may affect vascular physiology or development, or neuronal effects. Timing of administration of the therapeutic relative to initiation or maintenance of the condition may also be important. In particular, the cytokine complex should mediate, in various contexts, cytokine synthesis by the cells, proliferation, etc. Antagonists of IL-12 p40/IL-B30, such as mutein variants of a naturally occurring form or blocking antibodies, may provide a selective and powerful way to block immune responses, e.g., in situations as inflammatory or autoimmune responses. See also Samter et al., (eds.) *Immunological Diseases* vols. 1 and 2, Little, Brown and Co.

Particular targets for therapeutic application include, e.g., lung conditions, both asthma and fibrosis, in EAE models (which may be useful models for multiple sclerosis), diabetes, and gut inflammations. See, e.g., Barnes et al., (1998) *Mol. Med. Today* 4:452–458; Pauwels et al., (1998) *Clin. Exp. Allergy* Aug. 28 Suppl 3:1–5; Durham, (1998) *Clin. Exp. Allergy* Jun. 28 Suppl 2:11–16; Leung, (1997) *Pediatr. Res.* 42:559–568; Pretolani et al., (1997) *Res. Immunol.* 148:33–38; Lamkhioued et al., (1996) *Ann. NY Acad. Sci.* 796:203–208; Erb et al., (1996) *Immunol. Cell. Biol.* 74:206–208; and Anderson et al., (1994) *Trends Pharmacol. Sci.* 15:324–332 for asthma; Coker et al., (1998) *Eur. Respir. J.* 11:1218–1221; and Bienkowski et al., (1995) *Proc. Soc. Exp. Biol. Med.* 209:118–140 for lung fibrosis; Pearson and McDevitt, (1999) *Curr. Top. Microbiol. Immunol.* 238:79–122; Miller and Shevach, (1998) *Res. Immunol.* 149:753–759; Hoffman and Karpus, (1998) *Res. Immunol.* 149:790–794 (with discussion 846–847 and 855–860); Segal, (1998) *Res. Immunol.* 149:811–820 (with discussion 850–851 and 855–860); Liblau et al., (1997) *Immunol. Today* 18:599–604; Gold et al., (1997) *Crit. Rev. Immunol.* 17:507–510; Spack, (1997) *Crit. Rev. Immunol.* 17:529–536; and Leonard et al., (1997) *Crit. Rev. Immunol.* 17:545–553 for EAE models (for multiple sclerosis); Almawi et al., (1999) *J. Clin. Endocrinol. Metab.* 84:1497–1502; Rabinovitch et al., (1998) *Biochem. Pharmacol.* 55:1139–1149; and Rabinovitch, (1998) *Diabetes Metab. Rev.* 14:129–151 for diabetes; and Leach et al., (1999) *Toxicol. Pathol.* 27:123–133; Braun et al., (1999) *Curr. Opin. Rheumatol.* 11:68–74; Rugtveit et al., (1997) *Gastroenterology* 112:1493–1505; Strober et al., (1997) *Immunol. Today* 18:61–64; and Ford et al., (1996) *Semin. Pediatr. Surg.* 5:155–159 for gut/intestinal inflammatory conditions.

The p40/IL-B30 stimulation of memory activated cells results in phenotypic changes which include adhesion molecules. CD69L is highly expressed following stimulation with p40/IL-B30, and CD54 is dramatically decreased. These changes in expression of adhesion molecules may allow modulating memory cells to enter the T/DC cell rich region of primary and secondary lymph nodes, e.g., via high endothelial venules (HEV). The memory cells are also primed to become sensitive to IL-12 stimulation. Thus, rapid and high IFN production would quickly follow IL-12 induction by antigen. Thus p40/IL-B30 may accelerate an immune response by memory cells, either by increasing response rate, increasing memory cell numbers, or both. The p40/IL-B30 may have differential effects specific for memory cells, with lesser or no effect on naive cells. Conversely, in many chronic inflammatory conditions, e.g., rheumatoid arthritis, inflammatory bowel disease, psoriasis, etc., the active lesions are dependent upon memory $CD45Rb^{low}$ cells. As such, antagonists may effectively block the chronic phase of such an inflammatory condition.

Various abnormal conditions are known in each of the cell types shown to produce both IL-12 p40 and/or IL-B30 mRNA by Northern blot analysis. See Berkow (ed.) *The Merck Manual of Diagnosis and Therapy*, Merck & Co., Rahway, N.J.; Thorn et al., *Harrison's Principles of Internal Medicine*, McGraw-Hill, N.Y.; and Weatherall et al., (eds.) *Oxford Textbook of Medicine*, Oxford University Press, Oxford. Many other medical conditions and diseases involve activation by macrophages or monocytes, and many of these will be responsive to treatment by an agonist or antagonist provided herein. See, e.g., Stites and Terr (eds. 1991) *Basic and Clinical Immunology* Appleton and Lange, Norwalk, Connecticut; and Samter et al. (eds.), *Immunological Diseases* Little, Brown and Co. These problems should be susceptible to prevention or treatment using compositions provided herein.

The IL-12 p40/IL-B30 cytokine complex, antagonists, antibodies, etc., can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using IL-12 p40/IL-B30, fusion protein, or fragments thereof, can be performed to identify compounds having binding affinity to or other relevant biological effects on IL-12 p40/IL-B30 functions, including isolation of associated components. Subsequent biological assays can then be utilized to determine if a candidate compound has intrinsic stimulating activity and is therefore a blocker or antagonist in that it blocks the activity of the cytokine complex. Likewise, a compound having intrinsic stimulating activity can activate the signal pathway and is thus an agonist in that it simulates the activity of the cytokine complex. This invention further contemplates the therapeutic use of blocking antibodies to IL-12 p40, IL-B30, or the complex, as antagonists and of stimulatory antibodies as agonists. This approach should be particularly useful with other IL-12 p40 or IL-B30 species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al., (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous or long term administration. See, e.g., Langer, (1990) *Science* 249:1527–1533.

IL-12 p40, IL-B30, cytokine complex, fusion proteins, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by many methods well known in the art of pharmacy. See, e.g., Gilman et al., (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis et al., (eds. 1993) *Pharmaceutical Dosage Forms: Parenteral Medications*, Dekker, New York; Lieberman et al., (eds. 1990) *Pharmaceutical Dosage Forms: Tablets*, Dekker, New York; and Lieberman et al., (eds. 1990) *Pharmaceutical Dosage Forms: Disperse Systems*, Dekker, New York. The therapy of this invention may be combined with or used in association with other agents, e.g., other cytokines, including IL-6 or G-CSF, or their respective antagonists.

Both naturally occurring and recombinant forms of the IL-B30s of this invention are particularly useful in kits and assay methods which are capable of screening compounds for binding activity to the proteins. Several methods of automating assays have been developed in recent years so as to permit screening of tens of thousands of compounds in a short period. See, e.g., Fodor et al., (1991) *Science* 251: 767–773, which describes means for testing of binding affinity by a plurality of defined polymers synthesized on a solid substrate. The development of suitable assays can be greatly facilitated by the availability of large amounts of purified, soluble IL-12 p40/IL-B30 cytokine complex as provided by this invention.

Other methods can be used to determine the critical residues in IL-12 p40/IL-B30 complex-receptor interactions. Mutational analysis can be performed, e.g., see Somoza et al., (1993) *J. Exptl. Med.* 178:549–558, to determine specific residues critical in the interaction and/or signaling. PHD (Rost and Sander, (1994) *Proteins* 19:55–72) and DSC (King and Sternberg, (1996) *Protein Sci.* 5:2298–2310) can provide secondary structure predictions of α-helix (H), β-strand (E), or coil (L). Helices A and D are typically most important in receptor interaction, with the D helix the more important region.

For example, antagonists can normally be found once the antigen and/or receptor has been structurally defined, e.g., by tertiary structure data. Testing of potential interacting analogs is now possible upon the development of highly automated assay methods using a purified IL-12 p40/IL-B30 complex. In particular, new agonists and antagonists will be discovered by using screening techniques described herein. Of particular importance are compounds found to have a combined binding affinity for a spectrum of IL-12 p40/IL-B30 molecules, e.g., compounds which can serve as antagonists for species variants of the cytokine complex.

One method of drug screening utilizes eukaryotic or prokaryotic host cells which are stably transformed with recombinant DNA molecules expressing an IL-20 p40/IL-B30. Cells may be isolated which express an IL-12 p40/IL-B30 in isolation from other molecules. Such cells, either in viable or fixed form, can be used for standard binding partner binding assays. See also, Parce et al., (1989) *Science* 246:243–247; and Owicki et al., (1990) *Proc. Natl. Acad. Sci. USA* 87:4007–4011, which describe sensitive methods to detect cellular responses.

Another technique for drug screening involves an approach which provides high throughput screening for compounds having suitable binding affinity to an IL-12 p40/IL-B30 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor et al., (1991). Then all the pins are reacted with solubilized, unpurified or solubilized, purified p40/IL-B30, and washed. The next step involves detecting bound p40/IL-B30.

Rational drug design may also be based upon structural studies of the molecular shapes of the p40/IL-B30 and other effectors or analogs. Effectors may be other proteins which mediate other functions in response to binding, or other proteins which normally interact with p40/IL-B30, e.g., a receptor. One means for determining which sites interact with specific other proteins is a physical structure determination, e.g., x-ray crystallography or 2 dimensional NMR techniques. These will provide guidance as to which amino acid residues form molecular contact regions, as modeled, e.g., against other cytokine-receptor models. For a detailed description of protein structural determination, see, e.g., Blundell and Johnson, (1976) *Protein Crystallography*, Academic Press, New York.

IX. Kits

This invention also contemplates use of p40/IL-B30 proteins, fragments thereof, peptides, and their fusion products in a variety of diagnostic kits and methods for detecting the presence of another p40/IL-B30 or binding partner. Typically the kit will have a compartment containing either a defined p40, p40/IL-B30, or IL-B30 peptide or gene segment or a reagent which recognizes one or the other, e.g., p40/IL-B30 fusion fragments or antibodies.

A kit for determining the binding affinity of a test compound to an IL-12 p40/IL-B30 would typically comprise a test compound; a labeled compound, for example a binding partner or antibody having known binding affinity for p40/IL-B30; a source of p40/IL-B30 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the p40/IL-B30 signaling pathway. The availability of recombinant IL-12 p40/IL-B30 fusion polypeptides also provide well defined standards for calibrating such assays.

A preferred kit for determining the concentration of, e.g., a p40/IL-B30 in a sample would typically comprise a labeled compound, e.g., binding partner or antibody, having known binding affinity for the antigen, a source of cytokine (naturally occurring or recombinant) and a means for separating the bound from free labeled compound, e.g., a solid phase for immobilizing the p40/IL-B30. Compartments containing reagents, and instructions, will normally be provided.

Antibodies, including antigen binding fragments, specific for the p40/IL-B30 or fragments are useful in diagnostic applications to detect the presence of elevated levels of p40, IL-B30, p40/IL-B30, and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis et al., (1980) *Meth Enzymol.* 70:1–525; Harlow and Lane, (1980) *Antibodies: A Laboratory Manual*, CSH Press, NY; and Coligan et al., (eds. 1993) *Current Protocols in Immunology*, Greene and Wiley, NY.

Anti-idiotypic antibodies may have similar use to diagnose presence of antibodies against a p40/IL-B30, as such may be diagnostic of various abnormal states. For example, overproduction of p40/IL-B30 may result in production of various immunological reactions which may be diagnostic of abnormal physiological states, particularly in proliferative cell conditions such as cancer or abnormal activation or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled p40/IL-B30 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In many of these assays, the binding partner, test compound, p40/IL-B30, or antibodies thereto can be labeled either directly or indirectly. Possibilities for direct labeling include label groups: radiolabels such as $^{125}$I, enzymes such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free p40/IL-B30, or alternatively the bound from the free test compound. The p40/IL-B30 can be immobilized on various matrixes followed by washing. Suitable matrixes include plastic such as an ELISA plate, filters, and beads.

See, e.g., Coligan et al., (eds. 1993) *Current Protocols in Immunology*, Vol. 1, Chapter 2, Greene and Wiley, NY. Other suitable separation techniques include, without limitation, the fluorescein antibody magnetizable particle method described in Rattle et al., (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a p40/IL-B30. These sequences can be used as probes for detecting levels of the p40 or IL-B30 messages in samples from patients suspected of having an abnormal condition, e.g., inflammatory or autoimmune. Since the cytokine may be a marker or mediator for activation, it may be useful to determine the numbers of activated cells to determine, e.g., when additional therapy may be called for, e.g., in a preventative fashion before the effects become and progress to significance. The preparation of both RNA and DNA nucleotide sequences, the labeling of the sequences, and the preferred size of the sequences has received ample description and discussion in the literature. See, e.g., Langer-Safer et al., (1982) *Proc. Natl. Acad. Sci.* 79:4381–4385; Caskey, (1987) *Science* 236:962–967; and Wilchek et al., (1988) *Anal. Biochem.* 171:1–32.

Diagnostic kits which also test for the qualitative or quantitative expression of other molecules are also contemplated. Diagnosis or prognosis may depend on the combination of multiple indications used as markers. Thus, kits may test for combinations of markers. See, e.g., Viallet et al., (1989) *Progress in Growth Factor Res.* 1:89–97. Other kits may be used to evaluate other cell subsets.

X. Isolating a p40/IL-B30 Receptor

Having isolated a ligand of a specific ligand-receptor interaction, methods exist for isolating the receptor. See, Gearing et al., (1989) *EMBO J.* 8:3667–3676. For example, means to label the IL-B30 cytokine without interfering with the binding to its receptor can be determined. For example, an affinity label can be fused to either the amino- or carboxyl-terminus of the ligand. Such label may be a FLAG epitope tag, or, e.g., an Ig or Fc domain. An expression library can be screened for specific binding of the cytokine, e.g., by cell sorting, or other screening to detect subpopulations which express such a binding component. See, e.g., Ho et al., (1993) *Proc. Natl. Acad. Sci. USA* 90:11267–11271; and Liu et al., (1994) *J. Immunol.* 152: 1821–29. Alternatively, a panning method may be used. See, e.g., Seed and Aruffo, (1987) *Proc. Natl. Acad. Sci. USA* 84:3365–3369.

Protein cross-linking techniques with label can be applied to isolate binding partners of the p40/IL-B30 cytokine complex. This would allow identification of proteins which specifically interact with the cytokine, e.g., in a ligand-receptor like manner.

Early experiments will be performed to determine whether the known IL-6 or G-CSF receptor components are involved in response(s) to p40/IL-B30. It is also quite possible that these functional receptor complexes may share many or all components with a p40/IL-B30 receptor complex, either a specific receptor subunit or an accessory receptor subunit.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

I. General Methods

Many of the standard methods below are described or referenced, e.g., in Maniatis et al., (1982) *Molecular Cloning, A Laboratory Manual* Cold Spring Harbor Laboratory, Cold Spring Harbor Press, NY; Sambrook et al., (1989) *Molecular Cloning: A Laboratory Manual* (2d ed.) Vols. 1–3, CSH Press, NY; Ausubel et al., *Biology* Greene Publishing Associates, Brooklyn, N.Y.; Ausubel et al., (1987 and Supplements) *Current Protocols in Molecular Biology* Wiley/Greene, NY; Innis et al., (eds. 1990) *PCR Protocols: A Guide to Methods and Applications* Academic Press, NY; Bonifacino et al., *Current Protocols in Cell Biology* Wiley, NY; and Doyle et al., *Cell and Tissue Culture: Laboratory Protocols* Wiley, NY. Methods for protein purification include such methods as ammonium sulfate precipitation, column chromatography, electrophoresis, centrifugation, crystallization, and others. See, e.g., Ausubel et al., (1987 and periodic supplements); Deutscher, (1990) "Guide to Protein Purification," *Methods in Enzymology* vol. 182, and other volumes in this series; Coligan et al., (1995 and supplements) *Current Protocols in Protein Science* John Wiley and Sons, New York, N.Y.; Matsudaira, (ed. 1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1990) "Purification of Recombinant Proteins with Metal Chelate Absorbent" in Setlow (ed.) *Genetic Engineering, Principle and Methods* 12:87–98, Plenum Press, NY; and Crowe et al., (1992) *QIAexpress: The High Level Expression & Protein Purification System* QUIAGEN, Inc., Chatsworth, Calif.

Computer sequence analysis is performed, e.g., using available software programs, including those from the University of Wisconsin Genetics Computer Group (GCG), Madison, Wis., the NCBI at NIH, and GenBank, NCBI, EMBO, and other sources of public sequence. Other analysis sources include, e.g., RASMOL program, see Bazan et al., (1996) *Nature* 379:591; Lodi et al., (1994) *Science* 263: 1762–1766; Sayle and Milner-White, (1995) *TIBS* 20:374–376; and Gronenberg et al., (1991) *Protein Engineering* 4:263–269; and DSC, see King and Sternberg, (1996) *Protein Sci.* 5:2298–2310. See, also, Wilkins et al., (eds. 1997) *Proteome Research: New Frontiers in Functional Genomics* Springer-Verlag, NY; Salzberg et al., (eds. 1998) *Computational Methods in Molecular Biology* Elsevier, NY; and Birren et al., (eds. 1997) *Genome Analysis: A Laboratory Manual* Cold Spring Harbor Press, Cold Spring Harbor, N.Y.

Standard immunological techniques are described, e.g., in Hertzenberg et al., (eds. 1996) *Weir's Handbook of Experimental Immunology* vols. 1–4, Blackwell Science; Coligan, (1991 and updates) *Current Protocols in Immunology* Wiley/Greene, NY; and *Methods in Enzymology* vols. 70, 73, 74, 84, 92, 93, 108, 116, 121, 132, 150, 162, and 163. Cytokine assays are described, e.g., in Thomson, (ed. 1994) *The Cytokine Handbook* (2d ed.) Academic Press, San Diego; Metcalf and Nicola, (1995) *The Hematopoietic Colony Stimulating Factors* Cambridge University Press; and Aggarwal and Gutterman, (1991) *Human Cytokines* Blackwell Pub.

Assays for vascular biological activities are well known in the art. They will cover angiogenic and angiostatic activities in tumor, or other tissues, e.g., arterial smooth muscle proliferation (see, e.g., Koyoma et al., (1996) *Cell* 87:1069–1078), monocyte adhesion to vascular epithelium (see McEvoy et al., (1997) *J. Exp. Med.* 185:2069–2077), etc. See also Ross, (1993) *Nature* 362:801–809; Rekhter and Gordon, (1995) *Am. J. Pathol.* 147:668–677; Thyberg et al., (1990) *Atherosclerosis* 10:966–990; and Gumbiner, (1996) *Cell* 84:345–357.

Assays for neural cell biological activities are described, e.g., in Wouterlood, (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed et al., (1990) *Flow Cytometry and Sorting* Wiley-Liss, Inc., New York, N.Y.; Shapiro, (1988) *Practical Flow Cytometry* Liss, New York, N.Y.; and Robinson et al., (1993) *Handbook of Flow Cytometry Methods* Wiley-Liss, New York, N.Y.

II. Cloning of Human p40 and/or IL-B30

The IL-12 p40 sequences are available from various sequence databases, as described above. The sequence of the IL-B30 gene is provided in Table 1. The sequence is derived from a genomic human sequence.

These sequences allow preparation of PCR primers, or probes, to determine cellular distribution of the genes. The sequences allow isolation of genomic DNA which encode the messages.

Using the probe or PCR primers, various tissues or cell types are probed to determine cellular distribution. PCR products are cloned using, e.g., a TA cloning kit (Invitrogen). The resulting cDNA plasmids are sequenced from both termini on an automated sequencer (Applied Biosystems).

III. Cellular Expression of p40 and IL-B30

An appropriate probe or primers specific for cDNA encoding the respective genes are prepared. Typically, the probe is labeled, e.g., by random priming. Coordinate expression of both subunits is most important where the p40/IL-B30 complex is of interest.

IV. Purification of p40/IL-B30 Protein

Multiple transfected cell lines are screened for one which expresses the cytokine or complex at a high level compared with other cells. Alternatively, a combination recombinant construct can be made. Various cell lines are screened and selected for their favorable properties in handling. Individual isolation of the respective subunits and combination thereafter may result in some dimer formation. Natural IL-B30 can be isolated from natural sources, or by expression from a transformed cell using an appropriate expression vector. Adenovirus constructs can also be used for production/expression.

Purification of the expressed subunits or complex is achieved by standard procedures, or may be combined with engineered means for effective purification at high efficiency from cell lysates or supernatants. In particular, fusion of p40 to IL-B30, with or without appropriate linker, can result in high efficiency methods for processing or purification. FLAG or $His_6$ segments can be used for such purification features. Alternatively, affinity chromatography may be used with specific antibodies, see below.

Protein is produced in coli, insect cell, or mammalian expression systems, as desired.

V. Preparation of Antibodies Specific for p40/IL-B30

Synthetic peptides or purified protein are presented to an immune system to generate monoclonal or polyclonal antibodies. See, e.g., Coligan, (1991) *Current Protocols in Immunology* Wiley/Greene; and Harlow and Lane, (1989) *Antibodies: A Laboratory Manual* Cold Spring Harbor Press. Immunoselection or depletion methods can be applied to ensure that resulting antibodies are specific for antigenic determinants presented by the complex of polypeptides, distinct from those presented by the individual components themselves. Polyclonal serum, or hybridomas may be prepared. In appropriate situations, the binding reagent is either labeled as described above, e.g., fluorescence or otherwise, or immobilized to a substrate for panning methods. Immunoselection, immunodepletion, and related techniques are available to prepare selective reagents, as desired, e.g., for the complex between the two subunits.

VI. IL-12 p40 and IL-B30 Coprecipitate

A mouse IL-12 p40-Ig fusion construct was prepared in an expression vector. The Ig domain binds to Protein A, and can precipitate that polypeptide. An IL-B30Etag (epitope tagged with a FLAG motif at the N terminus) construct was also prepared, which polypeptide is immunoprecipitable with the M2 antibody. The expression constructs were transfected into 293 T cells, either with the IL-12 p40-Ig construct alone, the IL-B30Etag construct alone, or both together. Cells were labeled with $^{35}S$ methionine. With the IL-12 p40 construct alone, no soluble protein was detected in the cell supernatant using Protein A. Likewise, with the FLAG-IL-B30 construct, no soluble protein was detected in the cell supernatant using the M2 antibody. However, with cotransfection of the two expression constructs, the cell supernatant produced a soluble complex which was precipitable with either the Protein A reagent or the M2 antibody. PAGE analysis of the complex revealed that the Protein A precipitated complex was made of polypeptides corresponding to the two expected polypeptides IL-12 p40-Ig fusion and the FLAG-IL-B30 polypeptides. Correspondingly, the complex precipitated with the M2 antibody was made up of the FLAG-IL-B30 polypeptide and the IL-12 p40-Ig fusion protein.

Similar experiments with a human IL-12 p40 expression construct and a human FLAG-IL-B30 construct provided the expected results. Transfection with the FLAG-IL-B30 construct resulted in no significant soluble protein. Cotransfection of both expression vectors into primate cells resulted in effective secretion of a complex which was immunoprecipitable with the M2 antibody. PAGE analysis of the resulting complex confirmed that the complex was made up of the FLAG-IL-B30 polypeptide and the IL-12 p40 polypeptide.

VII. Receptor Identification

The IL-12 receptor is made up of the IL-12 receptor subunits β1 and β2. A fusion construct of p40/IL-B30 binds to cells expressing the receptor subunit β1.

A homodimer of the IL-12 p40 subunits can block the binding of IL-12 to the mouse subunit β1, but not to the subunit β2. The p40 subunit is a component of the p40/IL-B30 complex, so it was tested whether the IL-12 receptor subunit β1 could be a component of the receptor for a fusion construct of p40/IL-B30. Antibodies to the IL-12 receptor subunit β1 block binding of the fusion construct to cells expressing the receptor subunit β1. Antibodies against the p40/p70 complex, mainly recognizing the p40 subunit, can block the effect of the p40/IL-B30 composition, suggesting that the p40 component is important in receptor interaction. These observations suggest that the receptor subunit β1 binds to the p40/IL-B30 fusion construct. Similar experiments testing involvement of the common gp130 subunit shared among related receptors suggest that the gp130 is not a relevant subunit of the receptor for p40/IL-B30.

Having identified one subunit of the receptor, expression cloning efforts have been initiated. Cells expressing this one subunit but showing no binding will be used to expression clone an additional subunit. Other receptor subunit β2 homologs are being screened. Alternatively, libraries from appropriate cells can be used in standard expression cloning methods.

VIII. Evaluation of Breadth of Biological Functions

Biological activities of p40/IL-B30 complex are tested based, e.g., on the sequence and structural homology between IL-B30 and IL-6 and G-CSF. Initially, assays that had shown biological activities of IL-6 or G-CSF were examined. Assays were performed on either recombinant complex or fusion construct. Fusion construct consisted of a construct with the IL-12 p40 signal sequence linked to an N terminal FLAG epitope fused to the mature IL-12 p40 sequence fused to a ser/gly rich linker sequence of appropriate length fused to the mature sequence of IL-B30. This construct both expresses well, is secreted, and the epitope tag allows both purification and localization. Both mouse and human sequence forms were generated. Adenovirus expression constructs of both separate polypeptides and fusion proteins are also made available.

Target cell types include lympoid, myeloid, mast, pre-B, pre-T, and fibroblast-endothelial cell types. For example, macrophage/monocyte cells will be evaluated for cell surface marker changes, e.g., MHC class II, B7, CD40, and related families; cytokine and chemokine production; and antigen presentation capacity. CD4+ T cells, both naive CD45Rb$^{hi}$ and memory CD45Rb$^{low}$ T cells, will be assayed, e.g., for growth and activation markers, and for effector functions, e.g., cytokine and chemokine production. Cytotoxic CD4+, CD8+ and NK cells will be evaluated for effects on generation and function. Effects on antibody production will be tested, e.g., on splenic and MLN B cells. Dendritic cells will be evaluated for generation, maturation, and function, including factor production. Apoptosis assays are also being developed.

Long term bone marrow cultures will be tested for effects on modulation of stroma cells and stem cell generation and differentiation (Dexter cultures), for modulation of stromal cells and B cell progenitor generation and differentiation (Whitlock-Witte cultures), and for evaluation of potential to regulate primitive myeloid and B lymphoid populations.

A. Effects on Proliferation of Cells

The effect on proliferation of various cell types are evaluated with various concentrations of cytokine. A dose response analysis is performed, in combinations with the related cytokines IL-6, G-CSF, etc. A cytosensor machine may be used, which detects cell metabolism and growth (Molecular Devices, Sunnyvale, Calif.).

Human p40/IL-B30 fusion protein enhanced proliferation of human PHA blasts stimulated with anti-CD3 or both anti-CD3 and anti-CD28. The anti-CD3 stimulation appears to be essential. Human p40/IL-B30 fusion protein also enhanced proliferation of activated Th1 or Th2 cell clones, but not resting Th1 or Th2 cell clones.

Either mouse or human fusion protein worked on mouse target cells. Fusion protein supported proliferation of CD4+ CD45Rb$^{low}$ CD62L$^{low}$ CD44$^{hi}$ cells (memory/activated T cells) when stimulated with anti-CD3. Stimulation by fusion protein is not enhanced by anti-CD28 costimulation. This is not grossly dependent on presence of IL-2. This suggests that p40/IL-B30 may be an important factor for expanding a population of cells with a memory phenotype and/or generating or maintaining immunologic memory. This cytokine seems to selectively support activated memory cells with a Th1 phenotype, e.g., cells which produce IFNγ, but no IL-4 or IL-5.

B. Effects on Differentiation of Naive T Cells

Human cord blood cells were collected and naive CD4+ T cells were isolated. These were cultured, e.g., for 2 weeks, in the presence of anti-CD3 and IL-2 and with irradiated fibroblasts expressing CD32, CD58, and CD80, thereby activating and proliferating T cells. The T cell culture was evaluated for effects of various cytokines on proliferation or differentiation. Individual cells were evaluated for cytokine production by FACS analysis. The p40/IL-B30 fusion protein supported the proliferation and differentiation of T cells producing IFNγ and no IL-4, a cytokine expression profile characteristic of Th1 cells.

C. Effects on the Expression of Cell Surface Molecules

Monocytes are purified by negative selection from peripheral blood mononuclear cells of normal healthy donors. Briefly, 3×10$^8$ ficoll banded mononuclear cells are incubated on ice with a cocktail of monoclonal antibodies (Becton-Dickinson; Mountain View, Calif.) consisting, e.g., of 200 μl of αCD2 (Leu-5A), 200 μl of αCD3 (Leu-4), 100 μl of αCD8 (Leu 2a), 100 μl of αCD19 (Leu-12), 100 μl of αCD20 (Leu-16), 100 μl of αCD56 (Leu-19), 100 μl of αCD67 (IOM 67; Immunotech, Westbrook, Me.), and anti-glycophorin antibody (10F7MN, ATCC, Rockville, Md.). Antibody bound cells are washed and then incubated with sheep anti-mouse IgG coupled magnetic beads (Dynal, Oslo, Norway) at a bead to cell ratio of 20:1. Antibody bound cells are separated from monocytes by application of a magnetic field. Subsequently, human monocytes are cultured in Yssel's medium (Gemini Bioproducts, Calabasas, Calif.) containing 1% human AB serum in the absence or presence of IL-B30, IL-6, G-CSF or combinations.

Analyses of the expression of cell surface molecules can be performed by direct immunofluorescence. For example, 2×10$^5$ purified human monocytes are incubated in phosphate buffered saline (PBS) containing 1% human serum on ice for 20 minutes. Cells are pelleted at 200×g. Cells are resuspended in 20 ml PE or FITC labeled mAb. Following an additional 20 minute incubation on ice, cells are washed in PBS containing 1% human serum followed by two washes in PBS alone. Cells are fixed in PBS containing 1% paraformaldehyde and analyzed on FACScan flow cytometer (Becton Dickinson; Mountain View, Calif.). Exemplary mAbs are used, e.g.: CD11b (anti-mac1), CD11c (a gp150/95), CD14 (Leu-M3), CD54 (Leu 54), CD80 (anti-BB 1/B7), HLA-DR (L243) from Becton-Dickinson and CD86 (FUN 1; Pharmingen), CD64 (32.2; Medarex), CD40 (mAb89; Schering-Plough France).

D. Effects on Cytokine Production by Human Cells

Human monocytes are isolated as described and cultured in Yssel's medium (Gemini Bioproducts, Calabasas, Calif.) containing 1% human AB serum in the absence or presence of IL-B30 (1/100 dilution baculovirus expressed material). In addition, monocytes are stimulated with LPS (*E. coli* 0127:B8 Difco) in the absence or presence of IL-B30 and the concentration of cytokines (IL-1β, IL-6, TNFα, GM-CSF, and IL-10) in the cell culture supernatant determined by ELISA.

For intracytoplasmic staining for cytokines, monocytes are cultured (1 million/ml) in Yssel's medium in the absence or presence of IL-B30 and LPS (*E. coli* 0127:B8 Difco) and 10 mg/ml Brefeldin A (Epicentre technologies Madison Wis.) for 12 hrs. Cells are washed in PBS and incubated in 2% formaldehyde/PBS solution for 20 minutes at RT. Subsequently cells are washed, resuspended in permeabilization buffer (0.5% saponin (Sigma) in PBS/BSA (0.5%)/Azide (1 mM) and incubated for 20 minutes at RT. Cells ($2 \times 10^5$) are centrifuged and resuspended in 20 ml directly conjugated anti-cytokine mAbs diluted 1:10 in permeabilization buffer for 20 minutes at RT. The following antibodies can be used: IL-1α-PE (364-3B3-14); IL-6-PE (MQ2-13A5); TNFα-PE (MAb11); GM-CSF-PE (BVD2-21C11); and IL-12-PE (C11.5.14; Pharmingen San Diego, Calif.). Subsequently, cells are washed twice in permeabilization buffer and once in PBS/BSA/Azide and analyzed on FACScan flow cytometer (Becton Dickinson; Mountain View, Calif.).

Human PHA blasts produced IFNγ in response to contacting with human p40/IL-B30 fusion construct. The effects were synergistic with IL-2. Fusion product enhanced IFNγ production by activated, but not resting T cells, resting Th1 cell clones, or resting Th2 cell clones.

E. Effects on Proliferation of Human Peripheral Blood Mononuclear Cells (PBMC)

Total PBMC are isolated from buffy coats of normal healthy donors by centrifugation through ficoll-hypaque as described (Boyum et al.). PBMC are cultured in 200 μl Yssel's medium (Gemini Bioproducts, Calabasas, Calif.) containing 1% human AB serum in 96 well plates (Falcon, Becton-Dickinson, NJ) in the absence or presence of IL-B30. Cells are cultured in medium alone or in combination with 100 U/ml IL-2 (R&D Systems) for 120 hours. 3H-Thymidine (0.1 mCi) is added during the last six hours of culture and 3H-Thymidine incorporation determined by liquid scintillation counting.

The native, recombinant, and fusion proteins would be tested for agonist and antagonist activity in many other biological assay systems, e.g., on T-cells, B-cells, NK, macrophages, dendritic cells, hematopoietic progenitors, etc. Because of the IL-6 and G-CSF structural relationship, assays related to those activities should be analyzed p40/IL-B30 is evaluated for agonist or antagonist activity on transfected cells expressing IL-6 or G-CSF receptor and controls. See, e.g., Ho et al., (1993) *Proc. Natl. Acad. Sci. USA* 90, 11267–11271; Ho et al., (1995) *Mol. Cell. Biol.* 15:5043–5053; and Liu et al., (1994). *J. Immunol.* 152: 1821–1829.

p40/IL-B30 is evaluated for effect in macrophage/dendritic cell activation and antigen presentation assays, T cell cytokine production and proliferation in response to antigen or allogenic stimulus. See, e.g., de Waal Malefyt et al., (1991) *J. Exp. Med.* 174:1209–1220; de Waal Malefyt et al., (1991) *J. Exp. Med.* 174:915–924; Fiorentino et al., (1991) *J. Immunol.* 147, 3815–3822; Fiorentino et al., (1991) *J. Immunol.* 146:3444–3451; and Groux et al., (1996) *J. Exp. Med.* 184:19–29.

p40/IL-B30 will also be evaluated for effects on NK cell stimulation. Assays may be based, e.g., on Hsu et al., (1992) *Internat. Immunol.* 4:563–569; and Schwarz et al., (1994) *J. Immunother.* 16:95–104.

B cell growth and differentiation effects will be analyzed, e.g., by the methodology described, e.g., in Defrance et al., (1992). *J. Exp. Med.* 175:671–682; Rousset et al., (1992) *Proc. Natl. Acad. Sci. USA* 89:1890–1893; including IgG2 and IgA2 switch factor assays.

IX. Generation and Analysis of Genetically Altered Animals

Transgenic mice can be generated by standard methods. Such animals are useful to determine the effects of overexpression of the genes, in specific tissues, or completely throughout the organism. Such may provide interesting insight into development of the animal or particular tissues in various stages. Moreover, the effect on various responses to biological stress can be evaluated. See, e.g., Hogan et al., (1995) *Manipulating the Mouse Embryo: A Laboratory Manual* (2d ed.) Cold Spring Harbor Laboratory Press.

Adenovirus techniques are available for expression of the genes in various cells and organs. See, e.g., Hitt et al., (1997) *Adv. Pharmacol.* 40:137–195; and literature from Quantum Biotechnologies, Montreal, Canada. Animals may be useful to determine the effects of the genes on various developmental or physiologically functional animal systems.

A 0.5 kb cDNA encoding for IL-B30 was cloned as an EcoRI fragment into an expression vector containing the CMV enhancer β-actin promoter and the rabbit β-globin polyadenylation signal, previously described by Niwa et al., (1991) *Gene* 108:193–200. Separation of the transgene from vector sequence was accomplished by zonal sucrose gradient centrifugation as described by Mann et al., (1993) "Factor Influencing Production Frequency of Transgenic Mice", *Methods in Enzymology* 225: 771–781. Fractions containing the transgene were pooled, microcentrifugation through Microcon-100 filters and washed 5 times with microinjection buffer (5 mM Tris-HCl, pH 7.4, 5 mM NaCl, 0.1 mM EDTA).

The transgene was resuspended in microinjection buffer (5 mM Tris-HCl, pH 7.4, 5 mM NaCl, 0.1 mM EDTA) to a final concentration of 1–5 ng/ml, microinjected into ([C57BL/6J×DBA/2]$F_1$; The Jackson Laboratory) eggs, which were then transferred into oviducts of ICR (Sprague-Dawley) foster mothers, according to published procedures by Hogan et al., (1994) *Manipulation of the Mouse Embryo*, Plainview, N.Y., Cold Spring Harbor Laboratory Press. By 10 days of life, a piece of tail from the resulting animals was clipped for DNA analysis. Identification of transgenic founders was carried out by polymerase chain reaction (PCR) analysis, as previously described by Lira et al., (1990) *Proc. Natl. Acad. Sci. USA*, 87: 7215–7219. Identification of the IL-B30 transgenic mice was accomplished by amplification of mouse tail DNA. As an internal control for the amplification reaction primers for the endogenous LDL gene were used. The primers amplify a 200 bp segment of the IL-B30 transgene and 397 bp segment of the LDL gene. PCR conditions were: 95° C., 30 seconds; 60° C., 30 seconds; 72° C., 60 seconds for 30 cycles. Transgenic animals were kept under pathogen-free conditions.

Analysis of IL-B30 Transgenic Mice

RNA was extracted from tissues using RNA STAT-60, following specifications from the manufacturer (TEL-TEST, Inc. Friendswood, Tex.). Total RNA (20 mg) was denatured and blotted onto Biotrans membrane (ICN Biomedicals, Costa Mesa, Calif.). Transgene expression was assessed by hybridization to randomly labeled L-30 cDNA (Stratagene, La Jolla, Calif.). Acute phase liver gene expression was assessed by hybridizing total RNA with randomly labeled PCR segments of the murine hemopexin gene, of the murine alpha-1-acid glycoprotein, and of the murine haptoglobin gene.

ELISA kits were purchased from commercial sources and run according to the manufacturer's instructions. ELISA kits for murine IL-2 (sensitivity<3 pg/ml), murine IL-1b (sensitivity<3 pg/ml), murine IFN-gamma (sensitivity<2 pg/ml) and murine TNF-alpha (sensitivity<5.1 pg/ml) were purchased from R & D systems (Minneapolis, Minn.). Murine IL-6 ELISA kits (sensitivity<8 pg/ml) were purchased from Biosource International (Camarillo, Calif.). Murine IL-1α ELISA kits (sensitivity<6 pg/ml) were purchased from Endogen (Cambridge, Mass.).

ELISA assays for serum immunoglobulin levels were run using antibody pairs purchased from PharMingen (San Diego, Calif.) following the manufacturer's guidelines. Anti-mouse IgM (clone 11/41), anti-mouse IgA (clone R5-140), anti-mouse IgG1 (clone A85-3), anti-mouse IgG2a (clone R11-89) and anti-mouse IgG2b (clone R9-91) were used as capture antibodies. Purified mouse IgM (clone G155-228), IgA (clone M18-254), IgG1 (clone 107.3), IgG2a (clone G155-178) and IgG2b (clone 49.2) were used to generate standard curves. Biotin anti-mouse IgM (clone R6-60.2), biotin anti-mouse IgA (clone R5-140), biotin anti-mouse IgG1 (clone A85-1), biotin anti-mouse IgG2a (clone R19-15) and biotin anti-mouse IgG2b (clone R12-3) were used as detection antibodies.

Levels of IGF-1 in mouse serum were determined using a commercially available radioimmunoassay for human IGF-1 that also recognizes murine IGF-1 after serum samples were acid-ethanol extracted according to instructions provided by the manufacturer (Nichols Institute, San Juan Capistrano, Calif.).

After sacrifice, tissues were either snap frozen with freezing media for cryosection, or fixed by immersion in 10% phosphate-buffered formalin. Formalin fixed tissues were routinely processed at 5 mm, and were stained with hematoxylin and eosin (H & E). For immunostaining, snap frozen sections were fixed with acetone and air dried.

Blood samples were collected from the infra-orbital sinus into sterile, evacuated tubes with added EDTA (Vacutainer Systems; Becton Dickinson, Rutherford, N.J.). Hematologic values were determined with an automated system (Abbot Cell-Dyn 3500, Abbot Park, Ill.). Platelet counts were performed manually when the instrument was unable to provide accurate platelet counts due to excessive clumping or excessively large platelets. Blood smears were stained with Modified Wright-Giemsa stain (Hema-Tek Stain Pack, Bayer Corp., Elkhart, Ind.) using an automated stainer (Bayer Hema-Tek 2000, Elkhart, Ind.) and examined manually for immature cells and platelet, red blood cell, and white blood cell morphology.

Bone Marrow Transfer

The femur and tibia were cleaned of muscle and bone marrow was expelled by flushing the bone with PBS. Bone marrow cells were washed once, and injected i.v. into recipient mice which had been lethally irradiated (1000 RAD).

Phenotype of IL-B30 Transgenic Mice

To analyze the biological function of IL-B30, the gene was expressed under the control of the CMV enhancer/actin promoter, described by Niwa et al., (1991) Gene 108: 193–200, in transgenic mice. This enhancer/promoter cassette directs high levels of transgene expression primarily to skeletal muscle and pancreas, but the transgene can be expressed in virtually all organs and cells. See Lira et al., (1990) Proc. Natl. Acad. Sci. USA 87: 7215–7219.

IL-B30 transgenic mice were runted compared to control littermates. The rate of body weight gain in IL-B30 transgenic mice varied widely but was clearly lower than that found in control littermates. Northern blot analysis, of RNA extracted from either muscle or skin of IL-B30 transgenic mice and control littermates hybridized to IL-B30 cDNA, revealed that IL-B30 mRNA was detected in both muscle and skin of all IL-B30 transgenic mice, whereas no IL-B30 mRNA was detected in control littermates. This demonstrated that stunted growth was always associated with expression of IL-B30.

Of the IL-B30 transgenic mice obtained, 25% survived to adulthood and were affected by expression of IL-B30 as exhibited by impaired growth, a swollen abdomen, ruffled fur, infertility and sudden death. Thus, transgenic expression of IL-B30 caused a phenotype that prevented the generation of IL-B30 transgenic progeny. The results presented here are derived from the preliminary analysis of IL-B30 transgenic founder mice.

Histological Analysis of IL-B30 Transgenic Mice

Microscopical examination of tissues collected from IL-B30 transgenic mice revealed minimal to moderate inflammation in multiple sites, including the lung, skin, esophagus, small intestine and liver (bile ducts), large intestine, and pancreas. Inflammatory infiltrates consisted of neutrophils, lymphocytes, and/or macrophages. Inflammation in the skin was associated with acanthosis and/or ulceration in some mice. In the lungs, peribronchial mononuclear cell infiltrates were sometimes prominent, alveolar walls contained increased numbers of leukocytes, and the epithelium lining airways was hyperplastic. Minimal periportal mononuclear cell infiltrates were also common in the liver. The cortex of lymph nodes was sometimes sparsely cellular and lacked follicular development.

Extramedullary hematopoiesis (EMH) was observed in the liver, spleen, and lymph nodes. The EMH was especially marked in the spleen. The spleens from three transgenic mice and one control mouse were examined after immunohistological staining for T cells (anti-CD3), B cells (anti-B220), and macrophages (anti-F4/80). In the transgenic mice the CD3-, B220-, and F4/80-positive cells were present in their normal locations. However, the white pulp was separated by the EMH in the red pulp, and the positively staining cells within the red pulp were interspersed with hematopoietic cells that stained with less intensity, or did not stain positively, with the various antibodies. These observations demonstrate that transgenic expression of IL-B30 induces systemic inflammation that is associated with EMH.

To analyze the effect of IL-B30 on leukocyte and platelet counts in the peripheral blood, a complete blood analysis was performed. The number of neutrophils in the blood of IL-B30 transgenic mice was increased 3- to 11-fold over the highest neutrophil count in control littermates. Increases in peripheral blood neutrophils are typical of inflammation and correlate with the infiltration of neutrophils observed in various tissues. Accordingly, the myeloid (granulocytic)/erythroid ratio was increased in the bone marrow.

In addition, the number of circulating platelets was increased up to 3-fold in IL-B30 transgenic mice over control littermates. An increased number of platelets could originate from either an increased number of megakaryocytes, or from an increase in production of platelets by megakaryocytes. To test either possibility, the peripheral blood, bone marrow and spleen from IL-B30 transgenic mice were analyzed microscopically. In the peripheral blood, platelets of bizarre morphology, including elongated and spindle-shaped platelets, were frequently detected. In bone marrow and spleen of some mice, megakaryocytes were enlarged due to increased amounts of cytoplasm. In contrast, the number of megakaryocytes in bone marrow and spleen was not increased. This suggests that IL-B30 induces an increase in the number of platelets by accelerating their production by megakaryocytes.

All IL-B30 transgenic mice examined also suffered from mild to moderate microcytic hypochromic anemia with schistocytes and varying degrees of regeneration evident. The hematocrit values were lower than the control mean by 36 to 70%. The presence of microcytic hypochromic anemia suggests a defect in hemoglobin production.

Cytokine Profile of IL-B30 Transgenic Mice

To test whether the systemic inflammation seen in IL-B30 transgenic mice correlated with altered expression of pro-inflammatory cytokines, we determined the concentrations of IL-1, TNFα, IL-6, and IFNγ in the peripheral blood. In all IL-B30 transgenic mice tested, the levels of TNFα and IFNγ were increased. In addition, the level of IL-1 was increased in 25% of IL-B30 transgenic mice tested. Concentrations of IL-1 and TNFα found in IL-B30 transgenic mice reached levels associated with the induction of an acute inflammatory response by LPS. Surprisingly, no IL-6 was detected in the peripheral blood of IL-B30 transgenic mice, even though expression of IL-6 is highly induced under inflammatory conditions (Reinecker et al., (1993) *Clin. Exp. Immunology* 94: 174–181; Stevens et al., (1992) *Dig. Dis. Sci.* 37: 818–826) and can be induced directly by TNFα, IL-1 and IFNγ (Helle et al., (1988) *Eur. J. Immunol.* 18: 957–959.

Acute Phase Genes in the Livers of IL-B30 Transgenic Mice

The body reacts to inflammation with an acute phase response characterized by the expression of defined plasma proteins in the liver. Since IL-B30 transgenic mice exhibit a phenotype characteristic of systemic inflammation, we examined the expression of acute phase genes in the livers of IL-B30 transgenic mice and control littermates. The acute phase liver genes alpha-1-acid glycoprotein, haptoglobin and hemopexin were highly expressed in all IL-B30 transgenic mice tested, while no expression of these genes was detected in control littermates. This demonstrates that acute phase liver genes are constitutively expressed in IL-B30 transgenic animals.

Serum Immunoglobulins of IL-B30 Transgenic Mice

During an immune response, some cytokines induce B cell differentiation and subsequent immunoglobulin synthesis. To test whether immunoglobulin synthesis was altered in IL-B30 transgenic mice, the concentrations of immunoglobulin isotypes in the peripheral blood were determined. In 2 of 7 IL-B30 transgenic mice, the concentration of IgA was increased 6- to 9-fold when compared to control littermates. Furthermore, the concentrations of IgG1, IgG2a and IgG2b were increased 2.5 to 6-fold in all IL-B30 transgenic mice tested when compared to control littermates. In contrast, no significant increase in IgM or IgE titers could be detected in any of the IL-B30 transgenic mice tested. In fact, 4 of 7 IL-B30 transgenic mice displayed markedly decreased levels of IgM synthesis. In summary, a subset of IL-B30 transgenic mice displayed a 6- to 9-fold increase in the concentrations of immunoglobulin isotypes IgA and IgG, whereas no significant increase was detected in the concentrations of immunoglobulin isotypes IgM and IgE.

Serum IGF-1 Levels in IL-B30 Transgenic Mice

Chronic inflammatory conditions (Kirschner and Sutton, (1986) *Gastroenterology* 91: 830–836; Laursen et al., (1995) *Arch. Dis. Child.* 72:494–497) or overexpression of cytokines in transgenic animals (De Benedetti et al., (1994) *J. Clin. Invest.* 93: 2114–2119) can cause growth impairment that is associated with a decrease of insulin-like growth factor-1 (IGF-1). To test whether stunted growth of IL-B30 transgenic mice could be traced to reduced levels of IGF-1, serum samples of transgenic mice were assayed for IGF-1. In all IL-B30 transgenic mice tested, the amount of IGF-1 in the serum was 12 to 14% of the level found in age-matched control littermates. This suggests that transgenic expression of IL-B30, as well as the subsequent inflammatory response produced, results in the reduction of IGF-1 in IL-B30 transgenic mice, and could consequently be the cause of impaired growth and infertility (Gay et al., (1997) *Endocrinology* 137(7): 2937–2947).

Expression of Biologically Active IL-B30 in Hematopoietic Cells

Cytokines are secreted proteins that regulate the immune system locally or mediate long-range effects. To test whether IL-B30 functions as a cytokine and can induce distant multi-organ inflammation and an acute phase liver response, we transferred IL-B30 transgenic bone marrow into lethally irradiated wildtype recipient mice.

Bone marrow recipients were monitored weekly for the induction of an acute phase response. Increased concentrations of the acute phase protein SAA could be detected in IL-B30 bone marrow recipients as early as 35 days post transfer and levels of SAA increased over time. Concurrent with increasing concentrations of SAA in the peripheral blood the health of IL-B30 bone marrow recipients deteriorated as judged by the appearance of ruffled fur and inflamed skin around the snout and throat. In contrast, recipients of wildtype bone marrow did not have elevated levels of SAA in blood, nor did they appear sick.

Animals were terminated when they appeared severely sick. Expression of IL-B30 could be detected in the bone marrow and spleen of recipients of IL-B30 transgenic bone marrow, but not in organs of recipients of wildtype bone marrow. As in IL-B30 transgenic donors skin, lung, liver, and the gastrointestinal tract were inflamed in recipients of IL-B30 transgenic bone marrow, but not in wildtype bone marrow recipients. Again acute phase liver genes (hemopexin, AGP-1) were highly expressed in IL-B30 transgenic bone marrow recipients, but no IL-6 could be detected in blood serum. These results suggest that IL-B30 is a true cytokine with long-ranging properties.

Transgenic expression of IL-B30 induces a striking phenotype characterized by runting, systemic inflammation, infertility and death of transgenic animals. IL-B30 transgenic animals have systemic inflammation with infiltration of inflammatory cells into lung, liver, skin, and the digestive tract.

Overexpression of IL-B30 in vivo caused a phenotype of impaired growth and inflammation—that was strikingly similar to that of several models of transgenic expression of IL-6. Similar to the effect of transgenic expression of IL-6, or after administration of recombinant IL-6 to mice, neutrophil infiltration and anemia were observed in animals as a result of transgenic expression of IL-B30. As in IL-6 transgenic animals, impaired growth of IL-B30 transgenic founders was linked to decreased levels of IGF-1 that might be related to the systemic inflammation observed in these animals.

This phenotype of IL-B30 transgenic animals could be caused by upregulated IL-6 expression either as a direct effect of IL-B30 overexpression, or by IL-B30 mediated upregulation of IL-1 and TNFα expression. IL-1 and TNFα are known inducers of IL-6 and increased concentrations of TNFα and IL-1 were found in the peripheral blood of IL-B30 transgenic mice.

However, no IL-6 could be detected in blood of IL-B30 transgenic suggesting that the phenotype of IL-B30 animals is directly linked to overexpression of this novel cytokine and, as had been implied by their sequence homologies, that IL-B30 has biological activities similar to IL-6.

IL-6 is a pleiotropic cytokine that among a wide variety of functions induces thrombocytosis, acute-phase protein synthesis, and B cell differentiation.

Indeed, IL-B30 transgenic animals express constitutively acute phase liver genes like AGP-1, haptoglobin, hemopexin and serum amyloid A protein. A similar phenotype has been shown in mice as an effect of transgenic overexpression of IL-6, or after administration of recombinant IL-6. In addition, transgenic expression of IL-B30 resulted in thrombocytosis that was unusual in that many of the platelets had bizarre morphology (elongated appearance, large size, and/or spindle shapes). We suspect that IL-B30 and/or other upregulated cytokines have an effect on normal platelet production. This suggests again that IL-B30 shares a biological activity with IL-6 and its relatives.

IL-6 has also been identified as a B cell differentiation factor. Transgenic overexpression of IL-6 causes plasmocytoma and IL-6 deficient mice show a reduced IgG response. While we saw increases in IgG and IgA production in some IL-B30 transgenic mice, this observation was not consistent between different founders. Thus further analysis is needed to characterize IL-B30 further as a potential B cell differentiation factor.

In IL-B30 transgenic mice increases in circulating neutrophils were consistent with the inflammation evident in various tissues, however, the changes in red blood cell parameters are not as easily explained. IL-1, TNF-alpha, and IFN-gamma are mediators of a syndrome commonly called anemia of chronic disease (ACD), which generally presents as a normocytic, normochromic, nonregenerative (or minimally regenerative) anemia and is seen in a variety of chronic inflammatory diseases. Anemia of Chronic Disease may also present as microcytic, hypochromic in some human patients. The syndrome is due to altered iron metabolism and diminished response to erythropoietin. The microcytic hypochromic anemia observed in the IL-B30 mice may be due to ACD, as suggested by the increases in peripheral cytokine concentrations. However, the most common cause of microcytic hypochromic anemia is iron deficiency, which is more consistent with the partial bone marrow response (regeneration) and thrombocytosis seen in the IL-B30 mice. Further investigation, including measurement of serum ferritin, iron, and total iron binding capacity, which would allow differentiation of ACD from iron deficiency anemia, was not undertaken due to the difficulties in obtaining adequate blood from affected mice.

IL-1 and TNF-alpha are known inducers of IL-6 expression and IL-6 expression is usually upregulated during an inflammatory response. Therefore it is surprising that IL-6 could not be detected in the peripheral blood of IL-B30 transgenic animals. This suggests that IL-B30 has a negative effect on IL-6 expression by a yet unidentified mechanism. Indeed the absence of IL-6 in IL-B30 transgenic animals might explain the high levels of IL-1 and TNF-alpha observed in these animals since IL-6 has a negative effect on the concentrations of circulating IL-1 and TNF-alpha in mice. The high concentrations of circulating TNF-alpha observed in IL-B30 transgenic mice could also be an result of the increased concentrations of IFN-gamma. IFN-gamma is produced by IL-2 activated T cells or IL-4-activated B cells, and induces the expression of TNF-alpha in monocytes and macrophages. It remains to be determined whether expression of IFN-gamma is mediated directly by IL-B30 or by other cytokines induced by IL-B30. In summary, our results suggest that IL-B30 shares a wide variety of biological activities with IL-6. It remains to be seen whether these biological activities are mediated by a common receptor, a signal transduction element or transcription factor shared with IL-6. These issues will hopefully be clarified by ongoing experiments using genetic and biochemical approaches.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

SEQUENCE LISTING

```
<160> NUMBER OF SEQ ID NOS: 5

<210> SEQ ID NO 1
<211> LENGTH: 570
<212> TYPE: DNA
<213> ORGANISM: Unknown Organism
<220> FEATURE:
<223> OTHER INFORMATION: Description of Unknown Organism: surmised Homo
      sapiens
<220> FEATURE:
```

```
<221> NAME/KEY: CDS
<222> LOCATION: (1)..(567)
<220> FEATURE:
<221> NAME/KEY: mat_peptide
<222> LOCATION: (64)..(567)

<400> SEQUENCE: 1 atg ctg ggg agc aga gct gta atg ctg ctg ttg ctg ctg ccc tgg aca      48
Met Leu Gly Ser Arg Ala Val Met Leu Leu Leu Leu Leu Pro Trp Thr
    -20                 -15                 -10 gct cag ggc aga gct gtg cct ggg ggc agc agc cct gcc tgg act cag      96
Ala Gln Gly Arg Ala Val Pro Gly Gly Ser Ser Pro Ala Trp Thr Gln
 -5              -1   1               5                  10 tgc cag cag ctt tca cag aag ctc tgc aca ctg gcc tgg agt gca cat     144
Cys Gln Gln Leu Ser Gln Lys Leu Cys Thr Leu Ala Trp Ser Ala His
             15                  20                  25 cca cta gtg gga cac atg gat cta aga gaa gag gga gat gaa gag act     192
Pro Leu Val Gly His Met Asp Leu Arg Glu Glu Gly Asp Glu Glu Thr
         30                  35                  40 aca aat gat gtt ccc cat atc cag tgt gga gat ggc tgt gac ccc caa     240
Thr Asn Asp Val Pro His Ile Gln Cys Gly Asp Gly Cys Asp Pro Gln
     45                  50                  55 gga ctc agg gac aac agt cag ttc tgc ttg caa agg atc cac cag ggt     288
Gly Leu Arg Asp Asn Ser Gln Phe Cys Leu Gln Arg Ile His Gln Gly
 60                  65                  70                  75 ctg att ttt tat gag aag ctg cta gga tcg gat att ttc aca ggg gag     336
Leu Ile Phe Tyr Glu Lys Leu Leu Gly Ser Asp Ile Phe Thr Gly Glu
                 80                  85                  90 cct tct ctg ctc cct gat agc cct gtg gcg cag ctt cat gcc tcc cta     384
Pro Ser Leu Leu Pro Asp Ser Pro Val Ala Gln Leu His Ala Ser Leu
             95                 100                 105 ctg ggc ctc agc caa ctc ctg cag cct gag ggt cac cac tgg gag act     432
Leu Gly Leu Ser Gln Leu Leu Gln Pro Glu Gly His His Trp Glu Thr
         110                 115                 120 cag cag att cca agc ctc agt ccc agc cag cca tgg cag cgt ctc ctt     480
Gln Gln Ile Pro Ser Leu Ser Pro Ser Gln Pro Trp Gln Arg Leu Leu
     125                 130                 135 ctc cgc ttc aaa atc ctt cgc agc ctc cag gcc ttt gtg gct gta gcc     528
Leu Arg Phe Lys Ile Leu Arg Ser Leu Gln Ala Phe Val Ala Val Ala
140                 145                 150                 155 gcc cgg gtc ttt gcc cat gga gca gca acc ctg agt ccc taa             570
Ala Arg Val Phe Ala His Gly Ala Ala Thr Leu Ser Pro
                 160                 165

<210> SEQ ID NO 2
<211> LENGTH: 189
<212> TYPE: PRT
<213> ORGANISM: Unknown Organism
<220> FEATURE:
<223> OTHER INFORMATION: Description of Unknown Organism: surmised Homo
      sapiens

<400> SEQUENCE: 2

Met Leu Gly Ser Arg Ala Val Met Leu Leu Leu Leu Leu Pro Trp Thr
    -20                 -15                 -10

Ala Gln Gly Arg Ala Val Pro Gly Gly Ser Ser Pro Ala Trp Thr Gln
 -5              -1   1               5                  10

Cys Gln Gln Leu Ser Gln Lys Leu Cys Thr Leu Ala Trp Ser Ala His
             15                  20                  25

Pro Leu Val Gly His Met Asp Leu Arg Glu Glu Gly Asp Glu Glu Thr
         30                  35                  40
```

```
Thr Asn Asp Val Pro His Ile Gln Cys Gly Asp Gly Cys Asp Pro Gln
    45                  50                  55
Gly Leu Arg Asp Asn Ser Gln Phe Cys Leu Gln Arg Ile His Gln Gly
60                  65                  70                  75
Leu Ile Phe Tyr Glu Lys Leu Leu Gly Ser Asp Ile Phe Thr Gly Glu
                80                  85                  90
Pro Ser Leu Leu Pro Asp Ser Pro Val Ala Gln Leu His Ala Ser Leu
                95                  100                 105
Leu Gly Leu Ser Gln Leu Leu Gln Pro Glu Gly His His Trp Glu Thr
        110                 115                 120
Gln Gln Ile Pro Ser Leu Ser Pro Ser Gln Pro Trp Gln Arg Leu Leu
    125                 130                 135
Leu Arg Phe Lys Ile Leu Arg Ser Leu Gln Ala Phe Val Ala Val Ala
140                 145                 150                 155
Ala Arg Val Phe Ala His Gly Ala Ala Thr Leu Ser Pro
                160                 165
```

<210> SEQ ID NO 3
<211> LENGTH: 1203
<212> TYPE: DNA
<213> ORGANISM: Unknown Organism
<220> FEATURE:
<223> OTHER INFORMATION: Description of Unknown Organism: surmised Mus sp.
<220> FEATURE:
<221> NAME/KEY: CDS
<222> LOCATION: (113)..(700)
<220> FEATURE:
<221> NAME/KEY: mat_peptide
<222> LOCATION: (176)..(700)

<400> SEQUENCE: 3

```
cgcttagaag tcggactaca gagttagact cagaaccaaa ggaggtggat aggggtcca      60 caggcctggt gcagatcaca gagccagcca gatctgagaa gcagggaaca ag atg ctg    118
                                                          Met Leu
                                                              -20 gat tgc aga gca gta ata atg cta tgg ctg ttg ccc tgg gtc act cag     166
Asp Cys Arg Ala Val Ile Met Leu Trp Leu Leu Pro Trp Val Thr Gln
            -15                 -10                  -5 ggc ctg gct gtg cct agg agt agc agt cct gac tgg gct cag tgc cag     214
Gly Leu Ala Val Pro Arg Ser Ser Ser Pro Asp Trp Ala Gln Cys Gln
 -1   1               5                  10 cag ctc tct cgg aat ctc tgc atg cta gcc tgg aac gca cat gca cca     262
Gln Leu Ser Arg Asn Leu Cys Met Leu Ala Trp Asn Ala His Ala Pro
         15                  20                  25 gcg gga cat atg aat cta cta aga gaa gaa gag gat gaa gag act aaa     310
Ala Gly His Met Asn Leu Leu Arg Glu Glu Glu Asp Glu Glu Thr Lys
 30                  35                  40                  45 aat aat gtg ccc cgt atc cag tgt gaa gat ggt tgt gac cca caa gga     358
Asn Asn Val Pro Arg Ile Gln Cys Glu Asp Gly Cys Asp Pro Gln Gly
                 50                  55                  60 ctc aag gac aac agc cag ttc tgc ttg caa agg atc cgc caa ggt ctg     406
Leu Lys Asp Asn Ser Gln Phe Cys Leu Gln Arg Ile Arg Gln Gly Leu
             65                  70                  75 gct ttt tat aag cac ctg ctt gac tct gac atc ttc aaa ggg gag cct     454
Ala Phe Tyr Lys His Leu Leu Asp Ser Asp Ile Phe Lys Gly Glu Pro
         80                  85                  90 gct cta ctc cct gat agc ccc atg gag caa ctt cac acc tcc cta cta     502
Ala Leu Leu Pro Asp Ser Pro Met Glu Gln Leu His Thr Ser Leu Leu
     95                  100                 105
```

```
gga ctc agc caa ctc ctc cag cca gag gat cac ccc cgg gag acc caa    550
Gly Leu Ser Gln Leu Leu Gln Pro Glu Asp His Pro Arg Glu Thr Gln
110                 115                 120                 125 cag atg ccc agc ctg agt tct agt cag cag tgg cag cgc ccc ctt ctc    598
Gln Met Pro Ser Leu Ser Ser Ser Gln Gln Trp Gln Arg Pro Leu Leu
                130                 135                 140 cgt tcc aag atc ctt cga agc ctc cag gcc ttt ttg gcc ata gct gcc    646
Arg Ser Lys Ile Leu Arg Ser Leu Gln Ala Phe Leu Ala Ile Ala Ala
            145                 150                 155 cgg gtc ttt gcc cac gga gca gca act ctg act gag ccc tta gtg cca    694
Arg Val Phe Ala His Gly Ala Ala Thr Leu Thr Glu Pro Leu Val Pro
        160                 165                 170 aca gct taaggatgcc caggttccca tggctaccat gataagacta atctatcagc     750
Thr Ala
    175 ccagacatct accagttaat taacccatta ggacttgtgc tgttcttgtt tcgtttgttt    810 tgcgtgaagg gcaaggacac cattattaaa gagaaaagaa acaaacccca gagcaggcag    870 ctggctagag aaaggagctg gagaagaaga ataaagtctc gagcccttgg ccttggaagc    930 gggcaagcag ctgcgtggcc tgaggggaag ggggcggtgg catcgagaaa ctgtgagaaa    990 acccagagca tcagaaaaag tgagcccagg ctttggccat tatctgtaag aaaaacaaga   1050 aaagggaac attatacttt cctgggtggc tcagggaaat gtgcagatgc acagtactcc   1110 agacagcagc tctgtacctg cctgctctgt ccctcagttc taacagaatc tagtcactaa   1170 gaactaacag gactaccaat acgaactgac aaa                              1203

<210> SEQ ID NO 4
<211> LENGTH: 196
<212> TYPE: PRT
<213> ORGANISM: Unknown Organism
<220> FEATURE:
<223> OTHER INFORMATION: Description of Unknown Organism: surmised Mus
      sp.

<400> SEQUENCE: 4

Met Leu Asp Cys Arg Ala Val Ile Met Leu Trp Leu Leu Pro Trp Val
    -20                 -15                 -10

Thr Gln Gly Leu Ala Val Pro Arg Ser Ser Ser Pro Asp Trp Ala Gln
-5              -1   1               5                   10

Cys Gln Gln Leu Ser Arg Asn Leu Cys Met Leu Ala Trp Asn Ala His
                15                  20                  25

Ala Pro Ala Gly His Met Asn Leu Leu Arg Glu Glu Asp Glu Glu
            30                  35                  40

Thr Lys Asn Asn Val Pro Arg Ile Gln Cys Glu Asp Gly Cys Asp Pro
        45                  50                  55

Gln Gly Leu Lys Asp Asn Ser Gln Phe Cys Leu Gln Arg Ile Arg Gln
60                  65                  70                  75

Gly Leu Ala Phe Tyr Lys His Leu Leu Asp Ser Asp Ile Phe Lys Gly
                80                  85                  90

Glu Pro Ala Leu Leu Pro Asp Ser Pro Met Glu Gln Leu His Thr Ser
            95                  100                 105

Leu Leu Gly Leu Ser Gln Leu Leu Gln Pro Glu Asp His Pro Arg Glu
        110                 115                 120

Thr Gln Gln Met Pro Ser Leu Ser Ser Ser Gln Gln Trp Gln Arg Pro
    125                 130                 135

Leu Leu Arg Ser Lys Ile Leu Arg Ser Leu Gln Ala Phe Leu Ala Ile
```

-continued

```
                140                 145                 150                 155
            Ala Ala Arg Val Phe Ala His Gly Ala Ala Thr Leu Thr Glu Pro Leu
                            160                 165                 170

Val Pro Thr Ala
                        175

<210> SEQ ID NO 5
<211> LENGTH: 102
<212> TYPE: PRT
<213> ORGANISM: Unknown Organism
<220> FEATURE:
<223> OTHER INFORMATION: Description of Unknown Organism: surmised Sus
      sp.

<400> SEQUENCE: 5

Ser Cys Leu Gln Arg Ile His Gln Gly Leu Val Phe Tyr Glu Lys Leu
 1               5                  10                  15

Leu Gly Ser Asp Ile Phe Thr Gly Glu Pro Ser Leu His Pro Asp Gly
             20                  25                  30

Ser Val Gly Gln Leu His Ala Ser Leu Leu Gly Leu Arg Gln Leu Leu
         35                  40                  45

Gln Pro Glu Gly His His Trp Glu Thr Glu Gln Thr Pro Ser Pro Ser
     50                  55                  60

Pro Ser Gln Pro Trp Gln Arg Leu Leu Leu Arg Leu Lys Ile Leu Arg
 65                  70                  75                  80

Ser Leu Gln Ala Phe Val Ala Val Ala Ala Arg Val Phe Ala His Gly
                 85                  90                  95

Ala Ala Thr Leu Ser Gln
            100
```

What is claimed is:

1. A composition comprising a substantially pure polypeptide comprising an IL-12 p40 fused to an IL-B30, wherein the IL-12 p40 is encoded by the mature coding sequence of SEQ ID NO: 19, and the IL-B30 is encoded by the mature coding sequence of SEQ ID NO:1.

2. The composition of claim 1 wherein the polypeptide is a fusion protein comprising, from the N-terminus to the C-terminus, the IL-12 p40, a linker, and the IL-B30.

3. A nucleic acid encoding a fusion protein comprising an IL-12 p40 fused to an IL-B30, wherein the IL-12 p40 is encoded by the mature coding sequence of SEQ ID NO: 19, and the IL-B30 is encoded by the mature coding sequence of SEQ ID NO:1.

4. The nucleic acid of claim 3 wherein the fusion protein comprises, from the N-terminus to the C-terminus, the IL-12 p40, a linker, and the IL-B30.

5. The nucleic acid of claim 4 prepared by using synthetic DNA encoding the IL-12 p40, the linker, and the IL-B30.

6. A method of preparing a fusion protein of IL-12 p40 and IL-B30, said method comprising:
   (1) providing an expression vector that comprises the nucleic acid of claim 3;
   (2) expressing the fusion protein in a cell using said expression vector; and
   (3) preparing the fusion protein from said cell.

7. The method of claim 6 wherein the fusion protein comprises, from the N-terminus to the C-terminus, the IL-12 p40, a linker, and the IL-B30.

8. An isolated nucleic acid encoding a fusion protein comprising an IL-12 p40 fused to an IL-B30, wherein the IL-12 p40 is encoded by a sequence that is at least 95% identical to SEQ ID NO:19, the IL-B30 is encoded by a sequence that is at least 95% identical to SEQ ID NO:1, and the fusion protein enhances or inhibits production of IFNγ, TNFα and/or IL-1.

9. An isolated cell comprising the nucleic acid of claim 7.

10. A composition comprising a polypeptide encoded by the nucleic acid of claim 8.

11. The composition of claim 10 wherein the polypeptide is a fusion protein comprising, from the N-terminus to the C-terminus, the IL-12 p40, a linker, and the IL-B30.

12. The composition of claim 10, further comprising an acceptable carrier.

13. The cell of claim 9, which is an insect cell.

14. A method of preparing a fusion protein of IL-12 p40 and IL-B30, said method comprising:
   (1) providing an expression vector that comprises the nucleic acid of claim 8;
   (2) expressing the fusion protein in a cell using said expression vector; and
   (3) preparing the fusion protein from said cell.

15. The method of claim 14 wherein the fusion protein comprises, from the N-terminus to the C-terminus, the IL-12 p40, a linker, and the IL-B30.

16. The method of claim 15 wherein the expression vector is prepared by using synthetic DNA encoding the IL-12 p40, the linker, and the IL-B30.

17. The nucleic acid of claim 8 further comprising a signal sequence.

18. The method of claim 14 wherein the expression vector further comprises a signal sequence.

19. An isolated nucleic acid encoding a fusion protein comprising an IL-12 p40 fused to an IL-B30, wherein the IL-12 p40 is encoded by a sequence that is at least 95% identical to SEQ ID NO:19, the IL-B30 is encoded by a sequence that is at least 95% identical to SEQ ID NO:1, and the fusion protein stimulates or inhibits proliferation of memory T cells.

20. A composition comprising a substantially pure polypeptide encoded by the nucleic acid of claim 19.

21. A method of preparing a fusion protein of IL-12 p40 and IL B30, said method comprising:

(1) providing an expression vector that comprises the nucleic acid of claim 19;

(2) expressing the fusion protein in a cell using said expression vector; and (3) preparing the fusion protein from said cell.

22. A composition comprising a polypeptide encoded by the nucleic acid of claim 19.

* * * * *

UNITED STATES PATENT AND TRADEMARK OFFICE
CERTIFICATE OF CORRECTION

| | | |
|---|---|---|
| PATENT NO. | : 7,183,382 B2 | Page 1 of 40 |
| APPLICATION NO. | : 10/375706 | |
| DATED | : February 27, 2007 | |
| INVENTOR(S) | : Oppmann et al. | |

It is certified that error appears in the above-identified patent and that said Letters Patent is hereby corrected as shown below:

Column 47 through column 56 insert the sequences as shown on the attached pages.

Signed and Sealed this

Twenty-fourth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
--   <160> 36

<210> 1
     <211> 570
     <212> DNA
     <213> Unknown Organism

<220>
     <223> Description of Unknown Organism: surmised Homo
           sapiens

<220>
     <221> CDS
     <222> (1)..(567)

<220>
     <221> mat_peptide
     <222> (54)..(567)

<400> 1
     atg ctg ggg agc aga gct gta atg ctg ctg ttg ctg ctg ccc tgg aca    48
     Met Leu Gly Ser Arg Ala Val Met Leu Leu Leu Leu Leu Pro Trp Thr
         -20                 -15                 -10 gct cag ggc aga gct gtg cct ggg ggc agc agc cct gcc tgg act cag    96
     Ala Gln Gly Arg Ala Val Pro Gly Gly Ser Ser Pro Ala Trp Thr Gln
      -5              -1   1               5                   10 tgc cag cag ctt tca cag aag ctc tgc aca ctg gcc tgg agt gca cat   144
     Cys Gln Gln Leu Ser Gln Lys Leu Cys Thr Leu Ala Trp Ser Ala His
                      15                  20                  25 cca cta gtg gga cac atg gat cta aga gaa gag gga gat gaa gag act   192
     Pro Leu Val Gly His Met Asp Leu Arg Glu Glu Gly Asp Glu Glu Thr
                  30                  35                  40
```

UNITED STATES PATENT AND TRADEMARK OFFICE
CERTIFICATE OF CORRECTION

PATENT NO.         : 7,183,382 B2                                    Page 3 of 40
APPLICATION NO. : 10/375706
DATED              : February 27, 2007
INVENTOR(S)       : Oppmann et al.

It is certified that error appears in the above-identified patent and that said Letters Patent is hereby corrected as shown below:

```
aca aat gat gtt ccc cat atc cag tgt gga gat ggc tgt gac ccc caa    240
Thr Asn Asp Val Pro His Ile Gln Cys Gly Asp Gly Cys Asp Pro Gln
         45                  50                  55 gga ctc agg gac aac agt cag ttc tgc ttg caa agg atc cac cag ggt    288
Gly Leu Arg Asp Asn Ser Gln Phe Cys Leu Gln Arg Ile His Gln Gly
 60                  65                  70                  75 ctg att ttt tat gag aag ctg cta gga tcg gat att ttc aca ggg gag    336
Leu Ile Phe Tyr Glu Lys Leu Leu Gly Ser Asp Ile Phe Thr Gly Glu
                 80                  85                  90 cct tct ctg ctc cct gat agc cct gtg gcg cag ctt cat gcc tcc cta    384
Pro Ser Leu Leu Pro Asp Ser Pro Val Ala Gln Leu His Ala Ser Leu
             95                 100                 105 ctg ggc ctc agc caa ctc ctg cag cct gag ggt cac cac tgg gag act    432
Leu Gly Leu Ser Gln Leu Leu Gln Pro Glu Gly His His Trp Glu Thr
        110                 115                 120 cag cag att cca agc ctc agt cca agc cag cca tgg cag cgt ctc ctt    480
Gln Gln Ile Pro Ser Leu Ser Pro Ser Gln Pro Trp Gln Arg Leu Leu
    125                 130                 135 ctc cgc ttc aaa atc ctt cgc agc ctc cag gcc ttt gtg gct gta gcc    528
Leu Arg Phe Lys Ile Leu Arg Ser Leu Gln Ala Phe Val Ala Val Ala
140                 145                 150                 155 gcc cgg gtc ttt gcc cat gga gca gca acc ctg agt ccc taa            570
Ala Arg Val Phe Ala His Gly Ala Ala Thr Leu Ser Pro
                160                 165

<210> 2
<211> 189
<212> PRT
<213> Unknown Organism
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<220>
<223> surmised Homo sapiens

<400> 2
Met Leu Gly Ser Arg Ala Val Met Leu Leu Leu Leu Pro Trp Thr
    -20                 -15                 -10

Ala Gln Gly Arg Ala Val Pro Gly Gly Ser Ser Pro Ala Trp Thr Gln
 -5              -1   1               5                    10

Cys Gln Gln Leu Ser Gln Lys Leu Cys Thr Leu Ala Trp Ser Ala His
             15                  20                  25

Pro Leu Val Gly His Met Asp Leu Arg Glu Glu Gly Asp Glu Glu Thr
             30                  35                  40

Thr Asn Asp Val Pro His Ile Gln Cys Gly Asp Gly Cys Asp Pro Gln
         45                  50                  55

Gly Leu Arg Asp Asn Ser Gln Phe Cys Leu Gln Arg Ile His Gln Gly
 60                  65                  70                  75

Leu Ile Phe Tyr Glu Lys Leu Leu Gly Ser Asp Ile Phe Thr Gly Glu
                 80                  85                      90

Pro Ser Leu Leu Pro Asp Ser Pro Val Ala Gln Leu His Ala Ser Leu
             95                  100                 105

Leu Gly Leu Ser Gln Leu Leu Gln Pro Glu Gly His His Trp Glu Thr
             110                 115                 120

Gln Gln Ile Pro Ser Leu Ser Pro Ser Gln Pro Trp Gln Arg Leu Leu
             125                 130                 135

Leu Arg Phe Lys Ile Leu Arg Ser Leu Gln Ala Phe Val Ala Val Ala
 140                 145                 150                 155
```

UNITED STATES PATENT AND TRADEMARK OFFICE
CERTIFICATE OF CORRECTION

| | |
|---|---|
| PATENT NO. | : 7,183,382 B2 |
| APPLICATION NO. | : 10/375706 |
| DATED | : February 27, 2007 |
| INVENTOR(S) | : Oppmann et al. |

It is certified that error appears in the above-identified patent and that said Letters Patent is hereby corrected as shown below:

```
Ala Arg Val Phe Ala His Gly Ala Ala Thr Leu Ser Pro
            160                 165

<210> 3
<211> 1203
<212> DNA
<213> Unknown Organism

<220>
<223> Description of Unknown Organism: surmised Mus sp.

<220>
<221> CDS
<222> (113)..(700)

<220>
<221> mat_peptide
<222> (176)..(700)

<400> 3
cgcttagaag tcggactaca gagttagact cagaaccaaa ggaggtggat aggggtcca    60 caggcctggt gcagatcaca gagccagcca gatctgagaa gcagggaaca ag atg ctg   118
                                                         Met Leu
                                                          -20 gat tgc aga gca gta ata atg cta tgg ctg ttg ccc tgg gtc act cag    166
Asp Cys Arg Ala Val Ile Met Leu Trp Leu Leu Pro Trp Val Thr Gln
            -15                 -10                  -5 ggc ctg gct gtg cct agg agt agc agt cct gac tgg gct cag tgc cag    214
Gly Leu Ala Val Pro Arg Ser Ser Ser Pro Asp Trp Ala Gln Cys Gln
        -1   1                   5                  10 cag ctc tct cgg aat ctc tgc atg cta gcc tgg aac gca cat gca cca    262
Gln Leu Ser Arg Asn Leu Cys Met Leu Ala Trp Asn Ala His Ala Pro
         15                  20                  25
```

UNITED STATES PATENT AND TRADEMARK OFFICE
CERTIFICATE OF CORRECTION

PATENT NO.       : 7,183,382 B2
APPLICATION NO.  : 10/375706
DATED            : February 27, 2007
INVENTOR(S)      : Oppmann et al.

It is certified that error appears in the above-identified patent and that said Letters Patent is hereby corrected as shown below:

```
gcg gga cat atg aat cta cta aga gaa gaa gag gat gaa gag act aaa    310
Ala Gly His Met Asn Leu Leu Arg Glu Glu Glu Asp Glu Glu Thr Lys
 30              35              40              45 aat aat gtg ccc cgt atc cag tgt gaa gat ggt tgt gac cca caa gga    358
Asn Asn Val Pro Arg Ile Gln Cys Glu Asp Gly Cys Asp Pro Gln Gly
             50              55              60 ctc aag gac aac agc cag ttc tgc ttg caa agg atc cgc caa ggt ctg    406
Leu Lys Asp Asn Ser Gln Phe Cys Leu Gln Arg Ile Arg Gln Gly Leu
             65              70              75 gct ttt tat aag cac ctg ctt gac tct gac atc ttc aaa ggg gag cct    454
Ala Phe Tyr Lys His Leu Leu Asp Ser Asp Ile Phe Lys Gly Glu Pro
             80              85              90 gct cta ctc cct gat agc ccc atg gag caa ctt cac acc tcc cta cta    502
Ala Leu Leu Pro Asp Ser Pro Met Glu Gln Leu His Thr Ser Leu Leu
         95             100             105 gga ctc agc caa ctc ctc cag cca gag gat cac ccc cgg gag acc caa    550
Gly Leu Ser Gln Leu Leu Gln Pro Glu Asp His Pro Arg Glu Thr Gln
110             115             120             125 cag atg ccc agc ctg agt tct agt cag cag tgg cag cgc ccc ctt ctc    598
Gln Met Pro Ser Leu Ser Ser Ser Gln Gln Trp Gln Arg Pro Leu Leu
            130             135             140 cgt tcc aag atc ctt cga agc ctc cag gcc ttt ttg gcc ata gct gcc    646
Arg Ser Lys Ile Leu Arg Ser Leu Gln Ala Phe Leu Ala Ile Ala Ala
            145             150             155 cgg gtc ttt gcc cac gga gca gca act ctg act gag ccc tta gtg cca    694
Arg Val Phe Ala His Gly Ala Ala Thr Leu Thr Glu Pro Leu Val Pro
            160             165             170
```

UNITED STATES PATENT AND TRADEMARK OFFICE
CERTIFICATE OF CORRECTION

PATENT NO.       : 7,183,382 B2
APPLICATION NO.  : 10/375706
DATED            : February 27, 2007
INVENTOR(S)      : Oppmann et al.

It is certified that error appears in the above-identified patent and that said Letters Patent is hereby corrected as shown below:

```
aca gct taaggatgcc caggttccca tggctaccat gataagacta atctatcagc    750
Thr Ala
    175 ccagacatct accagttaat taacccatta ggacttgtgc tgttcttgtt tcgtttgttt 810 tgcgtgaagg gcaaggacac cattattaaa gagaaaagaa acaaacccca gagcaggcag 870 ctggctagag aaaggagctg gagaagaaga ataaagtctc gagcccttgg ccttggaagc 930 gggcaagcag ctgcgtggcc tgaggggaag ggggcggtgg catcgagaaa ctgtgagaaa 990 acccagagca tcagaaaaag tgagcccagg ctttggccat tatctgtaag aaaaacaaga 1050 aaaggggaac attatacttt cctgggtggc tcagggaaat gtgcagatgc acagtactcc 1110 agacagcagc tctgtacctg cctgctctgt ccctcagttc taacagaatc tagtcactaa 1170 gaactaacag gactaccaat acgaactgac aaa                             1203

<210> 4
<211> 196
<212> PRT
<213> Unknown Organism

<220>
<223> surmised Mus sp.

<400> 4
Met Leu Asp Cys Arg Ala Val Ile Met Leu Trp Leu Leu Pro Trp Val
    -20                 -15                 -10

Thr Gln Gly Leu Ala Val Pro Arg Ser Ser Ser Pro Asp Trp Ala Gln
     -5              -1   1               5                  10

Cys Gln Gln Leu Ser Arg Asn Leu Cys Met Leu Ala Trp Asn Ala His
                15                  20                  25
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
    Ala Pro Ala Gly His Met Asn Leu Leu Arg Glu Glu Glu Asp Glu Glu
            30              35                  40

Thr Lys Asn Asn Val Pro Arg Ile Gln Cys Glu Asp Gly Cys Asp Pro
            45              50                  55

Gln Gly Leu Lys Asp Asn Ser Gln Phe Cys Leu Gln Arg Ile Arg Gln
    60              65              70                      75

Gly Leu Ala Phe Tyr Lys His Leu Leu Asp Ser Asp Ile Phe Lys Gly
                    80              85                      90

Glu Pro Ala Leu Leu Pro Asp Ser Pro Met Glu Gln Leu His Thr Ser
                95              100                 105

Leu Leu Gly Leu Ser Gln Leu Leu Gln Pro Glu Asp His Pro Arg Glu
            110             115                 120

Thr Gln Gln Met Pro Ser Leu Ser Ser Ser Gln Gln Trp Gln Arg Pro
            125             130             135

Leu Leu Arg Ser Lys Ile Leu Arg Ser Leu Gln Ala Phe Leu Ala Ile
    140             145                 150                 155

Ala Ala Arg Val Phe Ala His Gly Ala Ala Thr Leu Thr Glu Pro Leu
                    160             165                 170

Val Pro Thr Ala
                175

<210> 5
    <211> 102
    <212> PRT
    <213> Unknown Organism

<220>
    <223> Description of Unknown Organism: surmised Sus sp.
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 5
Ser Cys Leu Gln Arg Ile His Gln Gly Leu Val Phe Tyr Glu Lys Leu
 1               5                  10                  15

Leu Gly Ser Asp Ile Phe Thr Gly Glu Pro Ser Leu His Pro Asp Gly
            20                  25                  30

Ser Val Gly Gln Leu His Ala Ser Leu Leu Gly Leu Arg Gln Leu Leu
        35                  40                  45

Gln Pro Glu Gly His His Trp Glu Thr Glu Gln Thr Pro Ser Pro Ser
    50                  55                  60

Pro Ser Gln Pro Trp Gln Arg Leu Leu Leu Arg Leu Lys Ile Leu Arg
65                  70                  75                  80

Ser Leu Gln Ala Phe Val Ala Val Ala Ala Arg Val Phe Ala His Gly
                85                  90                  95

Ala Ala Thr Leu Ser Gln
            100

<210> 6
<211> 306
<212> PRT
<213> Homo sapiens

<400> 6
Ile Trp Glu Leu Lys Lys Asp Val Tyr Val Val Glu Leu Asp Trp Tyr
 1               5                  10                  15
Pro Asp Ala Pro Gly Glu Met Val Val Leu Thr Cys Asp Thr Pro Glu
            20                  25                  30
Glu Asp Gly Ile Thr Trp Thr Leu Asp Gln Ser Ser Glu Val Leu Gly
            35                  40                  45
Ser Gly Lys Thr Leu Thr Ile Gln Val Lys Glu Phe Gly Asp Ala Gly
            50                  55                  60
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Gln Tyr Thr Cys His Lys Gly Gly Glu Val Leu Ser His Ser Leu Leu
65                  70                  75                  80
Leu Leu His Lys Lys Glu Asp Gly Ile Trp Ser Thr Asp Ile Leu Lys
                85                  90                  95
Asp Gln Lys Glu Pro Lys Asn Lys Thr Phe Leu Arg Cys Glu Ala Lys
            100                 105                 110
Asn Tyr Ser Gly Arg Phe Thr Cys Trp Trp Leu Thr Thr Ile Ser Thr
        115                 120                 125
Asp Leu Thr Phe Ser Val Lys Ser Ser Arg Gly Ser Ser Asp Pro Gln
    130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
            180                 185                 190
Val His Lys Leu Lys Tyr Glu Asn Tyr Thr Ser Ser Phe Phe Ile Arg
        195                 200                 205
Asp Ile Ile Lys Pro Asp Pro Pro Lys Asn Leu Gln Leu Lys Pro Leu
    210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
            245                 250                 255
Gly Lys Ser Lys Arg Glu Lys Lys Asp Arg Val Phe Thr Asp Lys Thr
        260                 265                 270
Ser Ala Thr Val Ile Cys Arg Lys Asn Ala Ser Ile Ser Val Arg Ala
    275                 280                 285
Gln Asp Arg Tyr Tyr Ser Ser Ser Trp Ser Glu Trp Ala Ser Val Pro
290                 295                 300
Cys Ser
305

<210> 7
<211> 1840
<212> DNA
<213> Mus musculus
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 7
gcacatcaga ccaggcagct cgcagcaaag caagatgtgt cctcagaagc taaccatctc    60
ctggtttgcc atcgttttgc tggtgtctcc actcatggcc atgtgggagc tggagaaaga   120
cgtttatgtt gtagaggtgg actggactcc cgatgcccct ggagaaacag tgaacctcac   180
ctgtgacacg cctgaagaag atgacatcac ctggaccctca gaccagagac atggagtcat   240
aggctctgga aagaccctga ccatcactgt caaagagttt ctagatgctg gccagtacac   300
ctgccacaaa ggaggcgaga ctctgagcca ctcacatctg ctgctccaca agaaggaaaa   360
tggaatttgg tccactgaaa ttttaaaaaa tttcaaaaac aagacttttcc tgaagtgtga   420
agcaccaaat tactccggac ggttcacgtg ctcatggctg gtgcaaagaa acatggactt   480
gaagttcaac atcaagagca gtagcagttc cctgactct cgggcagtga catgtggaat   540
ggcgtctctg tctgcagaga aggtcacact ggaccaaagg gactatgaga agtattcagt   600
gtcctgccag gaggatgtca cctgcccaac tgccgaggag accctgccca ttgaactggc   660
gttggaagca cggcagcaga ataaatatga gaactacagc accagcttct tcatcaggga   720
catcatcaaa ccagacccgc ccaagaactt gcagatgaag cctttgaaga actcacaggt   780
ggaggtcagc tgggagtacc ctgactcctg gagcactcc cattcctact tctccctcaa   840
gttctttgtt cgaatccagc gcaagaaaga aagatgaag gagacagagg aggggtgtaa   900
ccagaaaggt gcgttcctcg tagagaagac atctaccgaa gtccaatgca aaggcgggaa   960
tgtctgcgtg caagctcagg atcgctatta caattcctca tgcagcaagt gggcatgtgt  1020
tccctgcagg gtccgatcct aggatgcaac gttggaaagg aaagaaaagt ggaagacatt  1080
aaggaagaaa aatttaaact caggatggaa gagtccccca aaagctgtct tctgcttggt  1140
tggcttttc cagttttcct aagttcatca tgacaccttt gctgattct acatgtaaat  1200
gttaaatgcc cgcagagcca gggagctaat gtatgcatag atattctagc attccacttg  1260
gcctatgct gttgaaatat ttaagtaatt tatgtattta ttaatttatt tctgcatttc  1320
acatttgtat accaagatgt attgaatatt tcatgtgctc gtggcctgat ccactgggac  1380
caggccctat tatgcaaatt gtgagcttgt tatcttcttc aacagctctt caatcagggc  1440
tgcgtaggta cattagcttt tgtgacaacc aataagaaca taatattctg acacaagcag  1500
tgttacatat ttgtgaccag taaagacata ggtggtattt ggagacatga agaagctgta  1560
aagttgactc tgaagagttt agcactagtt tcaacaccaa gaaagacttt ttagaagtga  1620
tattgataag aaaccagggc cttctttaga agggtaccta aatttaaaag aattttgaaa  1680
ggctgggtat cggtggtata tgcttttaat tccagcactc aggagaccaa ggcaggcaga  1740
tctctgtgag tttgaggaca gcctggtgta caggggagt tccagcacag ccagtgccac  1800
acagaaattc tgtctcaaaa acaattaaaa aaaaaaaaa                         1840

<210> 8
<211> 335
<212> PRT
<213> Mus musculus
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 8
Met Cys Pro Gln Lys Leu Thr Ile Ser Trp Phe Ala Ile Val Leu Leu
 1               5                   10                  15
Val Ser Pro Leu Met Ala Met Trp Glu Leu Glu Lys Asp Val Tyr Val
             20                  25                  30
Val Glu Val Asp Trp Thr Pro Asp Ala Pro Gly Glu Thr Val Asn Leu
         35                  40                  45
Thr Cys Asp Thr Pro Glu Glu Asp Asp Ile Thr Trp Thr Ser Asp Gln
     50                  55                  60
Arg His Gly Val Ile Gly Ser Gly Lys Thr Leu Thr Ile Thr Val Lys
65                   70                  75                  80
Glu Phe Leu Asp Ala Gly Gln Tyr Thr Cys His Lys Gly Gly Glu Thr
                 85                  90                  95
Leu Ser His Ser His Leu Leu Leu His Lys Lys Glu Asn Gly Ile Trp
            100                 105                 110
Ser Thr Glu Ile Leu Lys Asn Phe Lys Asn Lys Thr Phe Leu Lys Cys
        115                 120                 125
Glu Ala Pro Asn Tyr Ser Gly Arg Phe Thr Cys Ser Trp Leu Val Gln
    130                 135                 140
Arg Asn Met Asp Leu Lys Phe Asn Ile Lys Ser Ser Ser Ser Ser Pro
145                 150                 155                 160
Asp Ser Arg Ala Val Thr Cys Gly Met Ala Ser Leu Ser Ala Glu Lys
                165                 170                 175
Val Thr Leu Asp Gln Arg Asp Tyr Glu Lys Tyr Ser Val Ser Cys Gln
            180                 185                 190
Glu Asp Val Thr Cys Pro Thr Ala Glu Glu Thr Leu Pro Ile Glu Leu
        195                 200                 205
Ala Leu Glu Ala Arg Gln Gln Asn Lys Tyr Glu Asn Tyr Ser Thr Ser
    210                 215                 220
Phe Phe Ile Arg Asp Ile Ile Lys Pro Asp Pro Pro Lys Asn Leu Gln
225                 230                 235                 240
Met Lys Pro Leu Lys Asn Ser Gln Val Glu Val Ser Trp Glu Tyr Pro
                245                 250                 255
Asp Ser Trp Ser Thr Pro His Ser Tyr Phe Ser Leu Lys Phe Phe Val
            260                 265                 270
Arg Ile Gln Arg Lys Lys Glu Lys Met Lys Glu Thr Glu Glu Gly Cys
        275                 280                 285
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Asn Gln Lys Gly Ala Phe Leu Val Glu Lys Thr Ser Thr Glu Val Gln
    290                 295                 300
Cys Lys Gly Gly Asn Val Cys Val Gln Ala Gln Asp Arg Tyr Tyr Asn
305                 310                 315                 320
Ser Ser Cys Ser Lys Trp Ala Cys Val Pro Cys Arg Val Arg Ser
                325                 330                 335

<210> 9
<211> 1008
<212> DNA
<213> Rattus norvegicus

<400> 9
atgtgtcatc agaagttaac cttctcctgg tttgccatgg ttttgctggt gtctccactc    60
atggccatgt gggagctgga gaaagatgtt tatgttgtag aggtggactg gcgccccgat   120
gccctggag aaacggtgac cctcacctgt gacagtcctg aagaagatga catcacctgg   180
acctcagacc agagacgtgg agtcataggc tctggaaaga ccctgaccat cactgtcaga   240
gagtttctag atgctggcca atacacctgc cacagaggag gcgagactct gagccactca   300
catctgctgc tccacaagaa ggaaatgga atttggtcca ccgagatttt aaaaaatttc   360
aaaaataaga ctttcctgaa gtgtgaagca ccaaactact cggacggtt cacctgctca   420
tggctggtgc acagaaacac ggacttgaag tttaacatca agacagcag cagttccct   480
gagtctcggg cggtgacatg tggacgagca tctctgtctg cagagaaggt cacactgaac   540
caaagggact acgaaagta ctcagtggcg tgccaggagg acgtcacctg cccaactgcc   600
gaggagaccc tgcccattga actggtggtg gaggcccagc agcagaataa atatgagaac   660
tacagcacca gcttcttcat cagggacatc atcaaaccgg acccacccaa gaacctgcag   720
gtgaaacctt tgaagaactc tcaggtggag gtcagctggg agtaccctga ctcctggagc   780
actccccatt cctacttctc cctcaagttc ttcgtccgca tccagcgcaa gaaagaaaag   840
acgaaggaga cagaggagga gtgtaaccag aaaggtgcgt tcctcgtaga gaagacctct   900
gccgaagtcc aatgcaaagg ggcgaatatc tgcgtgcaag cgcaggaccg ctactacaat   960
tcatcatgca gcaaatggac atgtgtaccc tgcaggggcc gatcctaa              1008

<210> 10
<211> 335
<212> PRT
<213> Rattus norvegicus
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 10
Met Cys His Gln Lys Leu Thr Phe Ser Trp Phe Ala Met Val Leu Leu
1               5                   10                  15
Val Ser Pro Leu Met Ala Met Trp Glu Leu Glu Lys Asp Val Tyr Val
            20                  25                  30
Val Glu Val Asp Trp Arg Pro Asp Ala Pro Gly Glu Thr Val Thr Leu
        35                  40                  45
Thr Cys Asp Ser Pro Glu Glu Asp Asp Ile Thr Trp Thr Ser Asp Gln
    50                  55                  60
Arg Arg Gly Val Ile Gly Ser Gly Lys Thr Leu Thr Ile Thr Val Arg
65                  70                  75                  80
Glu Phe Leu Asp Ala Gly Gln Tyr Thr Cys His Arg Gly Gly Glu Thr
                85                  90                  95
Leu Ser His Ser His Leu Leu Leu His Lys Lys Glu Asn Gly Ile Trp
            100                 105                 110
Ser Thr Glu Ile Leu Lys Asn Phe Lys Asn Lys Thr Phe Leu Lys Cys
        115                 120                 125
Glu Ala Pro Asn Tyr Ser Gly Arg Phe Thr Cys Ser Trp Leu Val His
    130                 135                 140
Arg Asn Thr Asp Leu Lys Phe Asn Ile Lys Ser Ser Ser Ser Ser Pro
145                 150                 155                 160
Glu Ser Arg Ala Val Thr Cys Gly Arg Ala Ser Leu Ser Ala Glu Lys
                165                 170                 175
Val Thr Leu Asn Gln Arg Asp Tyr Glu Lys Tyr Ser Val Ala Cys Gln
            180                 185                 190
Glu Asp Val Thr Cys Pro Thr Ala Glu Glu Thr Leu Pro Ile Glu Leu
        195                 200                 205
Val Val Glu Ala Gln Gln Gln Asn Lys Tyr Glu Asn Tyr Ser Thr Ser
    210                 215                 220
Phe Phe Ile Arg Asp Ile Ile Lys Pro Asp Pro Pro Lys Asn Leu Gln
225                 230                 235                 240
Val Lys Pro Leu Lys Asn Ser Gln Val Glu Val Ser Trp Glu Tyr Pro
                245                 250                 255
Asp Ser Trp Ser Thr Pro His Ser Tyr Phe Ser Leu Lys Phe Phe Val
            260                 265                 270
Arg Ile Gln Arg Lys Lys Glu Lys Thr Lys Glu Thr Glu Glu Glu Cys
        275                 280                 285
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Asn Gln Lys Gly Ala Phe Leu Val Glu Lys Thr Ser Ala Glu Val Gln
        290                 295                 300
Cys Lys Gly Ala Asn Ile Cys Val Gln Ala Gln Asp Arg Tyr Tyr Asn
305                 310                 315                 320
Ser Ser Cys Ser Lys Trp Thr Cys Val Pro Cys Arg Gly Arg Ser
                325                 330                 335

<210> 11
<211> 821
<212> DNA
<213> Rattus norvegicus

<400> 11
ctcgcagcag agcaagatgt gtcatcagaa gttaaccttc tcctggtttg ccatggtttt     60
gctggtgtct ccactcatgg ccatgtggga gctggagaaa gatgtttatg ttgtagaggt    120
ggactggcgc cccgatgccc ctggagaaac ggtgaccctc acctgtgaca gtcctgaaga    180
agatgacatc acctggacct cagaccagag acgtggagtc ataggctctg gaaagaccct    240
gaccatcact gtcagagagt ttctagatgc tggccaatac acctgccaca gaggaggcga    300
gactctgagc cactcacatc tgctgctcca caagaaggaa aatggaattt ggtccaccga    360
gattttaaaa aatttcaaaa ataagacttt cctgaagaga gaagcaccaa actactccgg    420
acggttcacc tgctcatggc tggtgcacag aaacacggac ttgaagttta acatcaagag    480
cagcagcagt tccctgagt ctcgggcggt gacatgtgga gcagcatctc tgtctgcaga    540
gaaggtcaca ctgaaccaaa gggactacga gaagtactca gtggcgtgcc aggaggacgt    600
cacctgccca actgccgagg agacctgcc cattgaactg gtggtggagg cccagcagca    660
gaataaatat gagaactaca gcaccagctt cttcatcagg gacatcatca accggaccc    720
acccaagaac ctgcaggtga aacctttgaa gaactctcag gtggaggtca gctgggagta    780
ccctgactcc tggagcactc cccattccta cttctccctc a                        821

<210> 12
<211> 268
<212> PRT
<213> Rattus norvegicus

<400> 12
Met Cys His Gln Lys Leu Thr Phe Ser Trp Phe Ala Met Val Leu Leu
  1                   5                  10                  15
Val Ser Pro Leu Met Ala Met Trp Glu Leu Glu Lys Asp Val Tyr Val
                 20                  25                  30
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Val Glu Val Asp Trp Arg Pro Asp Ala Pro Gly Glu Thr Val Thr Leu
        35                  40                  45
Thr Cys Asp Ser Pro Glu Glu Asp Asp Ile Thr Trp Thr Ser Asp Gln
 50                      55                  60
Arg Arg Gly Val Ile Gly Ser Gly Lys Thr Leu Thr Ile Thr Val Arg
 65                  70                  75                   80
Glu Phe Leu Asp Ala Gly Gln Tyr Thr Cys His Arg Gly Gly Glu Thr
                 85                  90                  95
Leu Ser His Ser His Leu Leu Leu His Lys Lys Glu Asn Gly Ile Trp
             100                 105                 110
Ser Thr Glu Ile Leu Lys Asn Phe Lys Asn Lys Thr Phe Leu Lys Arg
        115                 120                 125
Glu Ala Pro Asn Tyr Ser Gly Arg Phe Thr Cys Ser Trp Leu Val His
        130                 135                 140
Arg Asn Thr Asp Leu Lys Phe Asn Ile Lys Ser Ser Ser Ser Ser Pro
145                 150                 155                 160
Glu Ser Arg Ala Val Thr Cys Gly Ala Ala Ser Leu Ser Ala Glu Lys
                165                 170                 175
Val Thr Leu Asn Gln Arg Asp Tyr Glu Lys Tyr Ser Val Ala Cys Gln
            180                 185                 190
Glu Asp Val Thr Cys Pro Thr Ala Glu Glu Thr Leu Pro Ile Glu Leu
        195                 200                 205
Val Val Glu Ala Gln Gln Gln Asn Lys Tyr Glu Asn Tyr Ser Thr Ser
210                 215                 220
Phe Phe Ile Arg Asp Ile Ile Lys Pro Asp Pro Pro Lys Asn Leu Gln
225                 230                 235                 240
Val Lys Pro Leu Lys Asn Ser Gln Val Glu Val Ser Trp Glu Tyr Pro
                245                 250                 255
Asp Ser Trp Ser Thr Pro His Ser Tyr Phe Ser Leu
            260                 265

<210> 13
<211> 990
<212> DNA
<213> Felis catus
```

UNITED STATES PATENT AND TRADEMARK OFFICE
CERTIFICATE OF CORRECTION

PATENT NO.       : 7,183,382 B2
APPLICATION NO.  : 10/375706
DATED            : February 27, 2007
INVENTOR(S)      : Oppmann et al.

It is certified that error appears in the above-identified patent and that said Letters Patent is hereby corrected as shown below:

```
<400> 13
atgcatcctc agcagctggt catcgcctgg ttttccctgg ttttgctggc acctcccctc     60
atggccatat gggaactgga gaaaaacgtt tatgttgtag agttggactg gcaccctgat    120
gcccccggag aaatggtggt cctcacctgt gacacgcctg aagaagatga catcacctgg    180
acctctgacc agagcagtga agtcctaggc tctggtaaaa ctctgaccat ccaagtcaaa    240
gaatttgcag atgctggcca gtatacctgt cataaaggag gcgaggttct gagccattcg    300
ttcctcctga tacacaaaaa ggaagatgga atttggtcca ctgatatctt aagggaacag    360
aaagaatcca aaaataagat ctttctaaaa tgtgaggcaa agaattattc tggacgtttc    420
acctgctggt ggctgacggc aatcagtacc gatttgaaat tcactgtcaa aagcagcaga    480
ggctcctctg accccaagg ggtgacttgt ggagcagcga cactctcagc agagaaggtc     540
agagtggaca acaggggatta taagaagtac acagtggagt gtcaggaggg cagtgcctgc    600
ccggctgccg aggagagcct accattgaa gtcgtggtgg acgctattca caagctcaag     660
tacgaaaact acaccagcag cttcttcatc agggacatca tcaaaccgga cccacccaag    720
aacctgcaac tgaagccatt aaaaaattct cggcatgtgg aagtgagctg ggaatacccc    780
gacacctgga gcaccacaca ttcctacttc tccttaacat ttggcgtaca ggtccagggg    840
aagaacaaca gagaaaagaa agacagactc tccgtggaca agacctcagc caaggtcgtg    900
tgccacaagg atgccaagat ccgcgtgcaa gccagagacc gctactatag ctcatcctgg    960
agcaactggg catccgtgtc ctgcagttag                                     990

<210> 14
<211> 329
<212> PRT
<213> Felis catus

<400> 14
Met His Pro Gln Gln Leu Val Ile Ala Trp Phe Ser Leu Val Leu Leu
1               5                   10                  15
Ala Pro Pro Leu Met Ala Ile Trp Glu Leu Glu Lys Asn Val Tyr Val
                20                  25                  30
Val Glu Leu Asp Trp His Pro Asp Ala Pro Gly Glu Met Val Val Leu
            35                  40                  45
Thr Cys Asp Thr Pro Glu Glu Asp Asp Ile Thr Trp Thr Ser Asp Gln
        50                  55                  60
Ser Ser Glu Val Leu Gly Ser Gly Lys Thr Leu Thr Ile Gln Val Lys
65                  70                  75                  80
Glu Phe Ala Asp Ala Gly Gln Tyr Thr Cys His Lys Gly Gly Glu Val
                    85                  90                  95
```

Page 17 of 40

UNITED STATES PATENT AND TRADEMARK OFFICE
CERTIFICATE OF CORRECTION

PATENT NO.        : 7,183,382 B2
APPLICATION NO.   : 10/375706
DATED             : February 27, 2007
INVENTOR(S)       : Oppmann et al.

It is certified that error appears in the above-identified patent and that said Letters Patent is hereby corrected as shown below:

```
Leu Ser His Ser Phe Leu Leu Ile His Lys Lys Glu Asp Gly Ile Trp
            100                 105                 110
Ser Thr Asp Ile Leu Arg Glu Gln Lys Glu Ser Lys Asn Lys Ile Phe
        115                 120                 125
Leu Lys Cys Glu Ala Lys Asn Tyr Ser Gly Arg Phe Thr Cys Trp Trp
    130                 135                 140
Leu Thr Ala Ile Ser Thr Asp Leu Lys Phe Thr Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Lys Val Arg Val Asp Asn Arg Asp Tyr Lys Lys Tyr Thr Val
            180                 185                 190
Glu Cys Gln Glu Gly Ser Ala Cys Pro Ala Ala Glu Glu Ser Leu Pro
        195                 200                 205
Ile Glu Val Val Val Asp Ala Ile His Lys Leu Lys Tyr Glu Asn Tyr
    210                 215                 220
Thr Ser Ser Phe Phe Ile Arg Asp Ile Ile Lys Pro Asp Pro Pro Lys
225                 230                 235                 240
Asn Leu Gln Leu Lys Pro Leu Lys Asn Ser Arg His Val Glu Val Ser
                245                 250                 255
Trp Glu Tyr Pro Asp Thr Trp Ser Thr Pro His Ser Tyr Phe Ser Leu
            260                 265                 270
Thr Phe Gly Val Gln Val Gln Gly Lys Asn Asn Arg Glu Lys Lys Asp
        275                 280                 285
Arg Leu Ser Val Asp Lys Thr Ser Ala Lys Val Val Cys His Lys Asp
    290                 295                 300
Ala Lys Ile Arg Val Gln Ala Arg Asp Arg Tyr Tyr Ser Ser Ser Trp
305                 310                 315                 320
Ser Asn Trp Ala Ser Val Ser Cys Ser
                325

<210> 15
<211> 1006
<212> DNA
<213> Felis catus
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 15
atgcatcctc agcagttggt catcgcctgg ctttccctgg ttttgctggc acctcccctc    60
atggccatat gggaactgga gaaaaacgtt tatgttgtag agttggactg gcaccctgat   120
gccccggag aaatggtggt cctcacctgc aatactcctg aagaagatga catcacctgg    180
acctctgacc agagcagtga agtcctaggc tctggtaaaa ctctgaccat ccaagtcaaa   240
gaatttgcag atgctggcca gtatacctgt cataaaggag gcgaggttct gagccattcg   300
ttcctcctga tacacaaaaa ggaagatgga atttggtcca ctgatatctt aagggaacag   360
aaagaatcca aaaataagat cttctaaaa tgtgaggcaa agaattattc tggacgtttc    420
acctgctggt ggctgacggc aatcagtacc gatttgaaat tcactgtcaa aagcagcaga   480
ggctcctctg accccaaga ggtgacttgt ggagcagcga cactctcagc agagaaggtc    540
agagtggaca acagggatta taagaagtac acagtggagt gtcaggaggg cagtgcctgc   600
ccggctgccg aggagagcct acccattgaa gtcgtggtgg acgctattca caagctcaag   660
tacgaaaact acaccagcag cttcttcatc agggacatca tcaaaccgga cccacccaag   720
aacctgcaac tgaagccatt aaaaaattct cggcatgtgg aagtgagctg ggaataccct   780
gacacctgga gcaccccaca ttcctacttc tccttaacat ttggcgtaca ggtccagggc   840
aagaacaaca gagaaaagaa agacagactc tccgtggaaa agacctcagc caaggtcgtg   900
tgccacaagg atgccaagat ccgcgtgcaa gccagagacc gctactatag ctcatcctgg   960
agcaactggg catccgtgtc ctgcagttag gttccacccc caggat             1006

<210> 16
<211> 329
<212> PRT
<213> Felis catus

<400> 16
Met His Pro Gln Gln Leu Val Ile Ala Trp Leu Ser Leu Val Leu Leu
  1               5                  10                  15
Ala Pro Pro Leu Met Ala Ile Trp Glu Leu Glu Lys Asn Val Tyr Val
                 20                  25                  30
Val Glu Leu Asp Trp His Pro Asp Ala Pro Gly Glu Met Val Val Leu
             35                  40                  45
Thr Cys Asn Thr Pro Glu Glu Asp Ile Thr Trp Thr Ser Asp Gln
         50                  55                  60
Ser Ser Glu Val Leu Gly Ser Gly Lys Thr Leu Thr Ile Gln Val Lys
 65                  70                  75                  80
Glu Phe Ala Asp Ala Gly Gln Tyr Thr Cys His Lys Gly Gly Glu Val
                 85                  90                  95
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Leu Ser His Ser Phe Leu Leu Ile His Lys Lys Glu Asp Gly Ile Trp
            100                 105                 110
Ser Thr Asp Ile Leu Arg Glu Gln Lys Glu Ser Lys Asn Lys Ile Phe
        115                 120                 125
Leu Lys Cys Glu Ala Lys Asn Tyr Ser Gly Arg Phe Thr Cys Trp Trp
    130                 135                 140
Leu Thr Ala Ile Ser Thr Asp Leu Lys Phe Thr Val Lys Ser Ser Arg
145                 150                 155                 160
Gly Ser Ser Asp Pro Gln Glu Val Thr Cys Gly Ala Ala Thr Leu Ser
                165                 170                 175
Ala Glu Lys Val Arg Val Asp Asn Arg Asp Tyr Lys Lys Tyr Thr Val
            180                 185                 190
Glu Cys Gln Glu Gly Ser Ala Cys Pro Ala Ala Glu Glu Ser Leu Pro
        195                 200                 205
Ile Glu Val Val Val Asp Ala Ile His Lys Leu Lys Tyr Glu Asn Tyr
    210                 215                 220
Thr Ser Ser Phe Phe Ile Arg Asp Ile Ile Lys Pro Asp Pro Pro Lys
225                 230                 235                 240
Asn Leu Gln Leu Lys Pro Leu Lys Asn Ser Arg His Val Glu Val Ser
                245                 250                 255
Trp Glu Tyr Pro Asp Thr Trp Ser Thr Pro His Ser Tyr Phe Ser Leu
            260                 265                 270
Thr Phe Gly Val Gln Val Gln Gly Lys Asn Asn Arg Glu Lys Lys Asp
        275                 280                 285
Arg Leu Ser Val Asp Lys Thr Ser Ala Lys Val Val Cys His Lys Asp
    290                 295                 300
Ala Lys Ile Arg Val Gln Ala Arg Asp Arg Tyr Tyr Ser Ser Ser Trp
305                 310                 315                 320
Ser Asn Trp Ala Ser Val Ser Cys Ser
                325

<210> 17
<211> 1058
<212> DNA
<213> Equus caballus
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 17
atgtgtcacc agtggttggt cctctcctgg ttttccctgg ttttgctggc gtctcccctc      60
atggccatat gggaactgga gaaagatgtg tatgttgtag aattggattg gtaccctgat     120
gccctggag aaatggtggt cctcacctgc aataccctg aagaagaagg catcacctgg      180
acctcggccc agagcaatga ggtcttaggc tctggcaaaa ccttgaccat ccaagtcaaa     240
gagtttggag atgctggctg gtacacctgt cacaaaggag gcgaggttct gagccattct    300
cacctgctgc ttcacaagaa ggaagatgga atttggtcca ctgacatttt aaaagaccag    360
aagaatcca aaaataagac ctttctaaaa tgtgaggcaa agaattattc cggacgtttc     420
acatgctggt ggctgacagc aatcagtact gatttgaaat tcagtgtcaa aagcagcaga    480
ggttcctctg acccccgagg ggtgacgtgt ggagcagcga cactctccgc agagagggtc    540
agcgtggacg acaggagta taagaagtac acggtggagt gtcaggaggg cagtgcctgc    600
cggccgccg aggagagcct gcccattgag atcgtggtgg atgctgttca caagctcaag    660
tatgaaaact acaccagcgg cttcttcatc agggacatca tcaaaccaga cccacccaag    720
aacctgcagc tgaagccatt aaagaattct cggcagctg aggtcagctg ggagtaccc     780
gagacctgga gcaccccaca ttcctactc tccctgacat tctctattca ggtccagggc    840
aagaacaaga aggaaaggaa agacagactc ttcatggatg agacttcagc cacagtcaca    900
tgccacaagg atggccagat ccgtgtccaa gccagggacc gctactacag ctcatcctgg    960
agcgaatggg catccgtatc ctgcagttag ggatgcagac tcaggcagcc caggccagac   1020
ctgaacactc agtgtaccca ggtctaacc tcagtatg                             1058

<210> 18
<211> 329
<212> PRT
<213> Equus caballus

<400> 18
Met Cys His Gln Trp Leu Val Leu Ser Trp Phe Ser Leu Val Leu Leu
1               5                   10                  15
Ala Ser Pro Leu Met Ala Ile Trp Glu Leu Glu Lys Asp Val Tyr Val
                20                  25                  30
Val Glu Leu Asp Trp Tyr Pro Asp Ala Pro Gly Glu Met Val Val Leu
            35                  40                  45
Thr Cys Asn Thr Pro Glu Glu Glu Gly Ile Thr Trp Thr Ser Ala Gln
        50                  55                  60
Ser Asn Glu Val Leu Gly Ser Gly Lys Thr Leu Thr Ile Gln Val Lys
65                  70                  75                  80
Glu Phe Gly Asp Ala Gly Trp Tyr Thr Cys His Lys Gly Gly Glu Val
                85                  90                  95
```

Page 21 of 40

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Leu Ser His Ser His Leu Leu Leu His Lys Lys Glu Asp Gly Ile Trp
            100             105                     110
Ser Thr Asp Ile Leu Lys Asp Gln Lys Glu Ser Lys Asn Lys Thr Phe
            115             120             125
Leu Lys Cys Glu Ala Lys Asn Tyr Ser Gly Arg Phe Thr Cys Trp Trp
    130             135                     140
Leu Thr Ala Ile Ser Thr Asp Leu Lys Phe Ser Val Lys Ser Ser Arg
145             150                     155                     160
Gly Ser Ser Asp Pro Arg Gly Val Thr Cys Gly Ala Ala Thr Leu Ser
                165             170                     175
Ala Glu Arg Val Ser Val Asp Asp Arg Glu Tyr Lys Lys Tyr Thr Val
            180                     185                 190
Glu Cys Gln Glu Gly Ser Ala Cys Pro Ala Ala Glu Glu Ser Leu Pro
            195             200             205
Ile Glu Ile Val Val Asp Ala Val His Lys Leu Lys Tyr Glu Asn Tyr
    210             215             220
Thr Ser Gly Phe Phe Ile Arg Asp Ile Ile Lys Pro Asp Pro Pro Lys
225             230             235                     240
Asn Leu Gln Leu Lys Pro Leu Lys Asn Ser Arg Gln Val Glu Val Ser
            245             250             255
Trp Glu Tyr Pro Asp Thr Trp Ser Thr Pro His Ser Tyr Phe Ser Leu
            260             265             270
Thr Phe Ser Ile Gln Val Gln Gly Lys Asn Lys Lys Glu Arg Lys Asp
        275             280             285
Arg Leu Phe Met Asp Glu Thr Ser Ala Thr Val Thr Cys His Lys Asp
        290             295             300
Gly Gln Ile Arg Val Gln Ala Arg Asp Arg Tyr Tyr Ser Ser Ser Trp
305             310             315                     320
Ser Glu Trp Ala Ser Val Ser Cys Ser
                325

<210> 19
<211> 1399
<212> DNA
<213> Homo sapiens
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 19
ctgtttcagg gccattggac tctccgtcct gcccagagca agatgtgtca ccagcagttg    60
gtcatctctt ggttttccct ggttttctg gcatctcccc tcgtggccat atgggaactg    120
aagaaagatg tttatgtcgt agaattggat tggtatccgg atgccctgg agaaatggtg    180
gtcctcacct gtgacacccc tgaagaagat ggtatcacct ggaccttgga ccagagcagt   240
gaggtcttag gctctggcaa aaccctgacc atccaagtca aagagtttgg agatgctggc   300
cagtacacct gtcacaaagg aggcgaggtt ctaagccatt cgctcctgct gcttcacaaa   360
aaggaagatg gaatttggtc cactgatatt ttaaaggacc agaaagaacc caaaaataag   420
acctttctaa gatgcgaggc caagaattat tctggacgtt tcacctgctg gtggctgacg   480
acaatcagta ctgatttgac attcagtgtc aaaagcagca gaggctcttc tgacccccaa   540
ggggtgacgt gcggagctgc tacactctct gcagagagag tcagagggga caacaaggag   600
tatgagtact cagtggagtg ccaggaggac agtgcctgcc cagctgctga ggagagtctg   660
cccattgagg tcatggtgga tgccgttcac aagctcaagt atgaaaacta caccagcagc   720
ttcttcatca gggacatcat caaacctgac ccaccaaaga acttgcagct gaagccatta   780
aagaattctc ggcaggtgga ggtcagctgg gagtaccctg acacctggag tactccacat   840
tcctacttct ccctgacatt ctgcgttcag gtccagggca agagcaagag agaaaagaaa   900
gatagagtct tcacggacaa gacctcagcc acggtcatct gccgcaaaaa tgccagcatt   960
agcgtgcggg cccaggaccg ctactatagc tcatcttgga gcgaatgggc atctgtgccc   1020
tgcagttagg ttctgatcca ggatgaaaat ttggaggaaa agtggaagat attaagcaaa   1080
atgtttaaag acacaacgga atagacccaa aaagataatt tctatctgat ttgctttaaa   1140
acgtttttttt aggatcacaa tgatatcttt gctgtatttg tatagttaga tgctaaatgc   1200
tcattgaaac aatcagctaa tttatgtata gatttttccag ctctcaagtt gccatgggcc   1260
ttcatgctat ttaaatattt aagtaattta tgtatttatt agtatattac tgttatttaa   1320
cgtttgtctg ccaggatgta tggaatgttt catactctta tgacctgatc catcaggatc   1380
agtccctatt atgcaaaat                                                1399

<210> 20
<211> 328
<212> PRT
<213> Homo sapiens

<400> 20
Met Cys His Gln Gln Leu Val Ile Ser Trp Phe Ser Leu Val Phe Leu
 1               5                   10                  15
Ala Ser Pro Leu Val Ala Ile Trp Glu Leu Lys Lys Asp Val Tyr Val
            20                  25                  30
Val Glu Leu Asp Trp Tyr Pro Asp Ala Pro Gly Glu Met Val Val Leu
        35                  40                  45
```

Page 23 of 40

UNITED STATES PATENT AND TRADEMARK OFFICE
CERTIFICATE OF CORRECTION

| | |
|---|---|
| PATENT NO. | : 7,183,382 B2 |
| APPLICATION NO. | : 10/375706 |
| DATED | : February 27, 2007 |
| INVENTOR(S) | : Oppmann et al. |

It is certified that error appears in the above-identified patent and that said Letters Patent is hereby corrected as shown below:

```
Thr Cys Asp Thr Pro Glu Glu Asp Gly Ile Thr Trp Thr Leu Asp Gln
        50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Val
                85                  90                  95
Leu Ser His Ser Leu Leu Leu Leu His Lys Lys Glu Asp Gly Ile Trp
                100                 105                 110
Ser Thr Asp Ile Leu Lys Asp Gln Lys Glu Pro Lys Asn Lys Thr Phe
        115                 120                 125
Leu Arg Cys Glu Ala Lys Asn Tyr Ser Gly Arg Phe Thr Cys Trp Trp
    130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Asn Lys Glu Tyr Glu Tyr Ser Val Glu
                180                 185                 190
Cys Gln Glu Asp Ser Ala Cys Pro Ala Ala Glu Glu Ser Leu Pro Ile
        195                 200                 205
Glu Val Met Val Asp Ala Val His Lys Leu Lys Tyr Glu Asn Tyr Thr
        210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
            260                 265                 270
Phe Cys Val Gln Val Gln Gly Lys Ser Lys Arg Glu Lys Lys Asp Arg
        275                 280                 285
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser
                325
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<210> 21
<211> 1012
<212> DNA
<213> Capra hircus

<400> 21
atgcaccctc agcagttggt cgtttcctgg ttttccctgg ttttgctggc atctcccatc      60
gtggccatat gggaactgga gaaaaatgtt tatgttgtag aattggattg gtatcctaat     120
gctcctggag aaacagtggt cctcacgtgt gacactcctg aagaagacgg catcacctgg     180
acctcagacc agagcagtga ggtcctgggc tctggcaaaa ccttgaccat ccaagtcaaa     240
gagtttggag atgctgggca gtacacctgt cacaaaggag gcgaggttct gagtcgttca     300
ctcctcctgc ttcacaaaaa ggaagatgga atttggtcca ctgatatttt aaaggatcag     360
aaagaaccca aagctaagag ttttttaaaa tgtgaggcaa aggattattc tggacacttc     420
acctgctcgt ggctgacagc aatcagtact aatctgaaat tcagtgtcaa aagcagcaga     480
ggctcctctg accccgagg ggtgacgtgc ggagcagcgt cactctcagc agagaaggtc      540
agcatggacc acagggagta taacaagtac acagtggagt gtcaggaggg cagtgcctgc     600
ccggccgccg aggagagcct gcccattgag gtcgtgatgg aagctgtgca caagctcaag     660
tatgaaaact acaccagcag cttcttcatc agggacatca tcaaaccaga cccacccaag     720
aacctgcaac tgagaccact aaagaattct cggcaggtgg aggtcagctg ggagtaccct     780
gacacgtgga gcaccccaca ttcctacttc tccctgacgt tttgtgttca ggtccaggga     840
aagaacaaga gagaaaagaa actcttcacg gaccaaacct cagccaaagt cacatgccac     900
aaggatgcca acatccgtgt gcaagcccgg gaccgctact acagctcatt ctggagtgaa     960
tgggcatctg tgtcctgcag ttaggttcta acctcagtat gaaacctcag ag            1012

<210> 22
<211> 327
<212> PRT
<213> Capra hircus

<400> 22
Met His Pro Gln Gln Leu Val Val Ser Trp Phe Ser Leu Val Leu Leu
 1               5                   10                  15
Ala Ser Pro Ile Val Ala Ile Trp Glu Leu Glu Lys Asn Val Tyr Val
                20                  25                  30
Val Glu Leu Asp Trp Tyr Pro Asn Ala Pro Gly Glu Thr Val Val Leu
            35                  40                  45
Thr Cys Asp Thr Pro Glu Glu Asp Gly Ile Thr Trp Thr Ser Asp Gln
        50                  55                  60
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Ser Ser Glu Val Leu Gly Ser Gly Lys Thr Leu Thr Ile Gln Val Lys
 65              70              75                   80
Glu Phe Gly Asp Ala Gly Gln Tyr Thr Cys His Lys Gly Gly Glu Val
             85              90              95
Leu Ser Arg Ser Leu Leu Leu Leu His Lys Lys Glu Asp Gly Ile Trp
            100             105             110
Ser Thr Asp Ile Leu Lys Asp Gln Lys Glu Pro Lys Ala Lys Ser Phe
            115             120             125
Leu Lys Cys Glu Ala Lys Asp Tyr Ser Gly His Phe Thr Cys Ser Trp
        130             135             140
Leu Thr Ala Ile Ser Thr Asn Leu Lys Phe Ser Val Lys Ser Ser Arg
145             150             155                  160
Gly Ser Ser Asp Pro Arg Gly Val Thr Cys Gly Ala Ala Ser Leu Ser
                165             170             175
Ala Glu Lys Val Ser Met Asp His Arg Glu Tyr Asn Lys Tyr Thr Val
            180             185             190
Glu Cys Gln Glu Gly Ser Ala Cys Pro Ala Ala Glu Glu Ser Leu Pro
            195             200             205
Ile Glu Val Val Met Glu Ala Val His Lys Leu Lys Tyr Glu Asn Tyr
        210             215             220
Thr Ser Ser Phe Phe Ile Arg Asp Ile Ile Lys Pro Asp Pro Pro Lys
225             230             235                  240
Asn Leu Gln Leu Arg Pro Leu Lys Asn Ser Arg Gln Val Glu Val Ser
                245             250             255
Trp Glu Tyr Pro Asp Thr Trp Ser Thr Pro His Ser Tyr Phe Ser Leu
            260             265             270
Thr Phe Cys Val Gln Val Gln Gly Lys Asn Lys Arg Glu Lys Lys Leu
            275             280             285
Phe Thr Asp Gln Thr Ser Ala Lys Val Thr Cys His Lys Asp Ala Asn
        290             295             300
Ile Arg Val Gln Ala Arg Asp Arg Tyr Tyr Ser Ser Phe Trp Ser Glu
305             310             315                  320
Trp Ala Ser Val Ser Cys Ser
                325

<210> 23
<211> 1080
<212> DNA
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<213> Macaca mulatta

<400> 23
gcccagagca agatgtgtca ccagcagctg gtcatctctt ggttttccct ggtttttctg      60
gcatctcccc tcatggccat atgggaactg aagaaagacg tttatgttgt agaattggac     120
tggtaccegg atgccectgg agaaatggtg gtcctcacct gtgacacccc tgaagaagat    180
ggtatcacct ggaccttgga ccagagtggt gaggtcttag gctctggcaa aacccigacc    240
atccaagtca aagagtttgg agatgctggc cagtacacct gtcacaaagg aggcgaggct    300
ctaagccatt cactcctgct gcttcacaaa aaggaagatg gaatttggtc cactgatgtt    360
ttaaaggacc agaaagaacc caaaaataag acctttctaa gatgtgaggc aaaaattat     420
tctggacgtt tcacctgctg gtggctgacg acaatcagta ctgatctgac attcagtgtc    480
aaaagcagca gaggctcttc taaccccaa ggggtgacgt gtggagccgt tacactctct     540
gcagagaggg tcagagggga caataaggag tatgagtact cagtggagtg ccaggaggac    600
agtgcctgcc cagccgctga ggagaggctg cccattgagg tcatggtgga tgccattcac    660
aagctcaagt atgaaaacta caccagcagc ttcttcatca gggacatcat caaacccgac    720
ccaccaagaa acttgcagct gaagccatta aagaattctc ggcaggtgga ggtcagctgg    780
gagtaccctg acacctggag tactccacat tcctacttct ccctgacatt ctgcatccag    840
gtccaggca agagcaagag agaaaagaaa gatagaatct tcacagacaa gacctcagcc    900
acggtcatct gccgcaaaaa tgccagcttt agcgtgcagg cccaggaccg ctactatagc   960
tcatcttgga gcgaatgggc atctgtgccc tgcagttagg ttgtgatccc aggatgaaaa   1020
attggaggaa aagtagaaga tattaaccaa aacgtttaaa gacacaacgg aatagaccca   1080

<210> 24
<211> 328
<212> PRT
<213> Macaca mulatta

<400> 24
Met Cys His Gln Gln Leu Val Ile Ser Trp Phe Ser Leu Val Phe Leu
 1               5                  10                  15
Ala Ser Pro Leu Met Ala Ile Trp Glu Leu Lys Lys Asp Val Tyr Val
            20                  25                  30
Val Glu Leu Asp Trp Tyr Pro Asp Ala Pro Gly Glu Met Val Val Leu
        35                  40                  45
Thr Cys Asp Thr Pro Glu Glu Asp Gly Ile Thr Trp Thr Leu Asp Gln
    50                  55                  60
Ser Gly Glu Val Leu Gly Ser Gly Lys Thr Leu Thr Ile Gln Val Lys
65                  70                  75                  80
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Glu Phe Gly Asp Ala Gly Gln Tyr Thr Cys His Lys Gly Gly Glu Ala
                 85              90              95
Leu Ser His Ser Leu Leu Leu Leu His Lys Lys Glu Asp Gly Ile Trp
             100             105             110
Ser Thr Asp Val Leu Lys Asp Gln Lys Glu Pro Lys Asn Lys Thr Phe
         115             120             125
Leu Arg Cys Glu Ala Lys Asn Tyr Ser Gly Arg Phe Thr Cys Trp Trp
     130             135             140
Leu Thr Thr Ile Ser Thr Asp Leu Thr Phe Ser Val Lys Ser Ser Arg
145             150             155             160
Gly Ser Ser Asn Pro Gln Gly Val Thr Cys Gly Ala Val Thr Leu Ser
                 165             170             175
Ala Glu Arg Val Arg Gly Asp Asn Lys Glu Tyr Glu Tyr Ser Val Glu
             180             185             190
Cys Gln Glu Asp Ser Ala Cys Pro Ala Ala Glu Glu Arg Leu Pro Ile
         195             200             205
Glu Val Met Val Asp Ala Ile His Lys Leu Lys Tyr Glu Asn Tyr Thr
     210             215             220
Ser Ser Phe Phe Ile Arg Asp Ile Ile Lys Pro Asp Pro Pro Lys Asn
225             230             235             240
Leu Gln Leu Lys Pro Leu Lys Asn Ser Arg Gln Val Glu Val Ser Trp
                 245             250             255
Glu Tyr Pro Asp Thr Trp Ser Thr Pro His Ser Tyr Phe Ser Leu Thr
             260             265             270
Phe Cys Ile Gln Val Gln Gly Lys Ser Lys Arg Glu Lys Lys Asp Arg
         275             280             285
Ile Phe Thr Asp Lys Thr Ser Ala Thr Val Ile Cys Arg Lys Asn Ala
     290             295             300
Ser Phe Ser Val Gln Ala Gln Asp Arg Tyr Tyr Ser Ser Ser Trp Ser
305             310             315             320
Glu Trp Ala Ser Val Pro Cys Ser
                 325

<210> 25
<211> 1012
<212> DNA
<213> Bos taurus
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 25
atgcaccctc agcagttggt cgttcctgg ttttccctgg ttttgctggc atctcccatc      60
gtggccatgt gggaactgga gaaaaatgtt tatgttgtag aattggattg gtatcctgat    120
gctcctggag aaacagtggt cctcacatgt gacactcctg aagaagatgg catcacctgg    180
acctcagacc agagcagtga ggtcttgggc tctggcaaaa ccttgaccat ccaagtcaaa    240
gagtttggag atgctgggca gtacacctgt cacaaggag gcgaggctct gagtcgttca    300
ctcctcctgc tgcacaaaaa ggaagatgga atttggtcca ctgatatttt aaaggatcag    360
aaagaaccca aagctaagag ttttttaaaa tgtgaggcaa aggattattc tggacacttc    420
acctgctggt ggctgacagc aatcagtact gatttgaaat tcagtgtcaa aagcagcaga    480
ggctcctctg acccccgagg ggtgacgtgc ggagcagcgt tgctctcagc agagaaggtc    540
agcttggagc acagggagta taacaagtac acagtggagt gtcaggaggg cagcgcctgc    600
ccagcagctg aggagagcct gcttattgag gtcgtggtag aagctgtgca caagctcaag    660
tatgaaaact acaccagcag cttcttcatc agggacatca tcaaaccaga cccacccaag    720
aacctgcaac tgagaccatt aaagaattct cggcaggtgg aggtcagctg ggagtaccct    780
gacacgtgga gcacccgca ttcctacttc tccctgacgt tttgtgttca ggtccaggga    840
aagaacaaga gagaaaagaa actcttcatg gaccaaaacct cagccaaagt cacatgccac    900
aaggatgcca acgtcgcgt gcaagccgg gaccgctact acagctcatt ctggagtgaa    960
tgggcatctg tgtcctgcag ttaggttcta acctcagtat gaaacctcag ag          1012

<210> 26
<211> 327
<212> PRT
<213> Bos taurus

<400> 26
Met His Pro Gln Gln Leu Val Val Ser Trp Phe Ser Leu Val Leu Leu
1               5                   10                  15
Ala Ser Pro Ile Val Ala Met Trp Glu Leu Glu Lys Asn Val Tyr Val
            20                  25                  30
Val Glu Leu Asp Trp Tyr Pro Asp Ala Pro Gly Glu Thr Val Val Leu
        35                  40                  45
Thr Cys Asp Thr Pro Glu Glu Asp Gly Ile Thr Trp Thr Ser Asp Gln
    50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Ala
                85                  90                  95
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Leu Ser Arg Ser Leu Leu Leu Leu His Lys Lys Glu Asp Gly Ile Trp
            100                 105                 110
Ser Thr Asp Ile Leu Lys Asp Gln Lys Glu Pro Lys Ala Lys Ser Phe
            115                 120                 125
Leu Lys Cys Glu Ala Lys Asp Tyr Ser Gly His Phe Thr Cys Trp Trp
            130                 135                 140
Leu Thr Ala Ile Ser Thr Asp Leu Lys Phe Ser Val Lys Ser Ser Arg
145                     150                 155                 160
Gly Ser Ser Asp Pro Arg Gly Val Thr Cys Gly Ala Ala Leu Leu Ser
                165                 170                 175
Ala Glu Lys Val Ser Leu Glu His Arg Glu Tyr Asn Lys Tyr Thr Val
            180                 185                 190
Glu Cys Gln Glu Gly Ser Ala Cys Pro Ala Ala Glu Glu Ser Leu Leu
            195                 200                 205
Ile Glu Val Val Val Glu Ala Val His Lys Leu Lys Tyr Glu Asn Tyr
            210                 215                 220
Thr Ser Ser Phe Phe Ile Arg Asp Ile Ile Lys Pro Asp Pro Pro Lys
225                     230                 235                 240
Asn Leu Gln Leu Arg Pro Leu Lys Asn Ser Arg Gln Val Glu Val Ser
                245                 250                 255
Trp Glu Tyr Pro Asp Thr Trp Ser Thr Pro His Ser Tyr Phe Ser Leu
            260                 265                 270
Thr Phe Cys Val Gln Val Gln Gly Lys Asn Lys Arg Glu Lys Lys Leu
            275                 280                 285
Phe Met Asp Gln Thr Ser Ala Lys Val Thr Cys His Lys Asp Ala Asn
            290                 295                 300
Val Arg Val Gln Ala Arg Asp Arg Tyr Tyr Ser Ser Phe Trp Ser Glu
305                     310                 315                 320
Trp Ala Ser Val Ser Cys Ser
                325

<210> 27
<211> 993
<212> DNA
<213> Cervus elaphus
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 27
atgcaccctc agcagttggt cgtttcctgg ttttccctgg ttttgctgac atctcccatt      60
gtggccatat gggaactgga gaaaaatgtt tatgttgtag aattggattg gtatcctgat     120
gctcctggag aaacggtggt cctcaggtgt gacactcctg aagaagacgg tatcacctgg     180
acctcagacc agagcagtga ggtcttgggc tctggcaaaa ccttgaccgt ccaagtcaaa     240
gagtttggag atgctgggca gtacacctgt cacaaaggag gcgaggttct gagtcgttca     300
ctcctcctgc tgcacaaaaa ggaagatgga atttggtcta ctgatatttt aaaggatcag     360
aaagaaccca aagccaagag ttttttaaaa tgtgaggcaa aggattattc tggacacttc     420
acctgctggt ggctgacagc aatcagtact gatttgaaat tcagtgtcaa aagcagcaga     480
ggctcctctg accccgagg ggtgacgtgc ggagcagcgt cgctctcaac agagaaggtc     540
attgtggacc acagggagta taagaagtac acagtggagt gtcaagaggg cagcgcctgc     600
ccggccgccg aggagagcct gcccattgag gtcgtagtgg aagctgtgca caagctcaag     660
tatgaaaact acaccagcag cttcttcatc agggacatca tcaaaccaga cccacccaag     720
aacctgcaac tgagaccatt aaagaattct cggcaggtgg aggtcagctg ggagtaccct     780
gacacgtgga gcaccccaca ttcctacttc tccctgacgt tttgtgttca ggtccaggga     840
aagaacaaga gagaaaagaa actcttcatg gaccaaacct cagccaaagt cacgtgtcac     900
aaggatgcca gcatccgcgt gcaagccggg gaccgctact acaactcatt ctggagtgaa     960
tgggcatctg tgtcctgcag ttaggttcta acc                                   993

<210> 28
<211> 327
<212> PRT
<213> Cervus elaphus

<400> 28
Met His Pro Gln Gln Leu Val Val Ser Trp Phe Ser Leu Val Leu Leu
  1               5                  10                  15
Thr Ser Pro Ile Val Ala Ile Trp Glu Leu Glu Lys Asn Val Tyr Val
             20                  25                  30
Val Glu Leu Asp Trp Tyr Pro Asp Ala Pro Gly Glu Thr Val Val Leu
         35                  40                  45
Arg Cys Asp Thr Pro Glu Glu Asp Gly Ile Thr Trp Thr Ser Asp Gln
     50                  55                  60
Ser Ser Glu Val Leu Gly Ser Gly Lys Thr Leu Thr Val Gln Val Lys
 65                  70                  75                  80
Glu Phe Gly Asp Ala Gly Gln Tyr Thr Cys His Lys Gly Gly Glu Val
                 85                  90                  95
```

Page 31 of 40

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Leu Ser Arg Ser Leu Leu Leu Leu His Lys Lys Glu Asp Gly Ile Trp
            100                 105                 110
Ser Thr Asp Ile Leu Lys Asp Gln Lys Glu Pro Lys Ala Lys Ser Phe
            115                 120                 125
Leu Lys Cys Glu Ala Lys Asp Tyr Ser Gly His Phe Thr Cys Trp Trp
            130                 135                 140
Leu Thr Ala Ile Ser Thr Asp Leu Lys Phe Ser Val Lys Ser Ser Arg
145                 150                 155                 160
Gly Ser Ser Asp Pro Arg Gly Val Thr Cys Gly Ala Ala Ser Leu Ser
            165                 170                 175
Thr Glu Lys Val Ile Val Asp His Arg Glu Tyr Lys Lys Tyr Thr Val
            180                 185                 190
Glu Cys Gln Glu Gly Ser Ala Cys Pro Ala Ala Glu Glu Ser Leu Pro
            195                 200                 205
Ile Glu Val Val Val Glu Ala Val His Lys Leu Lys Tyr Glu Asn Tyr
            210                 215                 220
Thr Ser Ser Phe Phe Ile Arg Asp Ile Ile Lys Pro Asp Pro Pro Lys
225                 230                 235                 240
Asn Leu Gln Leu Arg Pro Leu Lys Asn Ser Arg Gln Val Glu Val Ser
            245                 250                 255
Trp Glu Tyr Pro Asp Thr Trp Ser Thr Pro His Ser Tyr Phe Ser Leu
            260                 265                 270
Thr Phe Cys Val Gln Val Gln Gly Lys Asn Lys Arg Glu Lys Lys Leu
            275                 280                 285
Phe Met Asp Gln Thr Ser Ala Lys Val Thr Cys His Lys Asp Ala Ser
            290                 295                 300
Ile Arg Val Gln Ala Arg Asp Arg Tyr Tyr Asn Ser Phe Trp Ser Glu
305                 310                 315                 320
Trp Ala Ser Val Ser Cys Ser
                325

<210> 29
<211> 984
<212> DNA
<213> Ovis aries
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 29
atgcaccctc agcagttggt cgtttcctgg ttttcnctgg ttttgctggc atcgcccatc        60
gtggccatat gggaactgga gaaaaatgtt tatgttgtag aattggattg gtatcctaat       120
gctcctggag aaacagtggt cctcacgtgt gacactcctg aagaagacgg catcacctgg       180
acctcagacc agagcagtga ggtcctgggc tctggcaaaa ccttgaccat ccaagtcaaa       240
gagtttggag atgctgggca gtacacctgt cacaaaggag gcgaggttct gagtcgttca       300
ctcctcctgc tgcacaaaaa ggaagatgga atttggtcca ctgatatttt aaaggatcag       360
aaagaaccca aagctaagag tttrttaaaa tgtgaggcaa aggattattc tggacacttc       420
acctgctcgt ggctgacagc aatcagtact aatctgaaat tcagtgtcaa aagcagcaga       480
ggctcctctg accccgagg ggtgacgtgc ggagcagcgt ccctctcagc agagaaggtc        540
agcatggacc acagggagta taacaagtac acagtggagt gtcaggaggg cagtgcctgc       600
ccggccgccg aggagagcct gcccattgag gtcgtgatgc aagctgtgca caagctcaag       660
tatgaaaact acaccagcag cttcttcatc agggacatca tcaaaccaga cccacccaag       720
aacctgcaac tgagaccact aaagaattct cggcaggtgg aagtcagctg ggagtaccct       780
gacacgtgga gcacccaca ttcctacttc tccctgacgt tttgtgttca ggtccaggga       840
aagaacaaga gagaaaagaa actcttcaca gaccaaacct cagccasagt cacatgccac       900
aaggatgcca acatccgcgt gcaagcccgg gaccgctact acagctcatt ctggagtgaa       960
tgggcatctg tgtcctgcag ttag                                             984

<210> 30
<211> 327
<212> PRT
<213> Ovis aries

<400> 30
Met His Pro Gln Gln Leu Val Val Ser Trp Phe Ser Leu Val Leu Leu
1               5                  10                  15
Ala Ser Pro Ile Val Ala Ile Trp Glu Leu Glu Lys Asn Val Tyr Val
            20                  25                  30
Val Glu Leu Asp Trp Tyr Pro Asn Ala Pro Gly Glu Thr Val Val Leu
        35                  40                  45
Thr Cys Asp Thr Pro Glu Glu Asp Gly Ile Thr Trp Thr Ser Asp Gln
    50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Glu Val
                85                  90                  95
```

Page 33 of 40

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
        Leu Ser Arg Ser Leu Leu Leu Leu His Lys Lys Glu Asp Gly Ile Trp
                    100                 105                 110
        Ser Thr Asp Ile Leu Lys Asp Gln Lys Glu Pro Lys Ala Lys Ser Phe
                    115                 120                 125
        Leu Lys Cys Glu Ala Lys Asp Tyr Ser Gly His Phe Thr Cys Ser Trp
                    130                 135                 140
        Leu Thr Ala Ile Ser Thr Asn Leu Lys Phe Ser Val Lys Ser Ser Arg
        145                 150                 155                 160
        Gly Ser Ser Asp Pro Arg Gly Val Thr Cys Gly Ala Ala Ser Leu Ser
                    165                 170                 175
        Ala Glu Lys Val Ser Met Asp His Arg Glu Tyr Asn Lys Tyr Thr Val
                    180                 185                 190
        Glu Cys Gln Glu Gly Ser Ala Cys Pro Ala Ala Glu Glu Ser Leu Pro
                    195                 200                 205
        Ile Glu Val Val Met Glu Ala Val His Lys Leu Lys Tyr Glu Asn Tyr
                    210                 215                 220
        Thr Ser Ser Phe Phe Ile Arg Asp Ile Ile Lys Pro Asp Pro Pro Lys
        225                 230                 235                 240
        Asn Leu Gln Leu Arg Pro Leu Lys Asn Ser Arg Gln Val Glu Val Ser
                    245                 250                 255
        Trp Glu Tyr Pro Asp Thr Trp Ser Thr Pro His Ser Tyr Phe Ser Leu
                    260                 265                 270
        Thr Phe Cys Val Gln Val Gln Gly Lys Asn Lys Arg Glu Lys Lys Leu
                    275                 280                 285
        Phe Thr Asp Gln Thr Ser Ala Lys Val Thr Cys His Lys Asp Ala Asn
                    290                 295                 300
        Ile Arg Val Gln Ala Arg Asp Arg Tyr Tyr Ser Ser Phe Trp Ser Glu
        305                 310                 315                 320
        Trp Ala Ser Val Ser Cys Ser
                    325

<210> 31
        <211> 1015
        <212> DNA
        <213> Canis familiaris
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
<400> 31
atgcatcctc agcagttggt catctcctgg ttttccctcg ttttgctggc gtcttccctc     60
atgaccatat gggaactgga gaaagatgtt tatgttgtag agttggactg gcaccctgat    120
gccccggag aaatggtggt cctcacctgc cataccctg aagaagatga catcacttgg     180
acctcagcgc agagcagtga agtcctaggt tctggtaaaa ctctgaccat ccaagtcaaa    240
gaatttggag atgctggcca gtatacctgc cataaaggag gcaaggttct gagccgctca    300
ctcctgttga ttcacaaaaa agaagatgga atttggtcca ctgatatctt aaaggaacag    360
aaagaatcca aaaataagat cttttctgaaa tgtgaggcaa agaattattc tggacgtttc    420
acatgctgt ggctgacggc aatcagtact gatttgaaat tcagtgtcaa aagtagcaga    480
ggcttctctg acccccaagg ggtgacatgt ggagcagtga cactttcagc agagagggtc    540
agagtggaca acagggatta taagaagtac acagtggagt gtcaggaagg cagtgcctgc    600
ccctctgccg aggagagcct acccatcgag gtcgtggtgg atgctattca caagctcaag    660
tatgaaaact acaccagcag cttcttcatc agagacatca tcaaccaga cccacccaca    720
aacctgcagc tgaagccatt gaaaaattct cggcacgtgg aggtcagctg gaatacccc    780
gacacctgga gcaccccaca ttcctacttc tccctgacat tttgcgtaca ggcccagggc    840
aagaacaata gagaaagaa agatagactc tgcgtggaca agacctcagc caaggtcgtg    900
tgccacaagc atgccaagat ccgcgtgcaa gcccgagacc gctactatag ttcatcctgg    960
agcgactggg catctgtgtc ctgcagttag gttccacccc caggatgaat cttgg        1015

<210> 32
<211> 329
<212> PRT
<213> Canis familiaris

<400> 32
Met His Pro Gln Gln Leu Val Ile Ser Trp Phe Ser Leu Val Leu Leu
 1               5                  10                  15
Ala Ser Ser Leu Met Thr Ile Trp Glu Leu Glu Lys Asp Val Tyr Val
             20                  25                  30
Val Glu Leu Asp Trp His Pro Asp Ala Pro Gly Glu Met Val Val Leu
         35                  40                  45
Thr Cys His Thr Pro Glu Glu Asp Asp Ile Thr Trp Thr Ser Ala Gln
     50                  55                  60
Ser Ser Glu Val Leu Gly Ser Gly Lys Thr Leu Thr Ile Gln Val Lys
65                  70                  75                  80
Glu Phe Gly Asp Ala Gly Gln Tyr Thr Cys His Lys Gly Gly Lys Val
                 85                  90                  95
```

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Leu Ser Arg Ser Leu Leu Leu Ile His Lys Lys Glu Asp Gly Ile Trp
            100                 105                 110
Ser Thr Asp Ile Leu Lys Glu Gln Lys Glu Ser Lys Asn Lys Ile Phe
            115                 120                 125
Leu Lys Cys Glu Ala Lys Asn Tyr Ser Gly Arg Phe Thr Cys Trp Trp
            130                 135                 140
Leu Thr Ala Ile Ser Thr Asp Leu Lys Phe Ser Val Lys Ser Ser Arg
145                 150                 155                 160
Gly Phe Ser Asp Pro Gln Gly Val Thr Cys Gly Ala Val Thr Leu Ser
                165                 170                 175
Ala Glu Arg Val Arg Val Asp Asn Arg Asp Tyr Lys Lys Tyr Thr Val
            180                 185                 190
Glu Cys Gln Glu Gly Ser Ala Cys Pro Ser Ala Glu Glu Ser Leu Pro
            195                 200                 205
Ile Glu Val Val Val Asp Ala Ile His Lys Leu Lys Tyr Glu Asn Tyr
            210                 215                 220
Thr Ser Ser Phe Phe Ile Arg Asp Ile Ile Lys Pro Asp Pro Pro Thr
225                 230                 235                 240
Asn Leu Gln Leu Lys Pro Leu Lys Asn Ser Arg His Val Glu Val Ser
                245                 250                 255
Trp Glu Tyr Pro Asp Thr Trp Ser Thr Pro His Ser Tyr Phe Ser Leu
                260                 265                 270
Thr Phe Cys Val Gln Ala Gln Gly Lys Asn Asn Arg Glu Lys Lys Asp
            275                 280                 285
Arg Leu Cys Val Asp Lys Thr Ser Ala Lys Val Val Cys His Lys Asp
            290                 295                 300
Ala Lys Ile Arg Val Gln Ala Arg Asp Arg Tyr Tyr Ser Ser Ser Trp
305                 310                 315                 320
Ser Asp Trp Ala Ser Val Ser Cys Ser
                325

<210> 33
<211> 1005
<212> DNA
<213> Cercocebus torquatus
```

UNITED STATES PATENT AND TRADEMARK OFFICE
CERTIFICATE OF CORRECTION

PATENT NO.        : 7,183,382 B2
APPLICATION NO.   : 10/375706
DATED             : February 27, 2007
INVENTOR(S)       : Oppmann et al.

It is certified that error appears in the above-identified patent and that said Letters Patent is hereby corrected as shown below:

```
<400> 33
agagcaagat gtgtcaccag cagctggtca tctcttggtt ttccctggtt tttctggcat    60
ctccctcat ggccatatgg gaactgaaga aagacgttta tgttgtagaa ttggactggt   120
acccggatgc ccctggagaa atggtggtcc tcacctgtga caccctgaa gaagatggta   180
tcacctggac cttggaccag agtggtgagg tcttaggctc tggcaaaacc ctgaccatcc   240
aagtcaaaga gtttggagat gctggccagt acacctgtca caaaggaggc gaggctttga   300
gccattcact cctgctgcct cacaaaaagg aagatggaat ttggtccact gatattttaa   360
aggaccagaa agaaccaaa aatgagacct ttctaagatg cgaggccaaa aattattctg   420
gacgtatcac ctgctggtgg ctgtcgacaa tcagtactga tctgacattc agtatcataa   480
gcagcagagg ctcttctaac ccccaagggg tgacgtgtgg agccgctaca ctctctgcag   540
agagggtcag agggacaat aaggagtatg agtactcagt ggagtgccag gaggacagtg   600
cctgcccagc cgctgaggag aggctgccca ttgaggtcat ggtggatgcc attcacaagc   660
tcaagtatga aaactacacc agcagcttct tcatcaggga catcatcaaa cccgacccac   720
ccaagaactt gcagctgaag ccattaaaga attctcggca ggtggaggtc agctgggagt   780
acctgacac ctggagtact ccacattcct acttctcct gacattctgc attcaggtcc   840
agggcaagag caagagagaa aagaaagata gaatcttcac agacaagacc tcagccacgg   900
tcatctgccg caaaaatgcc agctttagcg tgcaggccca ggaccgctac tatagctcat   960
cttggaacga atggacatct gtgccctgca gttaggttct gatcc                 1005

<210> 34
<211> 328
<212> PRT
<213> Cercocebus torquatus

<400> 34
Met Cys His Gln Gln Leu Val Ile Ser Trp Phe Ser Leu Val Phe Leu
 1               5                  10                   15
Ala Ser Pro Leu Met Ala Ile Trp Glu Leu Lys Lys Asp Val Tyr Val
                20                  25                   30
Val Glu Leu Asp Trp Tyr Pro Asp Ala Pro Gly Glu Met Val Val Leu
                35                      40                   45
Thr Cys Asp Thr Pro Glu Glu Asp Gly Ile Thr Trp Thr Leu Asp Gln
            50                      55                   60
Ser Gly Glu Val Leu Gly Ser Gly Lys Thr Leu Thr Ile Gln Val Lys
65                      70                   75                   80
Glu Phe Gly Asp Ala Gly Gln Tyr Thr Cys His Lys Gly Gly Glu Ala
                    85                  90                   95
```

Page 37 of 40

UNITED STATES PATENT AND TRADEMARK OFFICE
CERTIFICATE OF CORRECTION

PATENT NO. : 7,183,382 B2
APPLICATION NO. : 10/375706
DATED : February 27, 2007
INVENTOR(S) : Oppmann et al.

It is certified that error appears in the above-identified patent and that said Letters Patent is hereby corrected as shown below:

```
Leu Ser His Ser Leu Leu Leu Pro His Lys Lys Glu Asp Gly Ile Trp
        100             105             110
Ser Thr Asp Ile Leu Lys Asp Gln Lys Glu Pro Lys Asn Glu Thr Phe
        115             120             125
Leu Arg Cys Glu Ala Lys Asn Tyr Ser Gly Arg Ile Thr Cys Trp Trp
        130             135             140
Leu Ser Thr Ile Ser Thr Asp Leu Thr Phe Ser Ile Ile Ser Ser Arg
145             150             155             160
Gly Ser Ser Asn Pro Gln Gly Val Thr Cys Gly Ala Ala Thr Leu Ser
                165             170             175
Ala Glu Arg Val Arg Gly Asp Asn Lys Glu Tyr Glu Tyr Ser Val Glu
                180             185             190
Cys Gln Glu Asp Ser Ala Cys Pro Ala Ala Glu Glu Arg Leu Pro Ile
            195             200             205
Glu Val Met Val Asp Ala Ile His Lys Leu Lys Tyr Glu Asn Tyr Thr
        210             215             220
Ser Ser Phe Phe Ile Arg Asp Ile Ile Lys Pro Asp Pro Pro Lys Asn
225             230             235             240
Leu Gln Leu Lys Pro Leu Lys Asn Ser Arg Gln Val Glu Val Ser Trp
                245             250             255
Glu Tyr Pro Asp Thr Trp Ser Thr Pro His Ser Tyr Phe Ser Leu Thr
            260             265             270
Phe Cys Ile Gln Val Gln Gly Lys Ser Lys Arg Glu Lys Lys Asp Arg
        275             280             285
Ile Phe Thr Asp Lys Thr Ser Ala Thr Val Ile Cys Arg Lys Asn Ala
        290             295             300
Ser Phe Ser Val Gln Ala Gln Asp Arg Tyr Tyr Ser Ser Ser Trp Asn
305             310             315             320
Glu Trp Thr Ser Val Pro Cys Ser
                325

<210> 35
<211> 984
<212> DNA
<213> Marmota monax
```

UNITED STATES PATENT AND TRADEMARK OFFICE
CERTIFICATE OF CORRECTION

PATENT NO.       : 7,183,382 B2
APPLICATION NO.  : 10/375706
DATED            : February 27, 2007
INVENTOR(S)      : Oppmann et al.

It is certified that error appears in the above-identified patent and that said Letters Patent is hereby corrected as shown below:

```
<400> 35
atgtgtcttc agcagttggt catctcctgg gtctccctgg tttggctggc atctcccctc    60
ttggccatat gggaactgga gaaaaatgtc tacgtggtgg agttggattg gcaccctgac   120
acacctggag aaaaggtggt cctcacctgt gacactcctg aagaagacgg catcacctgg   180
acctcagagc agagcagtga ggtcttaggc tccggcaaaa ccctgaccat tctagtcaaa   240
gagtttgaag acgctggcca ctacacctgc cgcagaggag gtgaagttct gagccagatg   300
ctcctgctgc ttcacaaaaa tgaagatggg atttggtcca ctgatattct gaagaaaaaa   360
gaacctgaaa ataagaacct tgtaacatgc gaggcaaaga attactctgg acgtttttacc   420
tgctggtggc tgacggcaat cagtactgat gtgaacttca gtgtcaagag ccacagaggc   480
tcctctgacc ctcaagggt gacgtgtgga gaagcaactc tctctgcaga gagggtcaaa   540
atagagcaga gggagtacaa gaagtactcg gtgcagtgcc aggaggacaa tgcctgcccc   600
accgctgagg agaccctgcc catcacagtg gtggtggacg cagttcacaa gctcaagtac   660
gaaaactaca tcagcagctt cttcatcaga gacatcatca aacctgaccc acccaagaac   720
ctaaagatga gccatccaa gactcctcag caggtggagg tcacctggga gtacccggac   780
agctggagca ccccgcactc ctacttctcc ctgacattct ctgtgcaggt ccagggcaaa   840
aagaagaaaa ggagcaatac tctccacgtg gataagacct cagtcacagt gacctgccag   900
aagggtgcca aggtcagcgt gcaagcccgg gaccgatact acaactcatc gtggagtgaa   960
tgggcaacta tgtcctgccc ttag                                         984

<210> 36
<211> 327
<212> PRT
<213> Marmota monax

<400> 36
Met Cys Leu Gln Gln Leu Val Ile Ser Trp Val Ser Leu Val Trp Leu
 1               5                  10                  15
Ala Ser Pro Leu Leu Ala Ile Trp Glu Leu Glu Lys Asn Val Tyr Val
                20                  25                  30
Val Glu Leu Asp Trp His Pro Asp Thr Pro Gly Glu Lys Val Val Leu
            35                  40                  45
Thr Cys Asp Thr Pro Glu Glu Asp Gly Ile Thr Trp Thr Ser Glu Gln
 50                  55                  60
Ser Ser Glu Val Leu Gly Ser Gly Lys Thr Leu Thr Ile Leu Val Lys
65                  70                  75                  80
Glu Phe Glu Asp Ala Gly His Tyr Thr Cys Arg Arg Gly Gly Glu Val
                85                  90                  95
```

UNITED STATES PATENT AND TRADEMARK OFFICE
CERTIFICATE OF CORRECTION

PATENT NO.       : 7,183,382 B2
APPLICATION NO.  : 10/375706
DATED            : February 27, 2007
INVENTOR(S)      : Oppmann et al.

It is certified that error appears in the above-identified patent and that said Letters Patent is hereby corrected as shown below:

```
Leu Ser Gln Met Leu Leu Leu Leu His Lys Asn Glu Asp Gly Ile Trp
            100                 105                 110
Ser Thr Asp Ile Leu Lys Lys Lys Glu Pro Glu Asn Lys Asn Leu Val
            115                 120                 125
Thr Cys Glu Ala Lys Asn Tyr Ser Gly Arg Phe Thr Cys Trp Trp Leu
            130                 135                 140
Thr Ala Ile Ser Thr Asp Val Asn Phe Ser Val Lys Ser His Arg Gly
145                     150                 155                 160
Ser Ser Asp Pro Gln Gly Val Thr Cys Gly Glu Ala Thr Leu Ser Ala
                165                 170                 175
Glu Arg Val Lys Ile Glu Gln Arg Glu Tyr Lys Lys Tyr Ser Val Gln
            180                 185                 190
Cys Gln Glu Asp Asn Ala Cys Pro Thr Ala Glu Glu Thr Leu Pro Ile
            195                 200                 205
Thr Val Val Val Asp Ala Val His Lys Leu Lys Tyr Glu Asn Tyr Ile
            210                 215                 220
Ser Ser Phe Phe Ile Arg Asp Ile Ile Lys Pro Asp Pro Pro Lys Asn
225                     230                 235                 240
Leu Lys Met Lys Pro Ser Lys Thr Pro Gln Gln Val Glu Val Thr Trp
                245                 250                 255
Glu Tyr Pro Asp Ser Trp Ser Thr Pro His Ser Tyr Phe Ser Leu Thr
            260                 265                 270
Phe Ser Val Gln Val Gln Gly Lys Lys Lys Arg Ser Asn Thr Leu
            275                 280                 285
His Val Asp Lys Thr Ser Val Thr Val Thr Cys Gln Lys Gly Ala Lys
            290                 295                 300
Val Ser Val Gln Ala Arg Asp Arg Tyr Tyr Asn Ser Ser Trp Ser Glu
305                     310                 315                 320
Trp Ala Thr Met Ser Cys Pro
                325
```
--

UNITED STATES PATENT AND TRADEMARK OFFICE
CERTIFICATE OF CORRECTION

| | | |
|---|---|---|
| PATENT NO. | : 7,183,382 B2 | |
| APPLICATION NO. | : 10/375706 | |
| DATED | : February 27, 2007 | |
| INVENTOR(S) | : Oppmann et al. | |

It is certified that error appears in the above-identified patent and that said Letters Patent is hereby corrected as shown below:

Please add the following to the cover page of the patent between "Prior Publication Data" and the International Classifications:

-- Related U.S. Application Data

(62) Division of application No. 09/658,699, filed on Sep. 8, 2000, now U.S. Pat. No. 7,090,847.

(60) Provisional application No. 60/164,616, filed on Nov. 10, 1999, and provisional application No. 60/153,281, filed on Sep. 9, 1999. --

Please replace the paragraph beginning at page 1, line 5, with the following rewritten paragraph:

-- This application is a Divisional of U.S. Patent Application No. 09/658,699, filed on September 8, 2000, now U.S. Pat. No. 7,090,847, which claims the benefit of United States Provisional Patent Application No. 60/164,616, filed November 10, 1999, and Provisional Patent Application No. 60/153,281, filed September 9, 1999, each of which is incorporated herein by reference. --

Signed and Sealed this
Eighteenth Day of September, 2012

David J. Kappos
*Director of the United States Patent and Trademark Office*